United States Patent
Yamazaki et al.

(10) Patent No.: US 11,933,974 B2
(45) Date of Patent: Mar. 19, 2024

(54) GLASSES-TYPE ELECTRONIC DEVICE

(71) Applicant: SEMICONDUCTOR ENERGY LABORATORY CO., LTD., Atsugi (JP)

(72) Inventors: Shunpei Yamazaki, Tokyo (JP); Takayuki Ikeda, Kanagawa (JP); Hidetomo Kobayashi, Kanagawa (JP); Hideaki Shishido, Kanagawa (JP); Kiyotaka Kimura, Kanagawa (JP); Takashi Nakagawa, Kanagawa (JP); Kosei Nei, Kanagawa (JP); Kentaro Hayashi, Kanagawa (JP)

(73) Assignee: Semiconductor Energy Laboratory Co., Ltd., Atsugi (JP)

( * ) Notice: Subject to any disclaimer, the term of this patent is extended or adjusted under 35 U.S.C. 154(b) by 45 days.

(21) Appl. No.: 17/429,979

(22) PCT Filed: Feb. 13, 2020

(86) PCT No.: PCT/IB2020/051163
§ 371 (c)(1),
(2) Date: Aug. 11, 2021

(87) PCT Pub. No.: WO2020/170083
PCT Pub. Date: Aug. 27, 2020

(65) Prior Publication Data
US 2022/0137409 A1    May 5, 2022

(30) Foreign Application Priority Data

Feb. 22, 2019  (JP) ................................ 2019-030646

(51) Int. Cl.
*G02B 27/00*    (2006.01)
*A61B 5/00*    (2006.01)
(Continued)

(52) U.S. Cl.
CPC ..... *G02B 27/0093* (2013.01); *G02B 27/0101* (2013.01); *G02B 27/0172* (2013.01);
(Continued)

(58) Field of Classification Search
USPC .............................................................. 345/8
See application file for complete search history.

(56) References Cited

U.S. PATENT DOCUMENTS 8,542,928 B2    9/2013  Kaneda. et al.
9,628,707 B2    4/2017  Blum et al.
(Continued)

FOREIGN PATENT DOCUMENTS

CN    101630064 A    1/2010
CN    103885206 A    6/2014
(Continued)

OTHER PUBLICATIONS

International Search Report (Application No. PCT/IB2020/051163) dated Jun. 2, 2020.
(Continued)

*Primary Examiner* — Chineyere D Wills-Burns
(74) *Attorney, Agent, or Firm* — Fish & Richardson P.C.

(57) ABSTRACT

An object is to provide an electronic device capable of recognizing a user's facial feature accurately. A glasses-type electronic device includes a first optical component, a second optical component, a frame, an imaging device, a feature extraction unit, and an emotion estimation unit. The frame is in contact with a side surface of the first optical component and a side surface of the second optical component. The imaging device is in contact with the frame and has a function of detecting part of a user's face. The feature extraction unit has a function of extracting a feature of the user's face from the detected part of the user's face. The
(Continued)

emotion estimation unit has a function of estimating information on the user from the extracted feature.

11 Claims, 43 Drawing Sheets

(51) Int. Cl.
| | | |
|---|---|---|
| *A61B 5/11* | (2006.01) | |
| *A61B 5/16* | (2006.01) | |
| *G02B 27/01* | (2006.01) | |
| *G06F 3/147* | (2006.01) | |
| *G06T 7/73* | (2017.01) | |
| *G06V 10/44* | (2022.01) | |
| *G06V 10/764* | (2022.01) | |
| *G06V 10/82* | (2022.01) | |
| *G06V 20/20* | (2022.01) | |
| *G06V 30/19* | (2022.01) | |
| *G06V 40/16* | (2022.01) | |
| *G09G 3/3225* | (2016.01) | |
| *G11C 19/28* | (2006.01) | |

(52) U.S. Cl.
CPC .......... *G02B 27/0176* (2013.01); *G06T 7/73* (2017.01); *G06V 10/454* (2022.01); *G06V 10/764* (2022.01); *G06V 10/82* (2022.01); *G06V 20/20* (2022.01); *G06V 40/174* (2022.01); *G02B 2027/0138* (2013.01); *G02B 2027/014* (2013.01); *G02B 2027/0178* (2013.01); *G06T 2207/30201* (2013.01)

(56) References Cited

U.S. PATENT DOCUMENTS

| | | | |
|---|---|---|---|
| 9,635,222 | B2 | 4/2017 | Blum |
| 9,823,494 | B2 | 11/2017 | Blum et al. |
| 9,930,257 | B2 | 3/2018 | Blum et al. |
| 10,027,896 | B2 | 7/2018 | Ikeda |
| 10,185,163 | B2 | 1/2019 | Blum et al. |
| 10,241,351 | B2 | 3/2019 | Blum et al. |
| 10,341,787 | B2 | 7/2019 | Blum et al. |
| 10,348,965 | B2 | 7/2019 | Blum et al. |
| 10,481,417 | B2 | 11/2019 | Blum et al. |
| 10,620,459 | B2 | 4/2020 | Blum et al. |
| 10,887,516 | B2 | 1/2021 | Blum et al. |
| 11,049,147 | B2 | 6/2021 | Chintalapoodi et al. |
| 11,166,112 | B2 | 11/2021 | Blum et al. |
| 2001/0028309 | A1* | 10/2001 | Torch ................ A61B 5/1103 340/576 |
| 2007/0001982 | A1* | 1/2007 | Ito .................... G09G 3/2011 345/98 |
| 2007/0122036 | A1 | 5/2007 | Kaneda et al. |
| 2009/0003709 | A1* | 1/2009 | Kaneda ............... G06V 10/454 382/190 |
| 2011/0263946 | A1 | 10/2011 | el Kaliouby et al. |
| 2013/0300636 | A1* | 11/2013 | Cunningham ........ G06F 3/013 345/8 |
| 2013/0322770 | A1 | 12/2013 | Kaneda et al. |
| 2015/0061824 | A1 | 3/2015 | Suzuki et al. |
| 2015/0209174 | A1* | 7/2015 | Abreu .................... A61F 7/02 607/104 |
| 2015/0279918 | A1 | 10/2015 | Teraguchi et al. |
| 2016/0043363 | A1 | 2/2016 | Tajima et al. |
| 2016/0172870 | A1 | 6/2016 | Blum et al. |
| 2016/0261147 | A1 | 9/2016 | Blum et al. |
| 2016/0294225 | A1 | 10/2016 | Blum et al. |
| 2017/0150049 | A1 | 5/2017 | Blum et al. |
| 2017/0186355 | A1* | 6/2017 | Takahashi ............ G09G 3/3648 |
| 2017/0195529 | A1 | 7/2017 | Blum |
| 2017/0352690 | A1* | 12/2017 | Yamazaki ........... H01L 27/1225 |
| 2017/0358254 | A1* | 12/2017 | Inoue .................. G09G 3/3648 |
| 2018/0012536 | A1* | 1/2018 | Shishido .............. G09G 3/2092 |
| 2018/0211112 | A1 | 7/2018 | Asbun et al. |
| 2018/0249078 | A1 | 8/2018 | Blum et al. |
| 2019/0012528 | A1 | 1/2019 | Wilson et al. |
| 2019/0204599 | A1* | 7/2019 | Abbott .................. G06T 19/006 |
| 2019/0340780 | A1* | 11/2019 | Hiraide .................. H04N 17/00 |
| 2020/0041822 | A1 | 2/2020 | Blum et al. |
| 2020/0127064 | A1 | 4/2020 | Ikeda et al. |
| 2020/0245873 | A1* | 8/2020 | Frank .................. A61B 5/0823 |
| 2021/0111196 | A1 | 4/2021 | Yamazaki et al. |
| 2021/0279449 | A1* | 9/2021 | Yamazaki ................ G06N 3/08 |
| 2022/0038626 | A1 | 2/2022 | Blum et al. |
| 2022/0060836 | A1 | 2/2022 | Blum et al. |

FOREIGN PATENT DOCUMENTS

| | | |
|---|---|---|
| CN | 105138119 A | 12/2015 |
| CN | 106772980 A | 5/2017 |
| EP | 3055754 A | 8/2016 |
| EP | 3293691 A | 3/2018 |
| EP | 3872559 A | 9/2021 |
| JP | 2007-087346 A | 4/2007 |
| JP | 2015-046070 A | 3/2015 |
| JP | 2015-194577 A | 11/2015 |
| JP | 2016-002109 A | 1/2016 |
| JP | 2017-129857 A | 7/2017 |
| JP | 2018-041460 A | 3/2018 |
| JP | 2019-009627 A | 1/2019 |
| KR | 2016-0068916 A | 6/2016 |
| TW | 201610506 | 3/2016 |
| WO | WO-2015/054562 | 4/2015 |
| WO | WO-2016/022499 | 2/2016 |
| WO | WO-2016/100339 | 6/2016 |
| WO | WO-2016/105480 | 6/2016 |
| WO | WO-2016/141349 | 9/2016 |
| WO | WO-2016/201261 | 12/2016 |
| WO | WO-2016/205373 | 12/2016 |
| WO | WO-2017/075405 | 5/2017 |
| WO | WO-2017/122299 | 7/2017 |

OTHER PUBLICATIONS

Written Opinion (Application No. PCT/IB2020/051163) dated Jun. 2, 2020.

Taiwanese Office Action (Application No. 109105278) dated Oct. 18, 2023.

* cited by examiner

GLASSES-TYPE ELECTRONIC DEVICE

CROSS REFERENCE TO RELATED APPLICATIONS

This application is a U.S. National Phase Application under 35 U.S.C. § 371 of International Application PCT/IB2020/051163, filed on Feb. 13, 2020, and claims the benefit of foreign a priority application filed in Japan on Feb. 22, 2019, as Application No. 2019-030646, both of which are incorporated by reference.

TECHNICAL FIELD

One embodiment of the present invention relates to a glasses-type electronic device.

Note that one embodiment of the present invention is not limited to the above technical field. Examples of the technical field of one embodiment of the present invention disclosed in this specification and the like include a semiconductor device, a display device, a light-emitting device, a power storage device, a memory device, an electronic device, a lighting device, an input device, an input/output device, a driving method thereof, and a manufacturing method thereof. A semiconductor device generally means a device that can function by utilizing semiconductor characteristics.

BACKGROUND ART

Techniques of recognizing facial expressions from captured images of faces are known. Facial expression recognition is applied, for example, to a technique by which a digital camera or the like takes images automatically at the moment when a subject smiles or when the subject stares into the camera.

As an example of a technique of facial expression recognition, Patent Document 1 discloses a technique in which facial feature points are detected and facial expressions are recognized with high accuracy on the basis of the detected feature points.

REFERENCE

Patent Document

[Patent Document 1] Japanese Published Patent Application No. 2007-087346

DISCLOSURE OF INVENTION

Facial expression recognition is performed, for example, by irradiating a face with infrared light and detecting the reflected infrared light. If a light source that emits infrared light or the like and a sensor that detects the reflected infrared light or the like are apart from the face, particularly from the eyes, there is a possibility that a facial expression cannot be recognized accurately.

An object of one embodiment of the present invention is to provide an electronic device capable of recognizing a user's facial feature accurately. Another object of one embodiment of the present invention is to provide an electronic device capable of estimating a user's emotions accurately. Another object of one embodiment of the present invention is to provide an electronic device capable of estimating a user's fatigue level accurately. Another object of one embodiment of the present invention is to provide a novel electronic device.

Another object of one embodiment of the present invention is to provide an electronic device including a display device including a large number of pixels. Another object of one embodiment of the present invention is to provide an electronic device including a high-definition display device. Another object of one embodiment of the present invention is to provide an electronic device including a display device capable of displaying high-definition images. Another object of one embodiment of the present invention is to provide an electronic device including a display device capable of displaying high-quality images. Another object of one embodiment of the present invention is to provide an electronic device including a display device capable of displaying highly realistic images. Another object of one embodiment of the present invention is to provide an electronic device including a display device capable of displaying high-luminance images. Another object of one embodiment of the present invention is to provide an electronic device including a display device having a narrow frame. Another object of one embodiment of the present invention is to provide an electronic device including a small display device. Another object of one embodiment of the present invention is to provide an electronic device including a display device that operates at high speed. Another object of one embodiment of the present invention is to provide an electronic device including a display device with low power consumption. Another object of one embodiment of the present invention is to provide an electronic device including an inexpensive display device. Another object of one embodiment of the present invention is to provide an electronic device including a highly reliable display device. Another object of one embodiment of the present invention is to provide an electronic device including a novel display device.

Another object of one embodiment of the present invention is to provide a novel display device. Another object of one embodiment of the present invention is to provide a novel imaging device.

Note that the description of these objects does not preclude the existence of other objects. One embodiment of the present invention does not have to achieve all these objects. Note that other objects can be derived from the description of the specification, the drawings, the claims, and the like.

One embodiment of the present invention is a glasses-type electronic device including a first optical component, a second optical component, a frame, an imaging device, a feature extraction unit, and an emotion estimation unit. The frame is in contact with a side surface of the first optical component and a side surface of the second optical component. The imaging device is in contact with the frame. The imaging device has a function of detecting part of a user's face. The feature extraction unit has a function of extracting a feature of the user's face from the detected part of the user's face. The emotion estimation unit has a function of estimating information on the user from the extracted feature.

In the above embodiment, the information is the degree of fatigue or emotion of the user.

In the above embodiment, the glasses-type electronic device may include a display device. The display device may display an image corresponding to the information.

In the above embodiment, the display device may include a light-emitting element. The light-emitting element may be an organic EL element.

In the above embodiment, the display device may include a transistor. The transistor may contain a metal oxide in a channel formation region.

One embodiment of the present invention is a glasses-type electronic device including a first optical component, a second optical component, a frame, an imaging device, and a display device. The imaging device includes a photoelectric conversion element having a function of detecting the amount of received light. The frame is in contact with a side surface of the first optical component and a side surface of the second optical component. The imaging device is in contact with the frame. The display device includes a first layer and a second layer that are stacked. The first layer includes a gate driver circuit and a source driver circuit. The second layer includes a pixel array including a matrix of pixels. The gate driver circuit and the source driver circuit each include a region overlapping with some of the pixels. The gate driver circuit includes a region overlapping with the source driver circuit.

In the above embodiment, the display device may include a D/A converter circuit. The D/A converter circuit may include a potential generator circuit and a pass transistor logic circuit. The potential generator circuit may be provided outside the source driver circuit. The pass transistor logic circuit may be provided in the source driver circuit. The potential generator circuit may have a function of generating a plurality of potentials having different levels. The pass transistor logic circuit may have a function of receiving image data and outputting any of the potentials generated by the potential generator circuit on the basis of a digital value of the image data.

In the above embodiment, each of the pixels may include a light-emitting element. The light-emitting element may be an organic EL element.

In the above embodiment, each of the pixels may include a transistor. The transistor may contain a metal oxide in a channel formation region.

On embodiment can provide an electronic device capable of recognizing a user's facial feature accurately. One embodiment of the present invention can provide an electronic device capable of estimating a user's emotions accurately. One embodiment of the present invention can provide an electronic device capable of estimating a user's fatigue level accurately. One embodiment of the present invention can provide a novel electronic device.

One embodiment of the present invention can provide an electronic device including a display device including a large number of pixels. One embodiment of the present invention can provide an electronic device including a high-definition display device. One embodiment of the present invention can provide an electronic device including a display device capable of displaying high-definition images. One embodiment of the present invention can provide an electronic device including a display device capable of displaying high-quality images. One embodiment of the present invention can provide an electronic device including a display device capable of displaying highly realistic images. One embodiment of the present invention can provide an electronic device including a display device capable of displaying high-luminance images. One embodiment of the present invention can provide an electronic device including a display device having a narrow frame. One embodiment of the present invention can provide an electronic device including a small display device. One embodiment of the present invention can provide an electronic device including a display device that operates at high speed. One embodiment of the present invention can provide an electronic device including a display device with low power consumption. One embodiment of the present invention can provide an electronic device including an inexpensive display device. One embodiment of the present invention can provide an electronic device including a highly reliable display device. One embodiment of the present invention can provide an electronic device including a novel display device.

One embodiment of the present invention can provide a novel display device. One embodiment of the present invention can provide a novel imaging device.

Note that the description of these effects does not preclude the existence of other effects. One embodiment of the present invention does not necessarily achieve all the effects listed above. Other effects can be derived from the description of the specification, the drawings, the claims, and the like.

BEST MODE FOR CARRYING OUT THE INVENTION

Figure 1A:
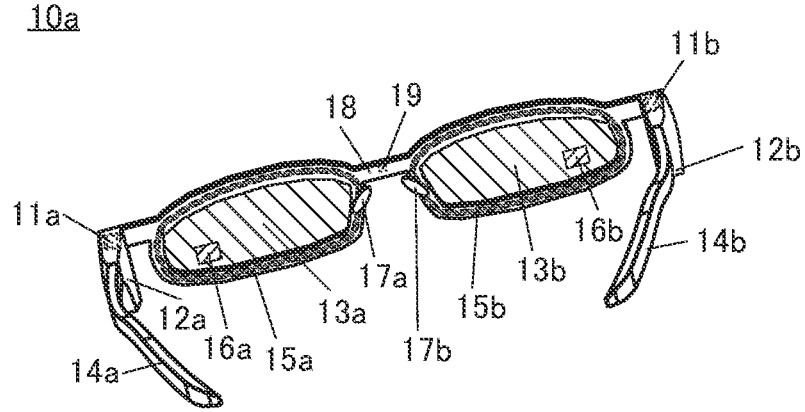
FIGS. 1A and 1B illustrate a structure example of an electronic device.

Embodiments will be hereinafter described with reference to the drawings. Note that embodiments can be implemented in many different modes, and it will be readily understood by those skilled in the art that modes and details thereof can be changed in various ways without departing from the spirit and scope of the present invention. Thus, the present invention should not be interpreted as being limited to the following description of the embodiments.

Note that in structures of the present invention described below, the same portions or portions having similar functions are denoted by the same reference numerals in different drawings, and the description thereof is not repeated. The same hatching pattern is used for portions having similar functions, and the portions are not denoted by specific reference numerals in some cases.

Note that in each drawing described in this specification, the size, the layer thickness, or the region of each component is exaggerated for clarity in some case. Therefore, the size, the layer thickness, or the region is not limited to the illustrated scale.

Note that in this specification and the like, ordinal numbers such as "first" and "second" are used in order to avoid confusion among components and do not limit the number.

In this specification, terms for describing arrangement, such as "over", "above", "under", "below", "left", and "right", are used for convenience in describing a positional relation between components with reference to drawings. The positional relation between components is changed as appropriate in accordance with the direction from which each component is described. Thus, the positional relation is not limited to that described with a term used in this specification and can be explained with other terms as appropriate depending on the situation.

A transistor is a kind of semiconductor elements and can achieve amplification of current and voltage, switching operation for controlling conduction and non-conduction, and the like. A transistor in this specification includes an insulated-gate field effect transistor (IGFET) and a thin film transistor (TFT) in its category.

In this specification and the like, functions of a source and a drain of a transistor are sometimes replaced with each other depending on the polarity of the transistor or when the direction of current flow is changed in circuit operation, for example. Therefore, the terms "source" and "drain" can be used interchangeably.

In this specification and the like, the expression "electrically connected" includes the case where components are directly connected to each other and the case where components are connected through an object having any electric function. There is no particular limitation on an object having any electric function as long as electric signals can be transmitted and received between components that are connected through the object. Thus, even when the expression "electrically connected" is used, there is a case where no physical connection is made and a wiring just extends in an actual circuit. In addition, the expression "directly connected" includes the case where different conductors are connected to each other through a contact. Note that a wiring may be formed of conductors that contain one or more of the same elements or may be formed of conductors that contain different elements.

Unless otherwise specified, an off-state current in this specification and the like refers to a drain current of a transistor in an off state (also referred to as non-conducting state or cutoff state). Unless otherwise specified, an off state refers to a state where the voltage $V_{gs}$ between a gate and a source is lower than the threshold voltage $V_{th}$ in an n-channel transistor (higher than $V_{th}$ in a p-channel transistor).

In this specification and the like, the term such as "electrode" or "wiring" does not limit the function of a component. For example, an "electrode" is used as part of a "wiring" in some cases, and vice versa. Furthermore, the term "electrode" or "wiring" can include the case where a plurality of electrodes or wirings are formed in an integrated manner.

In this specification and the like, the resistance of a resistor may depend on the length of a wiring or alternatively may depend on connection of a conductor used for a wiring to a conductor whose resistivity is different from that of the conductor. Alternatively, a resistance is sometimes determined by impurity doping in a semiconductor.

In this specification and the like, a "terminal" in an electric circuit refers to a portion that inputs or outputs current or voltage or receives or transmits a signal. Accordingly, part of a wiring or an electrode functions as a terminal in some cases.

In this specification and the like, a metal oxide means an oxide of metal in a broad sense. Metal oxides are classified into an oxide insulator, an oxide conductor (including a transparent oxide conductor), an oxide semiconductor (also simply referred to as OS), and the like. For example, a metal oxide used in an active layer of a transistor is referred to as an oxide semiconductor in some cases. In other words, an OS FET is a transistor including a metal oxide or an oxide semiconductor.

Embodiment 1

In this embodiment, an electronic device of one embodiment of the present invention will be described with reference to drawings.

FIG. 1A is a perspective view illustrating a structure example of an electronic device 10a of one embodiment of the present invention. The electronic device 10a is a glasses-type electronic device and includes a pair of display devices 11 (a display device 11a and a display device 11b), a pair of housings 12 (a housing 12a and a housing 12b), a pair of optical components 13 (an optical component 13a and an optical component 13b), a pair of wearing parts 14 (a wearing part 14a and a wearing part 14b), a pair of imaging devices 15 (an imaging device 15a and an imaging device 15b), a pair of display regions 16 (a display region 16a and a display region 16b), and a pair of nose pads 17 (a nose pad 17a and a nose pad 17b). The electronic device 10a also includes a frame 18 and a camera 19.

In the electronic device 10a, the display device 11a can be provided inside the housing 12a, and the display device 11b can be provided inside the housing 12b. The housing 12a can be provided in contact with a side surface of the left edge, for example, of the frame 18, and the housing 12b can be provided in contact with a side surface of the right edge, for example, of the frame 18.

Alternatively, the housing 12a may be provided in contact with the side surface of the right edge of the frame 18, and the housing 12b may be provided in contact with the side surface of the left edge of the frame 18.

The wearing part 14a and the wearing part 14b can be provided in contact with the housing 12a and the housing 12b, respectively. The display region 16a and the display region 16b can be provided to overlap with the optical component 13a and the optical component 13b, respectively. The frame 18 can be provided in contact with a side surface of the optical component 13a and a side surface of the optical component 13b.

The camera 19 can be provided in contact with the frame 18. For example, the camera 19 can be provided at a bridge of the frame 18. That is, the camera 19 can be provided between the optical component 13a and the optical component 13b. Alternatively, the camera 19 can be provided between the nose pad 17a and the nose pad 17b.

The display device 11a and the display device 11b have a function of displaying images. An image displayed by the display device 11a can be projected on the display region 16a. An image displayed by the display device 11b can be projected on the display region 16b. Thus, a user of the electronic device 10a can see the image displayed by the display device 11a through the display region 16a, and see the image displayed by the display device 11b through the display region 16b.

The display devices 11 preferably have a function of displaying high-definition images. For example, the display devices 11 have a function of displaying images with a definition of preferably 1000 ppi or higher, further preferably 2000 ppi or higher, still further preferably 5000 ppi or higher. Since the electronic device 10a is of glasses-type, the distance between the user's eyes and the display regions 16 is short. For that reason, if the definition of an image displayed by the display devices 11 is not high, there is a possibility that the user of the electronic device 10a perceives graininess when seeing the image displayed on the display regions 16. Accordingly, with the increase in the definition of images displayed by the display devices 11, the user of the electronic device 10a can see images displayed on the display regions 16 without perceiving graininess. Note that a specific structure example of a display device capable of displaying high-definition images will be described later.

The display devices 11 include pixels. Each of the pixels includes a subpixel with a function of emitting red light, a subpixel with a function of emitting green light, and a subpixel with a function of emitting blue light, for example. Note that the pixel included in the display device 11 may include a subpixel with a function of emitting infrared light. In that case, although the details will be described later, detecting infrared light with the imaging devices 15 can provide a function of detecting the state of the eyes and surrounding areas of the user of the electronic device 10a.

The optical components 13 have a function of transmitting incident light. For example, the optical components 13 have a function of transmitting incident visible light. The optical components 13 also have a function of refracting incident light. With the optical components 13 having a function of refracting incident light, a refractive error of the eyes of the user of the electronic device 10a can be corrected. In consideration of the above, the optical component 13 can be a lens, for example. The optical component 13 can be a concave lens, a convex lens, a progressive lens, or a multi-focus lens, for instance. The material of the optical component 13 can be plastic or glass, for instance.

Note that the optical components 13 do not necessarily have a function of refracting incident light. In the case where the optical components 13 do not have a function of refracting incident light, for example, a person without a refractive error in the eyes is less likely to have fatigue, headache, nausea, or the like when using the electronic device 10a.

When the optical components 13 have a light-transmitting property and the display regions 16 are provided, the user of the electronic device 10a can see images displayed on the display regions 16, which are superimposed on transmission images seen through the optical components 13. Thus, the electronic device 10a can be an electronic device capable of augmented reality (AR) display.

Note that the optical components 13 do not necessarily have a light-transmitting property. In the case where the optical components 13 do not have a light-transmitting property, the user of the electronic device 10a can see only images displayed on the display regions 16 without seeing the external environment. Thus, the electronic device 10a can be an electronic device capable of virtual reality (VR) display. When the optical components 13 do not have a light-transmitting property, it is preferred, for example, that the display region 16a cover the whole region occupied by the optical component 13a and the display region 16b cover the whole region occupied by the optical component 13b, in which case an image viewable by the user of the electronic device 10a can be increased in size.

The imaging devices 15 have a function of detecting light. The imaging devices 15 preferably include a light source in addition to a sensor having a function of detecting the amount of received light (a photoelectric conversion element). Accordingly, light emitted from the light source is applied to the face of the user of the electronic device 10a, for example, and the reflected light can be detected by the sensor. For example, the imaging devices 15 can have a function of detecting the state of the eyes and surrounding areas of the user of the electronic device 10a. Consequently, the electronic device 10a can have a function of recognizing the user's facial feature, such as the user's facial expression, and thus can have a function of estimating the degree of fatigue or emotion of the user, for instance.

The light source provided in the imaging device 15 preferably has a function of emitting infrared light such as near-infrared light, for example. In such a case, the sensor provided in the imaging device 15 preferably has a function of detecting infrared light such as near-infrared light, for example. Alternatively, the light source provided in the imaging device 15 preferably has a function of emitting red light, for example. In that case, the sensor provided in the imaging device 15 preferably has a function of detecting red light, for example. Accordingly, the electronic device 10a can accurately recognize the user's facial feature, such as the user's expression.

The sensor provided in the imaging device 15 may have a function of detecting far-infrared light, for example. In that case, the imaging device 15 can have a function of measuring the surface temperature of the face, for example. Thus, the electronic device 10a can have a function of estimating physical condition or emotion of the user, for instance. For example, when the imaging device 15 includes both a sensor with a function of detecting red light and a sensor with a function of detecting far-infrared light, the electronic device 10a can estimate the emotion or the like of the user more accurately.

In this specification and the like, infrared light refers to light with a wavelength ranging from 0.7 μm to 1000 μm, for example. Near-infrared light refers to light with a wavelength ranging from 0.7 μm to 2.5 μm, for example. Mid-infrared light refers to light with a wavelength ranging from 2.5 μm to 4 μm, for example. Far-infrared light refers to light with a wavelength ranging from 4 μm to 1000 μm, for example. Note that near-infrared light, mid-infrared light, or far-infrared light may be simply referred to as infrared light. In this specification and the like, red light refers to light with a wavelength ranging from 0.6 μm to 0.75 μm, for example.

The imaging devices 15 are preferably provided in contact with the frame 18. It is particularly preferred that the imaging device 15a be provided to surround the optical component 13a and the imaging device 15b be provided to surround the optical component 13b. This shortens the distance between the eyes of the user of the electronic device 10a and the imaging devices 15, so that the electronic device 10a can accurately recognize the user's facial feature, such as the user's expression.

Although the imaging device 15a surrounds the optical component 13a completely and the imaging device 15b surrounds the optical component 13b completely, one embodiment of the present invention is not limited thereto. The imaging device 15a may be provided to surround only part of the optical component 13a. The imaging device 15b may be provided to surround only part of the optical component 13b. Alternatively, two or more imaging devices 15a and two or more imaging devices 15b may be provided.

The imaging device 15 does not necessarily include a light source. In the case where the imaging device 15 does not include a light source, a light source is provided outside the imaging device 15. For example, a light source may be provided at the bridge of the frame 18. A light source may be provided between the housing 12a and the optical component 13a and between the housing 12b and the optical component 13b. When the imaging device 15 does not include a light source, photoelectric conversion elements can be provided at high density in the imaging device 15.

When the imaging device 15 does not include a light source, light that is emitted from the display device 11 and is applied to and reflected by the face of the user of the electronic device 10a, for example, can be detected by the photoelectric conversion element included in the imaging device 15. In this case, the pixel provided in the display device 11 preferably has a function of emitting infrared light.

The camera 19 has a function of capturing an image in the forward direction, that is, an image on the side opposite to the wearing parts 14. The camera 19 can be referred to as an imaging device.

Next, a method for projecting an image on the display region 16 of the electronic device 10a is described with reference to FIG. 1B. The display device 11, a lens 21, and a reflective plate 22 are provided in the housing 12. A reflective surface 23 functioning as a half mirror is provided as a portion corresponding to the display region 16 of the optical component 13.

Light 25 emitted from the display device 11 passes through the lens 21 and is reflected by the reflective plate 22 toward the optical component 13. In the optical component 13, the light 25 is fully reflected repeatedly by surfaces of an edge portion of the optical component 13 and reaches the reflective surface 23, whereby an image is projected on the reflective surface 23. Accordingly, the user can see both the light 25 reflected by the reflective surface 23 and transmitted light 26 that passes through the optical component 13 (including the reflective surface 23).

Figure 1B:
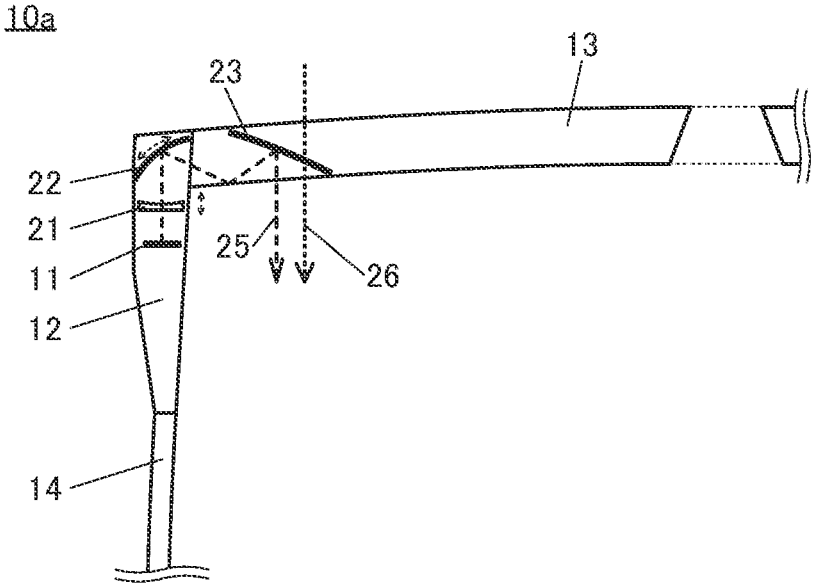

FIG. 1B illustrates an example in which the reflective plate 22 and the reflective surface 23 each have a curved surface. This structure can increase optical design flexibility and reduce the thickness of the optical component 13, compared to the case where the reflective plate 22 and the reflective surface 23 are flat. Note that the reflective plate 22 and the reflective surface 23 may be flat.

The reflective plate 22 can be a component having a mirror surface and preferably has high reflectivity. As the reflective surface 23, a half mirror utilizing reflection of a metal film may be used, but the use of a total-reflection prism, for example, can increase the transmittance of the transmitted light 26.

Here, the housing 12 preferably includes a mechanism for adjusting the distance and angle between the lens 21 and the display device 11, in which case the focus can be adjusted and images can be zoomed in and out. For example, at least one of the lens 21 and the display device 11 is preferably configured to be movable in the optical-axis direction.

The housing 12 preferably includes a mechanism capable of adjusting the angle of the reflective plate 22. The position of the display region 16 where images are displayed can be changed by changing the angle of the reflective plate 22. Thus, the display region 16 can be placed at the most appropriate position in accordance with the position of the user's eye.

Figure 2A:
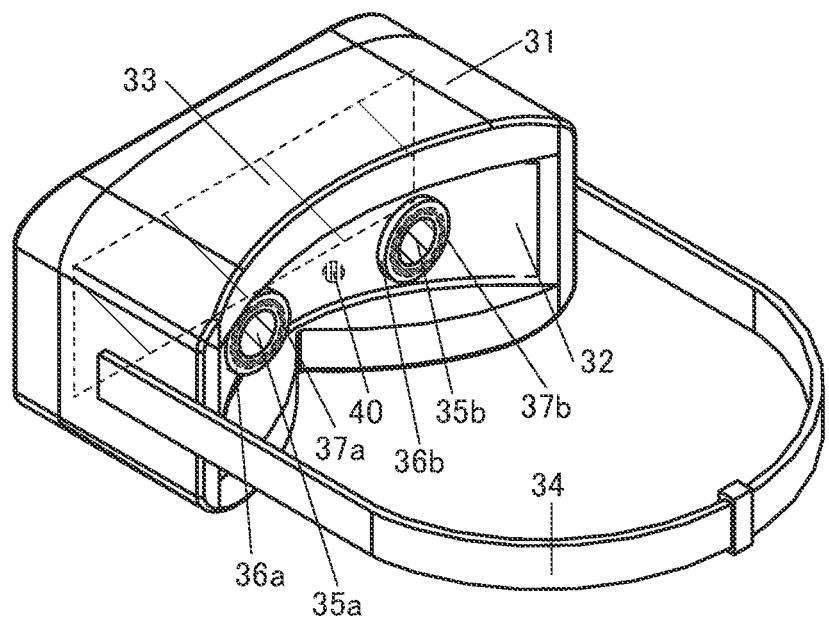
FIGS. 2A and 2B illustrate a structure example of an electronic device.
Figure 2B:
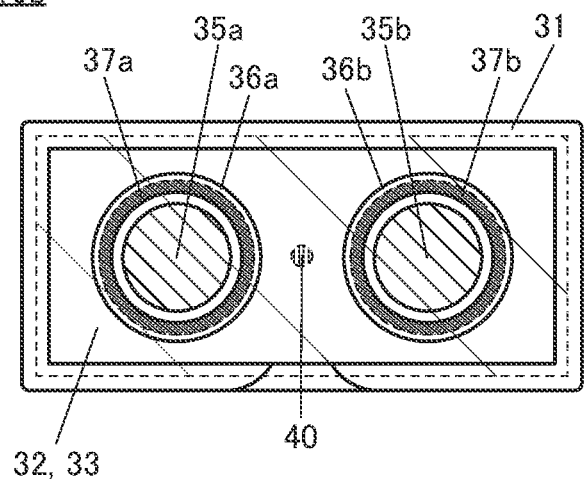

FIGS. 2A and 2B are external views illustrating a structure example of an electronic device 10b of one embodiment of the present invention. The electronic device 10b can be a head-mounted display (HMD). The electronic device 10b can be referred to as a goggles-type electronic device or a glasses-type electronic device.

The electronic device 10b includes a housing 31, a display device 33, a fixing member 34, a pair of optical components 35 (an optical component 35a and an optical component 35b), a pair of frames 36 (a frame 36a and a frame 36b), a pair of imaging devices 37 (an imaging device 37a and an imaging device 37b), and a light source 40.

The electronic device 10b includes an opening 32. The optical components 35, the frames 36, and the light source 40 are provided in contact with the opening 32. Each frame 36 is provided in contact with a side surface of the corresponding optical component 35 to surround the optical component 35. The light source 40 can be provided between the optical component 35a and the optical component 35b, for example. The display device 33 can be provided in the housing 31.

The display device 33 has a function of displaying images. A user of the electronic device 10b can see an image displayed on the display device 33 through the optical components 35. Like the display device 11 included in the electronic device 10a, the display device 33 preferably has a function of displaying high-definition images. For example, when the display device 33 has a 8-inch display region, the display device 33 preferably has a function of displaying images with a resolution of 8K4K.

The optical component 35 has a function similar to that of the optical component 13 in the electronic device 10a. The material, structure, and the like of the optical component 35 can be similar to those of the optical component 13.

The user of the electronic device 10b can see an image displayed on the display device 33 through the optical components 35. The electronic device 10b can be an electronic device capable of VR display.

The imaging device 37 has a function of detecting light. The imaging device 37 includes a photoelectric conversion element. Since the light source 40 is provided in the electronic device 10b, it is not necessary to provide a light source in the imaging device 37.

Since the electronic device 10b includes the imaging devices 37 and the light source 40, light emitted from the light source 40 is applied to the face of the user of the electronic device 10b, for example, and the reflected light can be detected by the imaging devices 37. For example, the imaging devices 37 can have a function of detecting the state of the eyes and surrounding areas of the user of the electronic device 10b. Consequently, like the electronic device 10a, the electronic device 10b can have a function of recognizing the user's facial feature, such as the user's expression, and thus can have a function of estimating the degree of fatigue or emotion of the user, for instance.

The light source 40 preferably has a function of emitting infrared light such as near-infrared light, for example. In such a case, the imaging devices 37 preferably have a function of detecting infrared light such as near-infrared light, for example. Alternatively, the light source 40 preferably has a function of emitting red light, for example. In that case, the imaging devices 37 preferably have a function of detecting red light, for example. Accordingly, the electronic device 10b can accurately recognize the user's facial feature, such as the user's expression. Moreover, like the imaging devices 15 included in the electronic device 10a, the imaging devices 37 may have a function of detecting far-infrared light, for example.

Note that the electronic device 10b does not necessarily include the light source 40. In the case where the electronic device 10b does not include the light source 40, providing a pixel having a function of emitting infrared light in the display device 33 enables the imaging devices 37 to have a function of detecting the state of the eyes and surrounding areas of the user of the electronic device 10b, for example.

The imaging device 37a is preferably provided in contact with the frame 36a. The imaging device 37b is preferably provided in contact with the frame 36b. Thus, the distance between the eyes of the user of the electronic device 10b and the imaging devices 37 can be shortened, so that the electronic device 10b can accurately recognize the user's facial feature, such as the user's expression.

Although the imaging device 37a surrounds the optical component 35a completely and the imaging device 37b surrounds the optical component 35b completely, one embodiment of the present invention is not limited thereto. The imaging device 37a may be provided to surround only part of the optical component 35a. The imaging device 37b may be provided to surround only part of the optical component 35b. Alternatively, two or more imaging devices 37a and two or more imaging devices 37b may be provided.

Figure 3A:
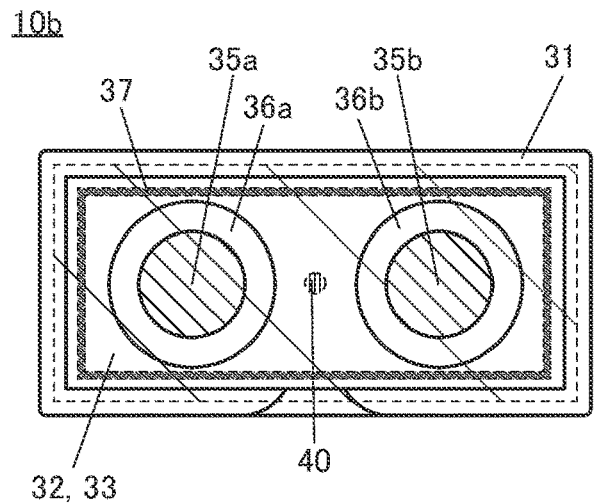
FIGS. 3A to 3C illustrate structure examples of an electronic device.

Although the imaging devices 37 are provided in contact with the frames 36 in FIGS. 2A and 2B, one embodiment of the present invention is not limited thereto. For example, the imaging device 37 may be provided in contact with the opening 32. As an example, as illustrated in FIG. 3A, the imaging device 37 may be provided to surround the optical components 35 and the frames 36.

Figure 3B:
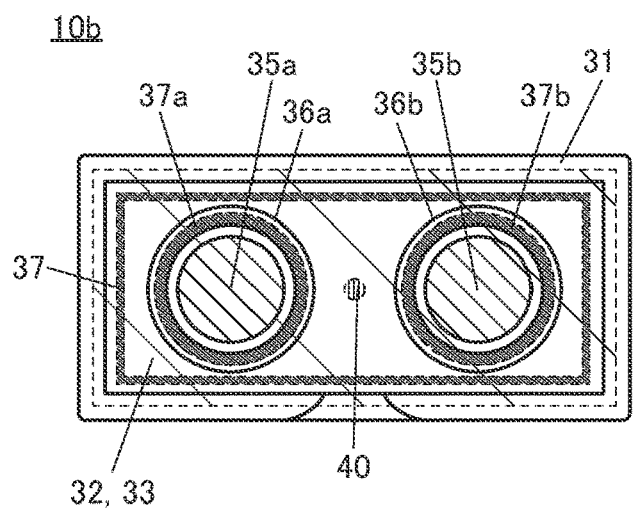

Alternatively, as illustrated in FIG. 3B, the imaging devices 37 may be provided to surround the optical components 35 and to be in contact with the frames 36, and another imaging device 37 may be provided to surround the frames 36 and to be in contact with the opening 32.

Figure 3C:
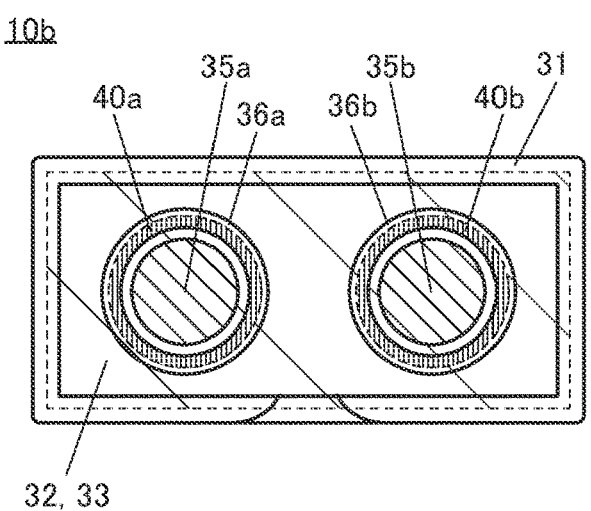

The electronic device 10b does not necessarily include the imaging device 37. In the case where the electronic device 10b does not include the imaging device 37, a light source 40a and a light source 40b can be provided in contact with the frame 36a and the frame 36b, respectively, as illustrated in FIG. 3C, for example. That is, the imaging device 37 can be replaced with the light source 40. When the electronic device 10b does not include the imaging device 37, a photoelectric conversion element is provided in the display device 33, for example. In other words, the function of the imaging device is provided to the display device 33, whereby the electronic device 10b can have a function of detecting the state of the user's eyes and surrounding areas, for example.

Figure 4:
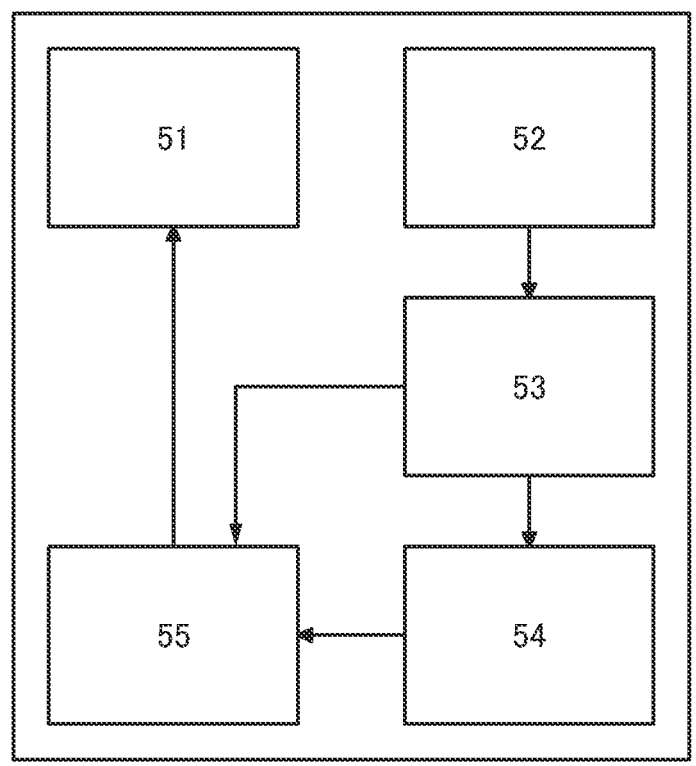
FIG. 4 is a block diagram illustrating a structure example of an electronic device.

FIG. 4 is a block diagram illustrating a structure example of an electronic device 10 (the electronic devices 10a and 10b). The electronic device 10 includes an information presentation unit 51, a subject detection unit 52, a feature extraction unit 53, an estimation unit 54, and an information generation unit 55.

Note that in a block diagram attached to this specification, components are classified according to their functions and shown as independent blocks; however, it is practically difficult to completely separate the components according to their functions, and one component may be related to a plurality of functions or a plurality of components may achieve one function.

The information presentation unit 51 has a function of stimulating the sense of sight, smell, hearing, or touch of the user of the electronic device 10. The information presentation unit 51 can present (output) information generated in the after-mentioned information generation unit 55 to the user of the electronic device 10. The display region 16 included in the electronic device 10a and the display device 33 included in the electronic device 10b can be regarded as part of the information presentation unit 51 or regarded as including the information presentation unit 51.

Various kinds of hardware can be used for the information presentation unit 51. For example, to stimulate the sense of sight of the user of the electronic device 10 (or present information visually), a display device capable of displaying images, a lighting device with variable illuminance or chromaticity, or the like can be used. As a device for stimulating the sense of smell, an aromatherapy diffuser that diffuses scent by vibration, heat, or the like can be used, for example. As a device for stimulating the sense of hearing, an audio output device such as a speaker, headphones, or earphones can be used. As a device for stimulating the sense of touch, a vibrator or the like can be used.

The subject detection unit 52 has a function of obtaining information on part of the face of the user of the electronic device 10, for instance, and outputting the information to the feature extraction unit 53. The imaging device 15 included in the electronic device 10a and the imaging device 37 included in the electronic device 10b can be regarded as part of the subject detection unit 52 or regarded as including the subject detection unit 52.

The feature extraction unit 53 has a function of extracting feature points from the facial information output from the subject detection unit 52, extracting features of part of the face or the entire face from the position of the feature points, and outputting information on the extracted features to the estimation unit 54.

When facial information obtained by the subject detection unit 52 is information on the eyes and surrounding areas, examples of features that the feature extraction unit 53 extracts include a pupil, an iris, a cornea, a conjunctiva (the white of the eye), an inner canthus, an outer canthus, an upper eyelid, a lower eyelid, eyelashes, an eyebrow, a glabella, an inner end of an eyebrow, and an outer end of an eyebrow. Examples of features other than the eyes and surrounding areas include a nasal root, a nasal apex, a nasal bridge, a nostril, lips (an upper lip and a lower lip), a corner of the mouth, an oral aperture, teeth, a cheek, a chin, a jaw, and a forehead. The feature extraction unit 53 recognizes the shape, position, and the like of these facial parts and extracts the position coordinates of the feature point of each part. Then, data on the extracted position coordinates or the like can be output to the estimation unit 54 as information on the facial features.

As a method for extracting features by the feature extraction unit 53, a variety of algorithms for extracting a feature point from an image or the like obtained by the subject detection unit 52 can be employed. For example, an algorithm such as scale-invariant feature transform (SIFT), speeded-up robust features (SURF), or histograms of oriented gradients (HOG) can be used.

Feature extraction by the feature extraction unit 53 is preferably performed by neural network inference. The case of using a neural network will be described below.

Figure 5A:
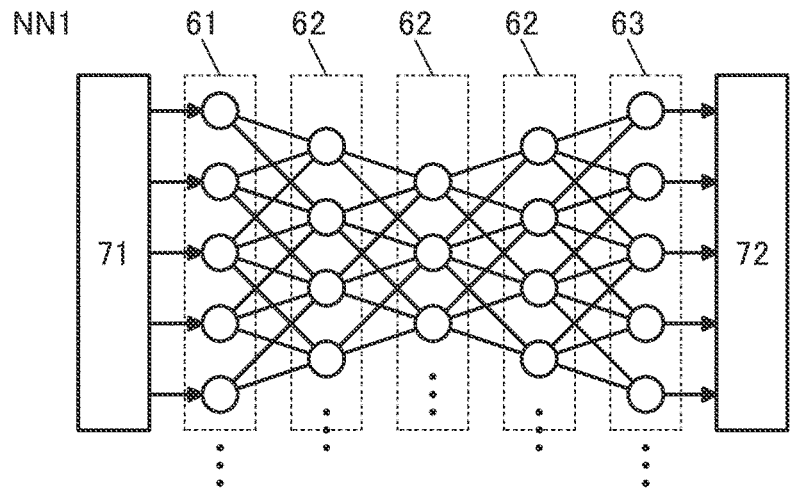
FIGS. 5A and 5B each illustrate a structure example of a neural network.

FIG. 5A schematically illustrates a neural network NN1 that can be used in the feature extraction unit 53. The neural network NN1 includes an input layer 61, three intermediate layers 62, and an output layer 63. Note that the number of intermediate layers 62 is not limited to three and can be one or more.

Data 71 generated by the subject detection unit 52 is input to the neural network NN1. The data 71 includes coordinates and a value corresponding to the coordinates. The data 71 can be typically image data that includes coordinates and a gray level corresponding to the coordinates. Data 72 is output from the neural network NN1. The data 72 includes the position coordinates of the aforementioned feature point.

The neural network NN1 has learned so as to extract the aforementioned feature point from the data 71 such as image data and output the coordinates of the feature point. The neural network NN1 has learned so that edge computing using various filters or the like in the intermediate layers 62 increases a neuron value of the output layer 63 corresponding to the coordinates of the aforementioned feature point.

The estimation unit 54 has a function of estimating fatigue, physical condition, emotions, or the like of the user of the electronic device 10 from the information on the facial features, which is input from the feature extraction unit 53, and outputting the estimated information to the information generation unit 55. Here, the estimation unit 54 preferably has a function of estimating the degree (level) of fatigue, physical condition, emotions, or the like.

Estimation by the estimation unit 54 is preferably performed by neural network inference.

Figure 5B:
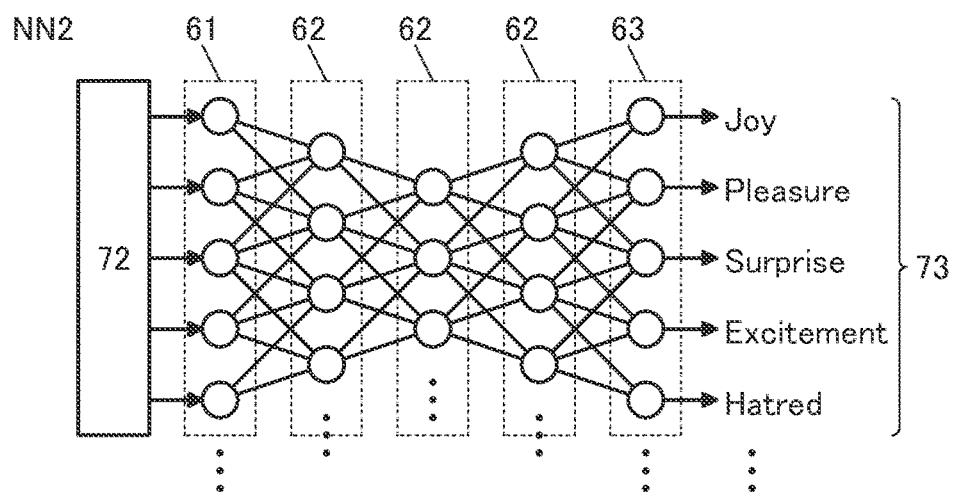

FIG. 5B schematically illustrates a neural network NN2 that can be used in the estimation unit 54. FIG. 5B shows the case where the estimation unit 54 estimates emotions of the user of the electronic device 10. An example where the neural network NN2 has substantially the same structure as the neural network NN1 is shown here. Note that the number of neurons of the input layer 61 in the neural network NN2 can be smaller than that in the neural network NN1.

The data 72 generated by the feature extraction unit 53 is input to the neural network NN2. The data 72 includes information on the coordinates of the extracted feature point.

As data input to the neural network NN2, data obtained by processing the data 72 may be used. For example, data obtained by performing calculation of a vector connecting given two feature points on all or some of the feature points may be used as data input to the neural network NN2. Moreover, data obtained by normalizing the calculated vectors may be used. Note that hereinafter, data obtained by processing the data 72 output from the neural network NN1 is also referred to as the data 72.

Data 73 is output from the neural network NN2 to which the data 72 is input. The data 73 corresponds to neuron values output from respective neurons of the output layer 63. Each neuron of the output layer 63 is associated with one emotion. As illustrated in FIG. 5B, the data 73 includes neuron values of the neurons each corresponding to a predetermined emotion (e.g., joy, pleasure, surprise, excitement, and hatred).

The neural network NN2 has learned so as to estimate the degree of each emotion from the data 72 and output the estimation as neuron values. The facial features of the user of the electronic device 10, such as a facial expression, can be determined by a relative positional relation between feature points of the user's face. Accordingly, the user's emotion can be estimated from the facial features by the neural network NN2.

Figure 5C:
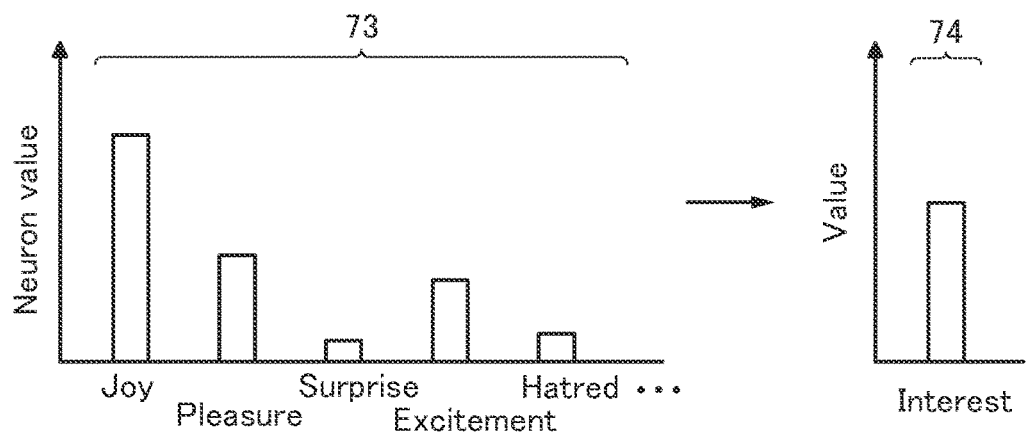
FIG. 5C is a graph showing emotion estimation.

FIG. 5C schematically illustrates the data 73. The level of a neuron value corresponding to each emotion indicates the level of an estimated emotion. From the level of the estimated emotion, the estimation unit 54 can estimate the level of another emotion. Data including the level of another emotion is referred to as data 74. FIG. 5C illustrates the case where the level of interest is estimated from the levels of emotions such as joy, pleasure, surprise, excitement, and hatred.

The level of interest, which is included in the data 74, can be estimated, for example, by inputting the levels of emotions such as joy, pleasure, surprise, excitement, and hatred, which are included in the data 73, to a predetermined formula. For example, the formula can be set so that the level of interest increases as the levels of joy, pleasure, surprise, and excitement are higher and the level of interest decreases as the level of hatred is higher.

Note that the degree of fatigue, physical condition, emotions, or the like can also be estimated without using a neural network. For example, estimation may be performed by a template matching method, where an image of part of the face of the user of the electronic device 10, which is obtained by the subject detection unit 52, is compared with a template image to use the degree of similarity therebetween. In that case, a structure without the feature extraction unit 53 can also be employed.

The information generation unit 55 has a function of determining or generating information to be presented to the user of the electronic device 10 on the basis of the degree of fatigue, physical condition, emotions, or the like, which is estimated by the estimation unit 54, and outputting the information to the information presentation unit 51. Accordingly, the information presentation unit 51 can present information corresponding to the information generated in the information generation unit 55.

For example, when the information presentation unit 51 has a function of displaying images, the information generation unit 55 can generate or select an image to be displayed and output the data thereon to the information presentation unit 51. When the information presentation unit 51 has a function of a lighting device, the information generation unit 55 can determine the brightness (illuminance) and chromaticity of lighting and output the data to the information presentation unit 51. When the information presentation unit 51 has a function of diffusing scent, the information generation unit 55 can determine the type or strength of scent to be diffused and output a signal for controlling the operation of the information presentation unit 51, for instance. When the information presentation unit 51 has a function of outputting a sound, the information generation unit 55 can generate or select a sound to be reproduced and output the data thereon as well as information on the volume level for reproduction to the information presentation unit 51. When the information presentation unit 51 has a function of producing a vibration, the information generation unit 55 can determine the pattern and intensity of the vibration and output a signal for controlling the operation of the information presentation unit 51, for instance.

The above is the description of the structure examples of the electronic device 10.

Note that the data 72 output from the feature extraction unit 53 may be directly input to the information generation unit 55 without being input to the estimation unit 54. For example, a facial expression itself of the user of the electronic device 10 can be detected by feature point detection with the feature extraction unit 53 without estimation by the estimation unit 54. In such a case, the data 72 output from the feature extraction unit 53 is directly input to the information generation unit 55, whereby power consumption of the electronic device 10 can be reduced.

Figure 6A:
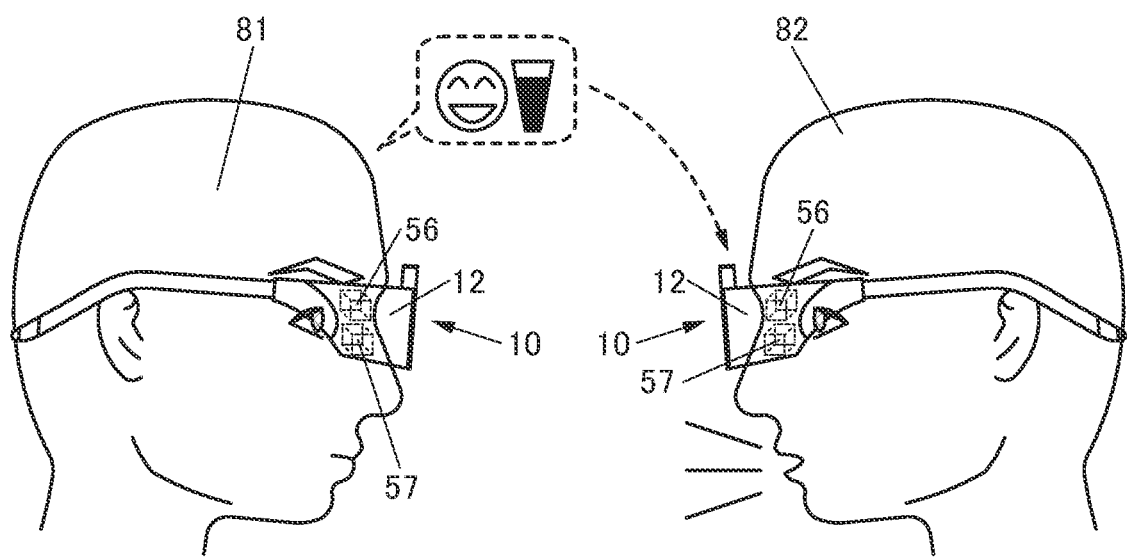
FIG. 6A illustrates a usage example of an electronic device.

FIG. 6A illustrates a usage example of the electronic device 10. In FIG. 6A, a user 81 of the electronic device 10 and a user 82 of another electronic device 10 have a conversation, and specifically, the user 82 talks to the user 81.

The electronic device 10 in FIG. 6A is configured with the electronic device 10a in FIG. 1A, a transmitter 56, and a receiver 57. Alternatively, the electronic device 10 may be configured with the electronic device 10b in FIG. 2A, the transmitter 56, and the receiver 57.

The transmitter 56 and the receiver 57 can be provided inside the housing 12. The transmitter 56 can be a wireless transmitter, and the receiver 57 can be a wireless receiver. Note that the transmitter 56 and the receiver 57 are not necessarily provided inside the housing 12. For example, the transmitter 56 and the receiver 57 may be provided outside the housing 12 so as to be in contact with the housing 12. Furthermore, the transmitter 56 and the receiver 57 may be an integrated device.

The transmitter 56 has a function of transmitting information generated by the information generation unit 55 to the outside of the electronic device 10. FIG. 6A illustrates the case where information generated by the information generation unit 55 is transmitted to another electronic device 10.

The receiver 57 has a function of receiving information from the outside of the electronic device 10. For example, the receiver 57 has a function of receiving information transmitted from the transmitter 56 of another electronic device 10. The received information can be displayed on the information presentation unit 51, for example.

In the case of FIG. 6A, the electronic device 10 used by the user 81 estimates what the user 81 feels when listening to what the user 82 says. For example, the electronic device 10 used by the user 81 estimates the level of interest in what the user 82 says. Information showing the level of interest of the user 81 is transmitted from the transmitter 56 of the electronic device 10 used by the user 81. The information transmitted from the transmitter 56 is received by the receiver 57 used by the user 82. The information received by the receiver 57 is presented by the information presentation unit 51.

Figure 6B:
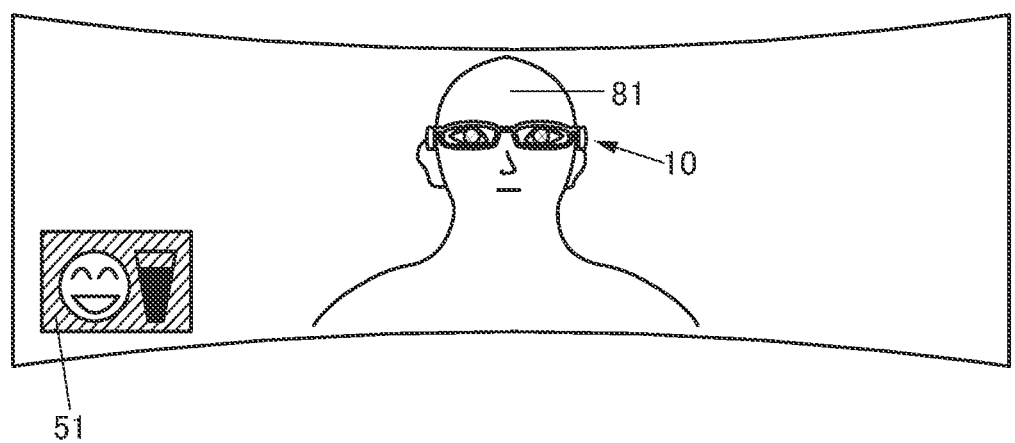
FIG. 6B illustrates an example of the field of view of a user of the electronic device.

FIG. 6B illustrates the field of view of the user 82. The field of view of the user 82 includes the information presentation unit 51 as well as the user 81. The information presentation unit 51 displays information received by the receiver 57 of the electronic device 10 used by the user 82, for example, the level of interest of the user 81. In this way, the user 82 finds the level of interest of the user 81. When the level of interest of the user 81 is low, for example, the user 82 can explore a topic that will interest the user 81 by changing topics. When the user 81 talks, the user 81 can learn the level of interest of the user 82.

Alternatively, the information presentation unit 51 of the electronic device 10 may display the degree of fatigue, physical condition, or the like of the user of another electronic device 10. In that case, the user of the electronic device 10 finds the degree of fatigue, physical condition, or the like of the user of another electronic device 10. Thus, for example, the user of the electronic device 10 can show concern for a person who is exhausted or feels ill and encourage them to rest, or can offer sound advice on health management.

Figure 7:
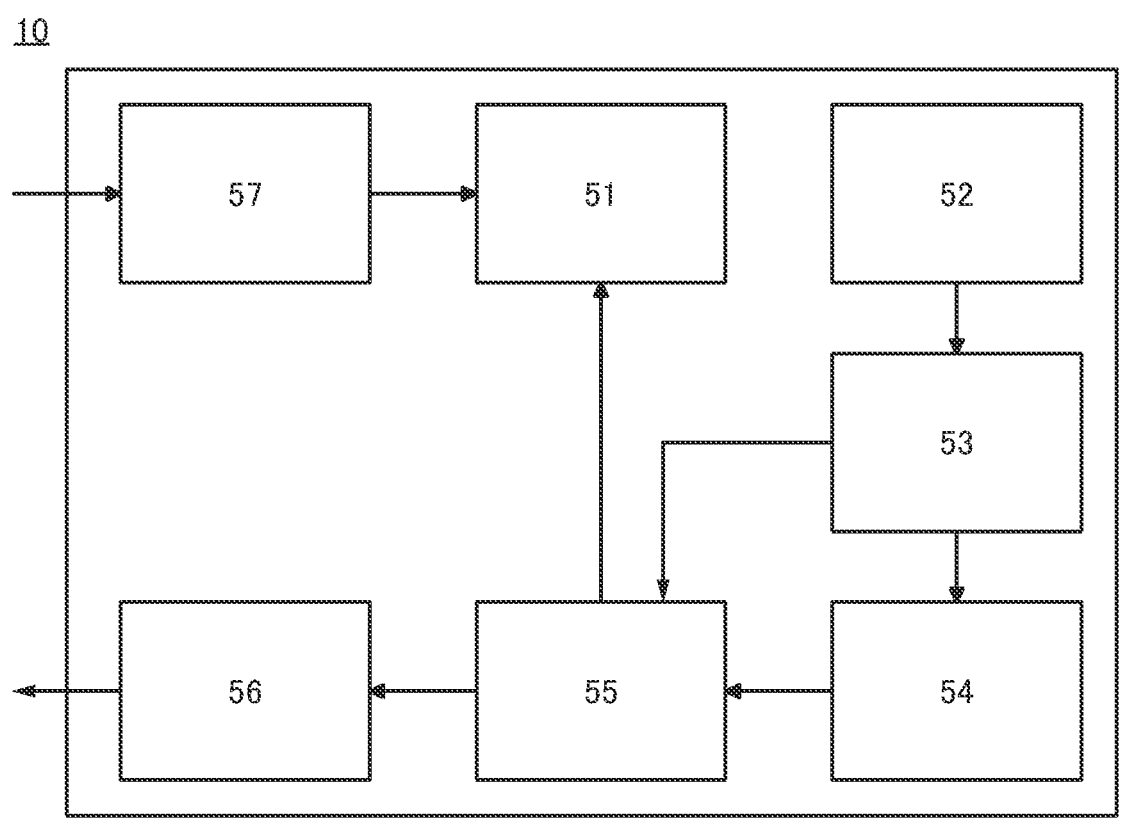
FIG. 7 is a block diagram illustrating a structure example of an electronic device.

FIG. 7 is a block diagram illustrating a structure example of the electronic device 10 in FIG. 6A, and shows a variation example of the structure in FIG. 4. The electronic device 10 with the structure in FIG. 7 is different from the electronic device 10 with the structure in FIG. 4 in including the transmitter 56 and the receiver 57.

As illustrated in FIG. 7, information generated by the information generation unit 55 is supplied to the transmitter 56. The information is transmitted to the outside of the electronic device 10 by the transmitter 56.

The receiver 57 receives information from the outside of the electronic device 10. For example, the receiver 57 can receive information transmitted from another electronic device 10. Alternatively, the receiver 57 can receive information transmitted from an electronic device other than the electronic device 10, or airwaves, for instance. The information received by the receiver 57 is presented by the information presentation unit 51. For example, an image corresponding to the information received by the receiver 57 can be displayed on a display region of the information presentation unit 51.

At least part of this embodiment can be implemented in combination with any of the other embodiments described in this specification as appropriate.

Embodiment 2

In this embodiment, a display device, a light source, an imaging device, and the like that can be used in the electronic device of one embodiment of the present invention will be described.

<Structure Example 1 of Display Device>

Figure 8:
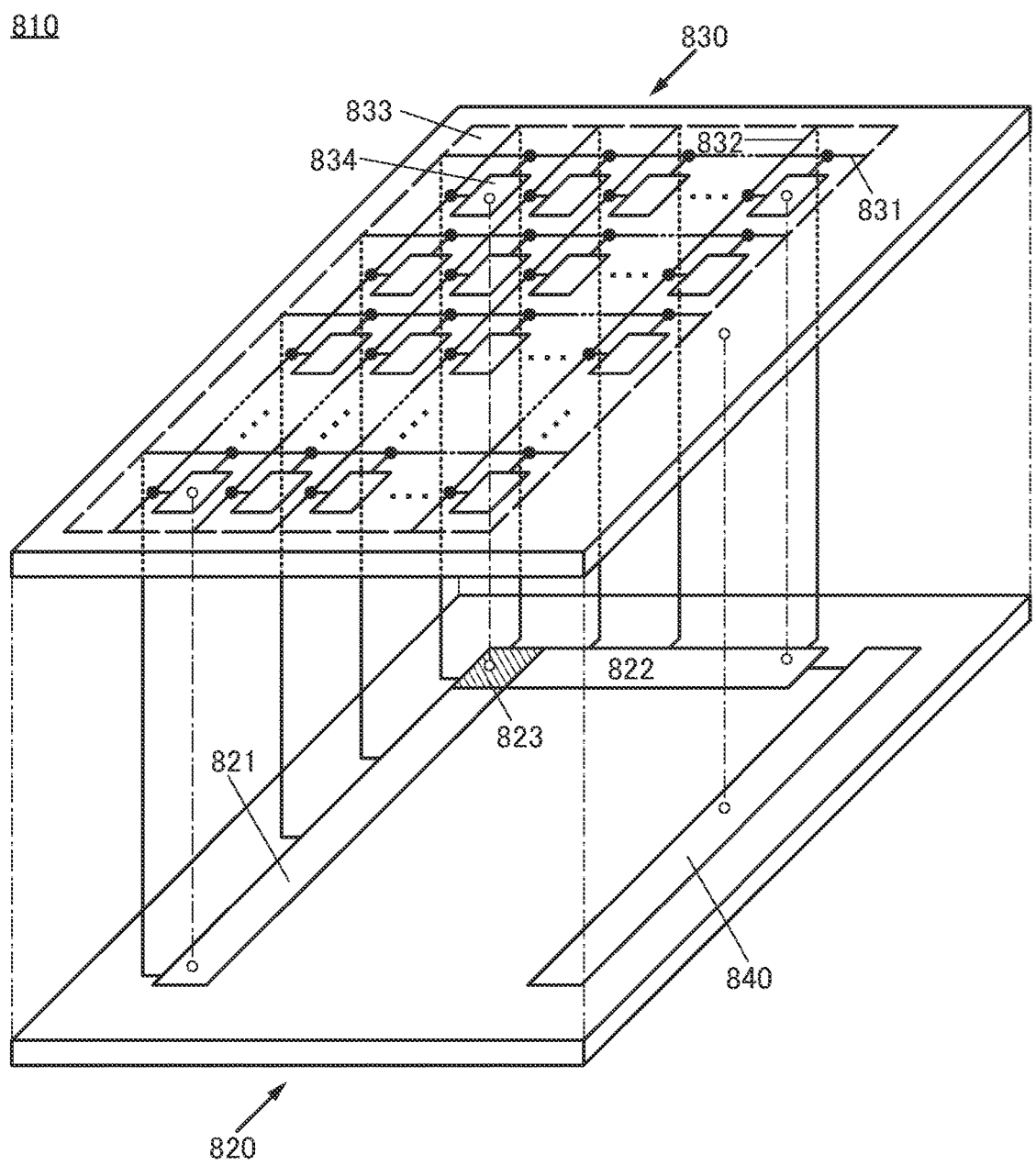
FIG. 8 is a block diagram illustrating a structure example of a display device.

FIG. 8 is a block diagram illustrating a structure example of a display device 810 of one embodiment of the present invention. The display device 810 includes a layer 820 and a layer 830 stacked over the layer 820. The layer 820 includes a gate driver circuit 821, a source driver circuit 822, and a circuit 840. The layer 830 includes pixels 834, and the pixels 834 are arranged in a matrix to form a pixel array 833. An interlayer insulator can be provided between the layer 820 and the layer 830. Note that the layer 820 may be stacked over the layer 830.

The circuit 840 is electrically connected to the source driver circuit 822. Note that the circuit 840 may be electrically connected to another circuit or the like.

The pixels 834 in the same row are electrically connected to the gate driver circuit 821 through a wiring 831, and the pixels 834 in the same column are electrically connected to the source driver circuit 822 through a wiring 832. The wiring 831 functions as a scan line, and the wiring 832 functions as a data line.

Although FIG. 8 illustrates the structure in which the pixels 834 in one row are electrically connected through one wiring 831 and the pixels 834 in one column are electrically connected through one wiring 832, one embodiment of the present invention is not limited thereto. For example, the pixels 834 in one row may be electrically connected through two or more wirings 831, or the pixels 834 in one column may be electrically connected through two or more wirings 832. That is, for example, one pixel 834 may be electrically connected to two or more scan lines or two or more data lines. Alternatively, for example, one wiring 831 may be electrically connected to the pixels 834 in two or more rows, or one wiring 832 may be connected to the pixels 834 in two or more columns. That is, for example, one wiring 831 may be shared by the pixels 834 in two or more rows, or one wiring 832 may be shared by the pixels 834 in two or more columns.

The gate driver circuit 821 has a function of generating a signal for controlling the operation of the pixel 834 and supplying the signal to the pixel 834 through the wiring 831. The source driver circuit 822 has a function of generating an image signal and supplying the signal to the pixel 834 through the wiring 832. The circuit 840 has a function of receiving image data that serves as a base for an image signal generated by the source driver circuit 822 and supplying the received image data to the source driver circuit 822, for example. The circuit 840 also has a function of a control circuit that generates a start pulse signal, a clock signal, and the like. In addition, the circuit 840 can have a function that the gate driver circuit 821 and the source driver circuit 822 do not have.

The pixel array 833 has a function of displaying an image corresponding to image signals supplied to the pixels 834 from the source driver circuit 822. Specifically, light with luminance corresponding to the image signals is emitted from the pixels 834, whereby an image is displayed on the pixel array 833.

In FIG. 8, the positional relation between the layer 820 and the layer 830 is represented by dashed-dotted lines and blank circles; the blank circle of the layer 820 and the blank circle of the layer 830 that are connected by the dashed-dotted line overlap with each other. Note that the same representation is used in other diagrams.

In the display device 810, the gate driver circuit 821 and the source driver circuit 822, which are provided in the layer 820, each include a region overlapping with the pixel array 833. For example, the gate driver circuit 821 and the source driver circuit 822 each include a region overlapping with some of the pixels 834. Stacking the gate driver circuit 821 and the source driver circuit 822 with the pixel array 833 to have an overlap region allows the display device 810 to have a narrower frame and a smaller size.

The gate driver circuit 821 and the source driver circuit 822 have an overlap region where they are not strictly separated from each other. The region is referred to as a region 823. With the region 823, the area occupied by the gate driver circuit 821 and the source driver circuit 822 can be reduced. Accordingly, even when the area of the pixel array 833 is small, the gate driver circuit 821 and the source driver circuit 822 can be provided without extending beyond the pixel array 833. Alternatively, the area of the region where the gate driver circuit 821 and the source driver circuit 822 do not overlap with the pixel array 833 can be reduced. In the above manner, the frame and size of the display device 810 can be further reduced, compared to the structure without the region 823.

The circuit 840 can be provided not to overlap with the pixel array 833. Note that the circuit 840 may be provided to have a region overlapping with the pixel array 833.

Figure 9:
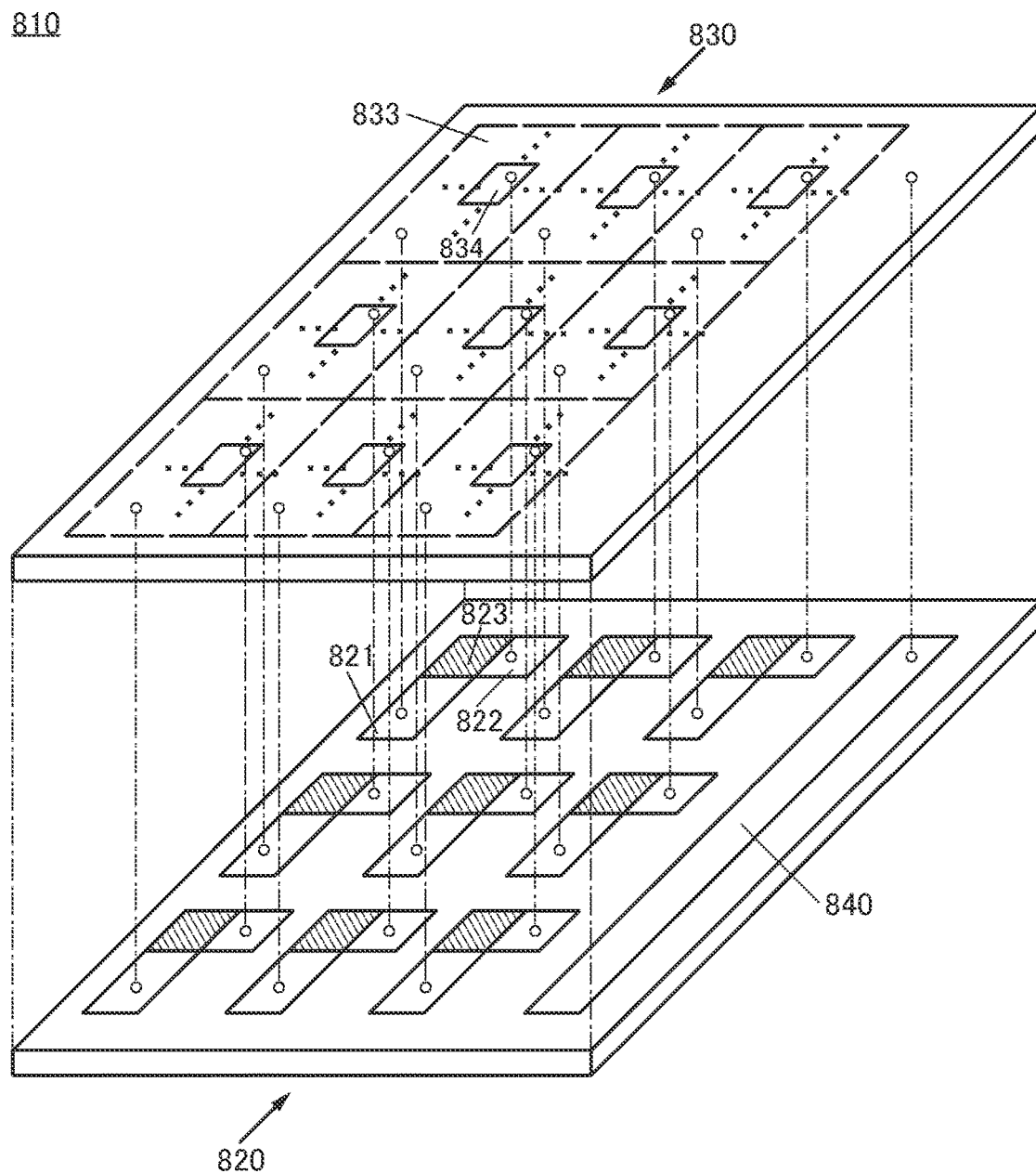
FIG. 9 is a block diagram illustrating a structure example of a display device.

Although FIG. 8 illustrates a structure example in which one gate driver circuit 821 and one source driver circuit 822 are provided in the layer 820 and one pixel array 833 is provided in the layer 830, a plurality of pixel arrays 833 may be provided in the layer 830. That is, the pixel array provided in the layer 830 may be divided. FIG. 9 illustrates a variation example of the structure in FIG. 8, and shows a structure example of the display device 810 in which pixel arrays 833 of three rows by three columns are provided in the layer 830. Note that the layer 830 may include pixel arrays 833 of two rows by two columns, or pixel arrays 833 of four or more rows by four or more columns. The number of rows and the number of columns of pixel arrays 833 provided in the layer 830 may be different from each other. In the display device 810 having the structure illustrated in FIG. 9, one image can be displayed using all the pixel arrays 833, for example.

Although the wirings 831 and 832 are omitted for simplicity in FIG. 9, the wirings 831 and 832 are actually provided in the display device 810 having the structure illustrated in FIG. 9. In addition, although the electrical connection relation of the circuit 840 is not illustrated in FIG. 9, the circuit 840 is actually electrically connected to the source driver circuit 822. Note that as in FIG. 9, some components may be omitted in other diagrams.

In the layer 820, the gate driver circuits 821 as many as the pixel arrays 833 and the source driver circuits 822 as many as the pixel arrays 833 can be provided, for example. In that case, each of the gate driver circuits 821 can be provided to overlap with the corresponding pixel array 833 including the pixel 834 to which the gate driver circuit 821 supplies a signal. Moreover, each of the source driver circuits 822 can be provided to overlap with the corresponding pixel array 833 including the pixel 834 to which the source driver circuit 822 supplies an image signal.

When a plurality of pixel arrays 833 are provided and a plurality of gate driver circuits 821 and source driver circuits 822 are provided accordingly, the number of pixels 834 provided in one pixel array 833 can be reduced. A plurality of gate driver circuits 821 can be operated in parallel and a plurality of source driver circuits 822 can be operated in parallel; hence, the time required for writing image signals corresponding to a one-frame image to the pixels 834 can be shortened, for example. Thus, the length of one frame period can be shortened, and the display device 810 can operate at higher speed. Therefore, the number of pixels 834 included in the display device 810 can be increased, resulting in a higher definition of the display device 810. In addition, the definition of an image that can be displayed by the display device of one embodiment of the present invention can be higher than the definition of an image that can be displayed by a display device in which a gate driver circuit and a source driver circuit do not overlap with a pixel array. Furthermore, the clock frequency can be lowered, so that power consumption of the display device 810 can be reduced.

With a structure where a gate driver circuit and a source driver circuit do not overlap with a pixel array, the gate driver circuit and the source driver circuit are provided in a portion around the pixel array, for example. In this case, it is difficult to provide pixel arrays of more than two rows and more than two columns in terms of positions where source driver circuits would be provided, for example. In contrast, in the display device 810, the gate driver circuit and the source driver circuit can be provided in a layer different from the layer including the pixel array, thereby having a region overlapping with the pixel array; hence, pixel arrays of more than two rows and more than two columns can be provided as illustrated in FIG. 9. In other words, five or more gate driver circuits and five or more source driver circuits can be provided in the display device 810.

As described above, the display device 810 can operate at higher speed, for example, than a display device in which a gate driver circuit and a source driver circuit do not overlap with a pixel array. Thus, the definition of the display device 810 can be higher than that of the display device in which the gate driver circuit and the source driver circuit do not overlap with the pixel array. For example, the pixel density of the display device 810 can be 1000 ppi or higher, 5000 ppi or higher, or 10000 ppi or higher. Consequently, the display device 810 can display high-quality images with little graininess and highly realistic images.

The resolution of an image that can be displayed by the display device 810 can be higher than that of an image that can be displayed by the display device in which the gate driver circuit and the source driver circuit do not overlap with the pixel array. For example, the display device 810 can display images with a resolution of 4K2K, 8K4K, or higher. Moreover, the size of the display device 810 can be reduced. For example, the size of a display region of the display device 810 can be 8 inches or less.

Note that even in the structure where a plurality of source driver circuits 822 and the like are provided in the layer 820 and a plurality of pixel arrays 833 are provided in the layer 830, the number of circuits 840 provided in the display device 810 can be one as in the structure illustrated FIG. 8. As illustrated in FIG. 9, the circuit 840 can be provided not to overlap with any of the pixel arrays 833. Note that the circuit 840 may be provided to have a region overlapping with any of the pixel arrays 833.

Figure 10:
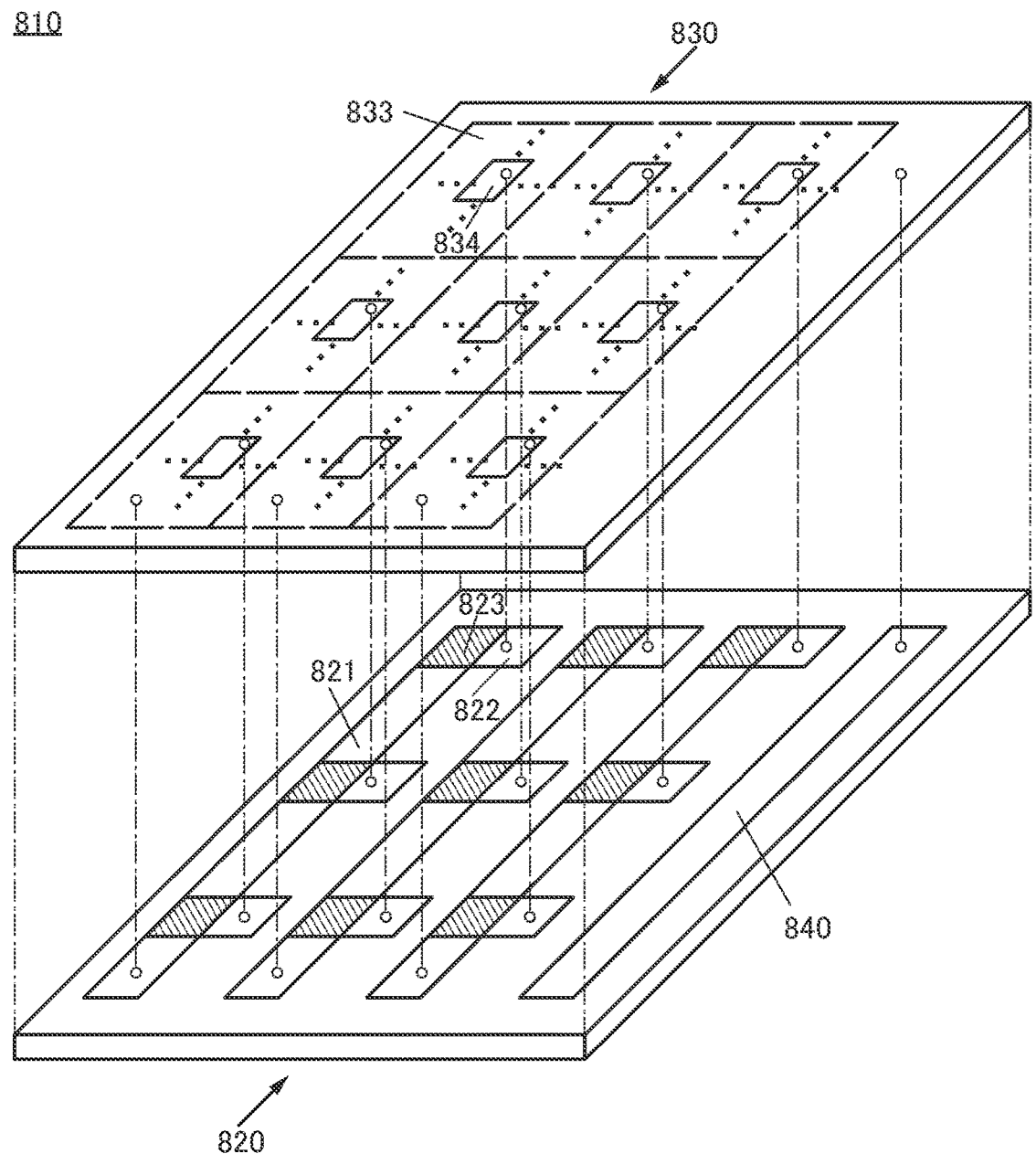
FIG. 10 is a block diagram illustrating a structure example of a display device.

Although FIG. 9 illustrates the structure example in which the number of gate driver circuits 821 is the same as the number of pixel arrays 833, one embodiment of the present invention is not limited thereto. FIG. 10 illustrates a variation example of the structure in FIG. 9, and shows a structure example of the display device 810 in which the number of gate driver circuits 821 is the same as the number of columns of the pixel arrays 833. In the display device 810 with the structure illustrated in FIG. 10, three gate driver circuits 821 are provided to correspond to pixel arrays 833 of three columns In addition, pixel arrays 833 of three rows are provided, and the pixel arrays 833 of three rows and one column share one gate driver circuit 821.

Figure 11:
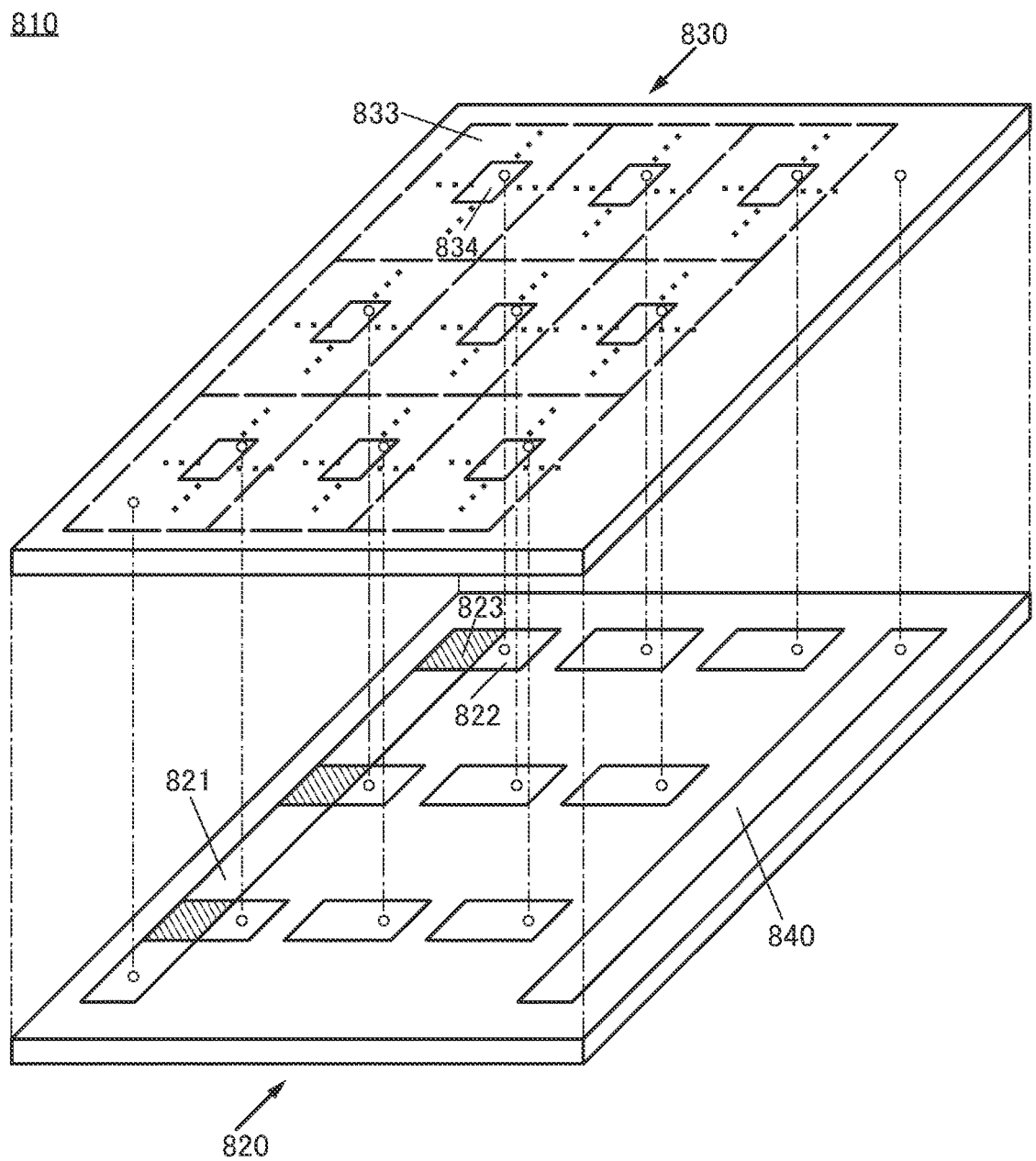
FIG. 11 is a block diagram illustrating a structure example of a display device.

FIG. 11 illustrates a variation example of the structure in FIG. 9, and shows a structure example of the display device 810 including a plurality of pixel arrays 833 and one gate driver circuit 821. In the display device 810 with the structure illustrated in FIG. 11, pixel arrays 833 of three rows and three columns share one gate driver circuit 821. Note that in the display device 810 with the structure in FIG. 11, the gate driver circuit 821 can be provided not to overlap with the pixel array 833.

Although not illustrated, the number of source driver circuits 822 is not necessarily the same as the number of pixel arrays 833. The number of source driver circuits 822 in the display device 810 may be larger than or smaller than the number of pixel arrays 833 in the display device 810.

Figure 12:
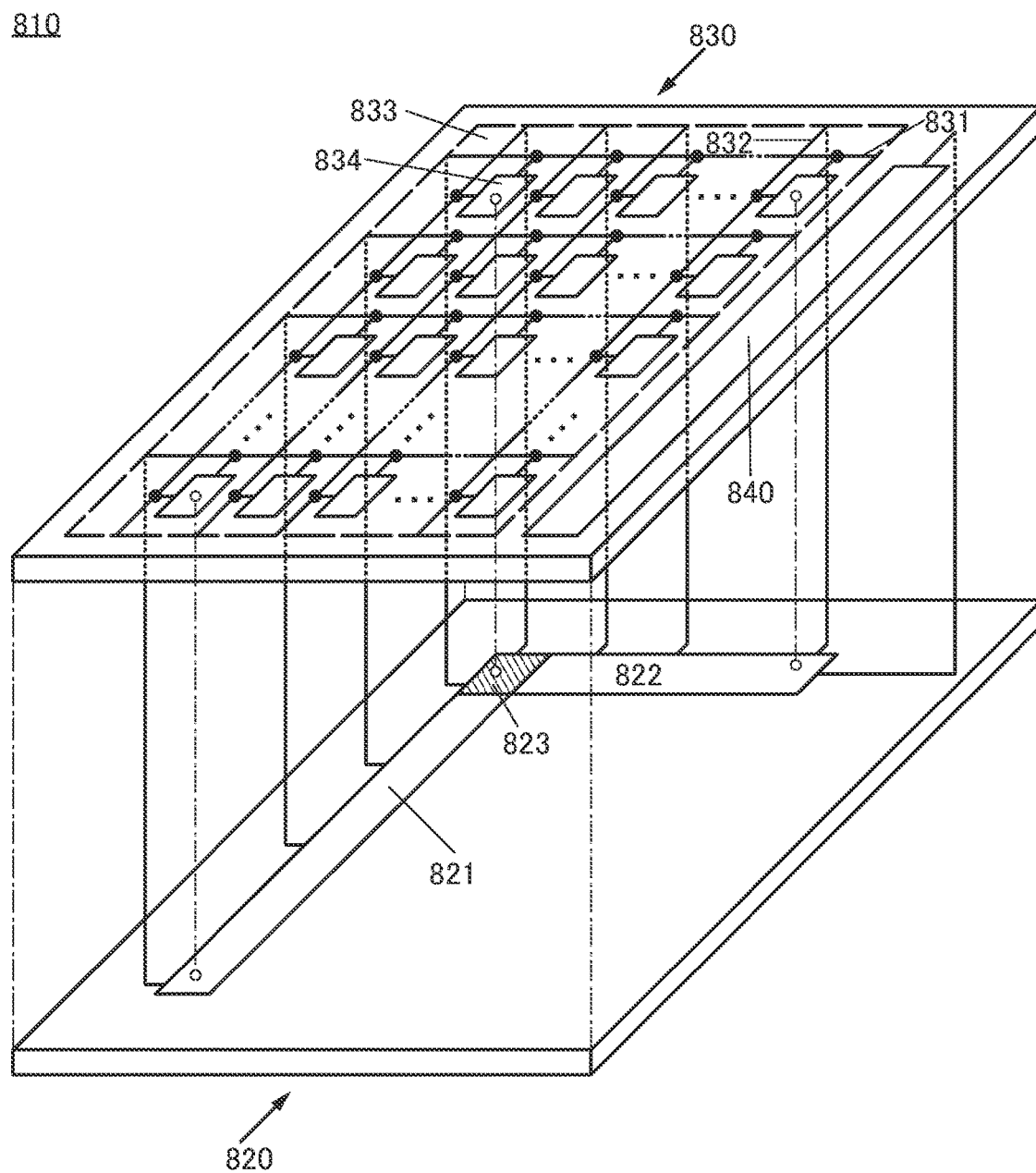
FIG. 12 is a block diagram illustrating a structure example of a display device.

Although FIG. 8 illustrates the structure example in which the circuit 840 is provided in the layer 820, the circuit 840 is not necessarily provided in the layer 820. FIG. 12 illustrates a variation example of the structure in FIG. 8 and shows a structure example of the display device 810 in which the circuit 840 is provided in the layer 830. Note that the components of the circuit 840 may be provided in both the layer 820 and the layer 830.

Figure 13:
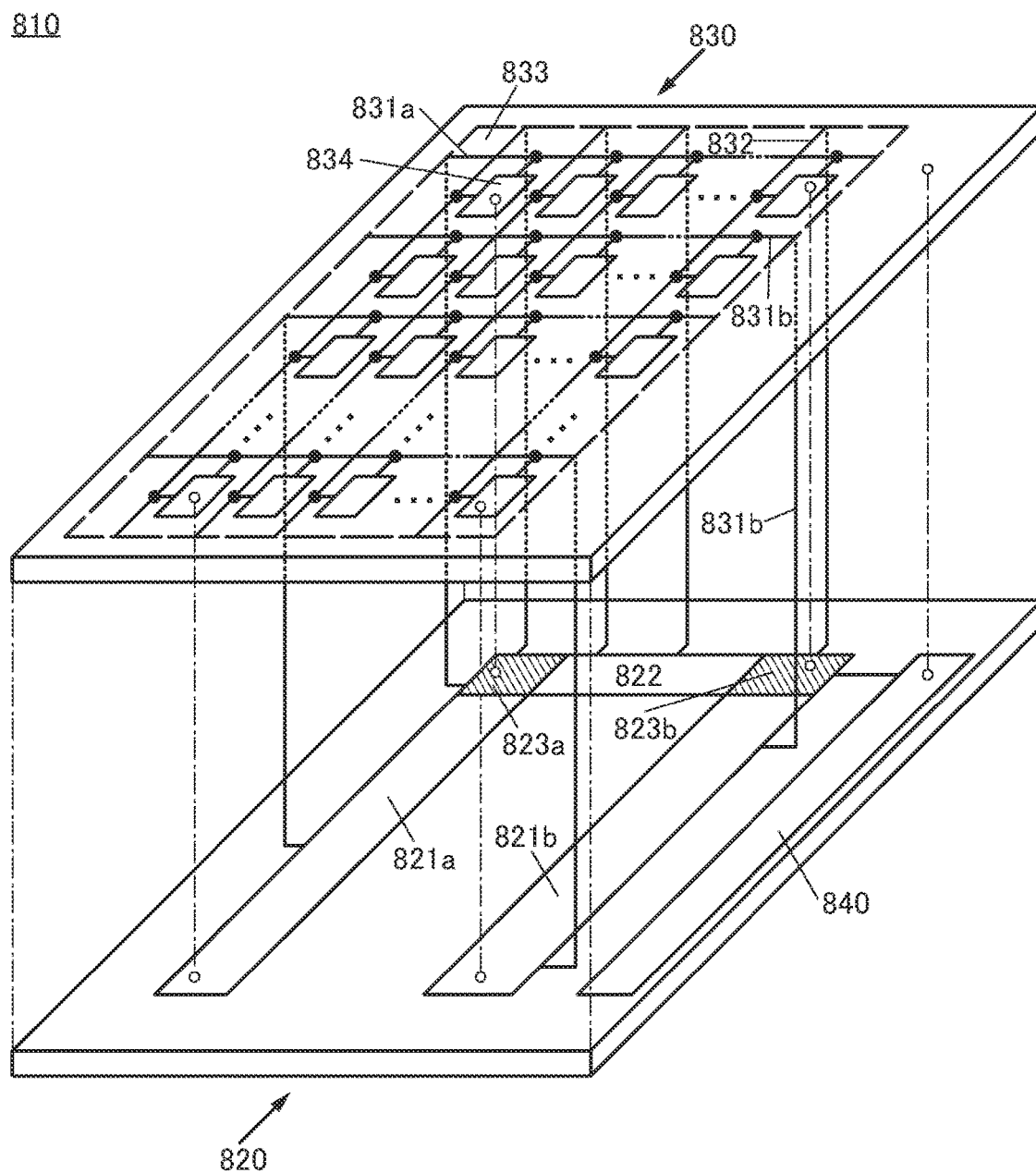
FIG. 13 is a block diagram illustrating a structure example of a display device.

Although FIG. 8 illustrates the structure example including one pixel array 833 and one gate driver circuit, the number of gate driver circuits may be larger than that of pixel arrays 833. FIG. 13 illustrates a variation example of the structure in FIG. 8, and shows a structure example of the display device 810 in which two gate driver circuits (a gate driver circuit 821*a* and a gate driver circuit 821*b*) are provided for one pixel array 833.

In the display device 810 having the structure illustrated in FIG. 13, the pixels 834 in an odd-numbered row are electrically connected to the gate driver circuit 821*a* through a wiring 831*a*, and the pixels 834 in an even-numbered row are electrically connected to the gate driver circuit 821*b* through a wiring 831*b*. The wiring 831*a* and the wiring 831*b* function as scan lines like the wiring 831.

The gate driver circuit 821*a* has a function of generating a signal for controlling the operation of the pixel 834 in the odd-numbered row and supplying the signal to the pixel 834 through the wiring 831*a*. The gate driver circuit 821*b* has a function of generating a signal for controlling the operation of the pixel 834 in the even-numbered row and supplying the signal to the pixel 834 through the wiring 831*b*.

Like the gate driver circuit 821, each of the gate driver circuits 821*a* and 821*b* includes a region overlapping with the pixel array 833. For example, each of the gate driver circuits 821*a* and 821*b* includes a region overlapping with some of the pixels 834, like the gate driver circuit 821. The gate driver circuit 821*a* includes a region 823*a* where the gate driver circuit 821*a* overlaps with the source driver circuit 822 without being strictly separated from the source driver circuit 822. The gate driver circuit 821*b* includes a region 823*b* where the gate driver circuit 821*b* overlaps with the source driver circuit 822 without being strictly separated from the source driver circuit 822.

In the display device 810 having the structure illustrated in FIG. 13, the gate driver circuit 821*a* can operate to write image signals to all the pixels 834 in the odd-numbered rows, and then the gate driver circuit 821*b* can operate to write image signals to all the pixels 834 in the even-numbered rows. That is, the display device 810 having the structure illustrated in FIG. 13 can operate by an interlace method. With an interlace method, the operating speed of the display device 810 can be increased and the frame frequency can be increased. In addition, the number of pixels 834 to which image signals are written in one frame period can be half that when the display device 810 operates by a progressive method. Thus, in the display device 810, the clock frequency can be lower in interlace driving than in progressive driving; hence, power consumption of the display device 810 can be reduced.

Figure 14:
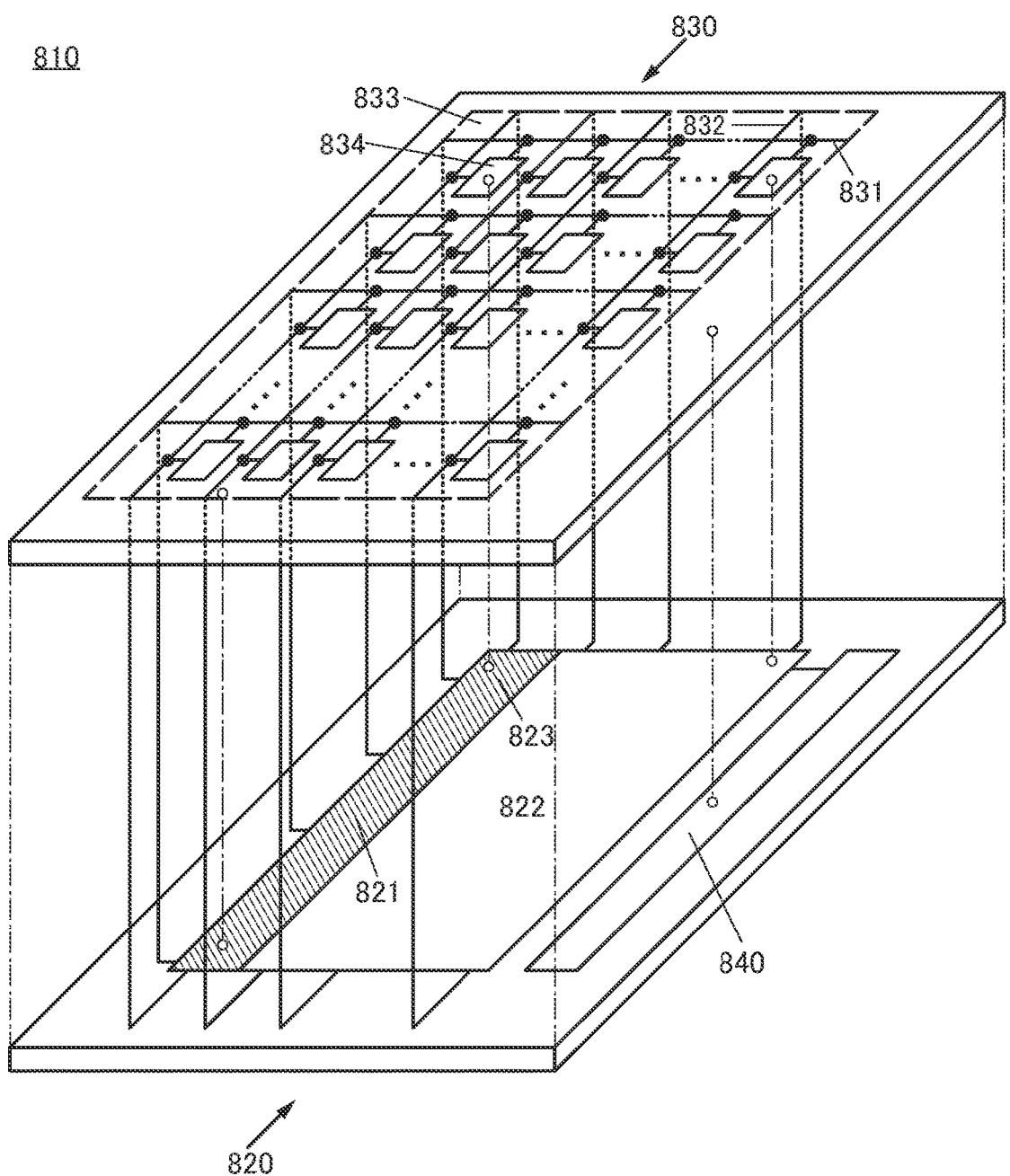
FIG. 14 is a block diagram illustrating a structure example of a display device.

Although FIG. 8 illustrates the structure example in which only one end of the wiring 832 is connected to the source driver circuit 822, a plurality of portions of the wiring 832 may be connected to the source driver circuit 822. FIG. 14 illustrates a structure example of the display device 810 in which the source driver circuit 822 is connected to both ends of the wiring 832. When a plurality of portions of the wiring 832 are connected to the source driver circuit 822, signal delay due to wiring resistance, parasitic capacitance, and the like can be inhibited, for example. This increases the operating speed of the display device 810.

Note that not only both ends of the wirings 832 but also another portion of the wiring 832 may be connected to the source driver circuit 822. For example, a center portion of the wiring 832 may be connected to the source driver circuit 822. By increasing the number of portions where the wiring 832 and the source driver circuit 822 are connected, signal delay and the like can be further inhibited and the operating speed of the display device 810 can be further increased. Alternatively, for example, a structure may be employed in which one end and a center portion of the wiring 832 are connected to the source driver circuit 822 and the other end of the wiring 832 is not connected to the source driver circuit 822.

When one source driver circuit 822 is connected to a plurality of portions of the wiring 832, the area occupied by the source driver circuit 822 increases as illustrated in FIG. 14. Even in that case, the source driver circuit 822 is stacked to have a region overlapping with the pixel array 833, which can inhibit an increase in size of the display device 810. FIG. 14 shows that the entire gate driver circuit 821 overlaps with the source driver circuit 822 without being strictly separated from the source driver circuit 822; however, even when one source driver circuit 822 is connected to a plurality of portions of the wiring 832, only part of the gate driver circuit 821 may overlap with the source driver circuit 822.

Note that a plurality of portions of the wiring 831 may be connected to one gate driver circuit 821; thus, signal delay or the like can be inhibited, and the operating speed of the display device 810 can be increased. Such a structure increases the area occupied by the gate driver circuit 821 as in the case of employing the source driver circuit 822 in FIG. 14; however, the gate driver circuit 821 is stacked to have a region overlapping with the pixel array 833, which can prevent an increase in size of the display device 810.

The structures of the display device 810 that are illustrated in FIGS. 8 to 14 can be combined as appropriate. For example, the structure in FIG. 9 can be combined with the structure in FIG. 13. In this case, the display device 810 can include, for example, a plurality of pixel arrays 833, gate driver circuits twice as many as the pixel arrays 833, and source driver circuits 822 as many as the pixel arrays 833.

<Structure Example of Circuit 840 and Source Driver Circuit 822>

Figure 15:
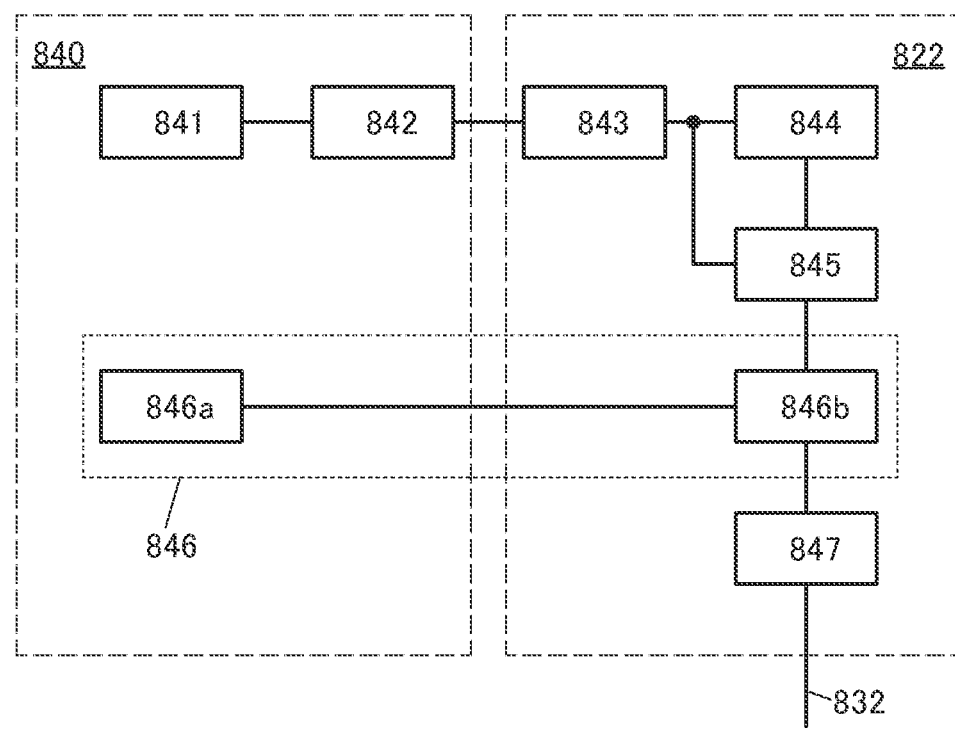
FIG. 15 is a block diagram illustrating a structure example of a display device.

FIG. 15 is a block diagram illustrating a structure example of the circuit 840 and the source driver circuit 822. Although FIG. 15 illustrates only one source driver circuit 822, the circuit 840 can be electrically connected to a plurality of source driver circuits 822.

The circuit 840 includes a receiver circuit 841, a serial-to-parallel converter circuit 842, and a potential generator circuit 846*a*. The source driver circuit 822 includes a buffer circuit 843, a shift register circuit 844, a latch circuit 845, a pass transistor logic circuit 846*b*, and an amplifier circuit 847. Here, the potential generator circuit 846*a* and the pass transistor logic circuit 846*b* constitute a digital-to-analog converter circuit (hereinafter D/A converter circuit) 846.

The receiver circuit 841 is electrically connected to the serial-to-parallel converter circuit 842. The serial-to-parallel converter circuit 842 is electrically connected to the buffer circuit 843. The buffer circuit 843 is electrically connected to the shift register circuit 844 and the latch circuit 845. The shift register circuit 844 is electrically connected to the latch circuit 845. The latch circuit 845 and the potential generator circuit 846*a* are electrically connected to the pass transistor logic circuit 846*b*. The pass transistor logic circuit 846*b* is electrically connected to an input terminal of the amplifier circuit 847. An output terminal of the amplifier circuit 847 is electrically connected to the wiring 832.

The receiver circuit 841 has a function of receiving image data that serves as a base for an image signal generated by the source driver circuit 822. The image data can be single-ended image data. When the receiver circuit 841 receives image data with the use of a data transmitting signal based on low voltage differential signaling (LVDS) or the like, the receiver circuit 841 may have a function of converting the received signal into a signal based on a standard that can undergo internal processing.

The serial-to-parallel converter circuit 842 has a function of performing parallel conversion of single-ended image data output from the receiver circuit 841. Providing the serial-to-parallel converter circuit 842 in the circuit 840 allows image data and the like to be transmitted from the circuit 840 to the source driver circuit 822 and the like even if a load at that time is large.

The buffer circuit 843 can be a unity gain buffer, for example. The buffer circuit 843 has a function of outputting data identical to image data output from the serial-to-parallel converter circuit 842. With the buffer circuit 843 provided in the source driver circuit 822, even if a potential corresponding to image data output from the serial-to-parallel converter circuit 842 is lowered by wiring resistance or the like when being transmitted from the circuit 840 to the source driver circuit 822, a potential corresponding to the decrease amount can be recovered. Accordingly, the decrease in driving capability of the source driver circuit 822 and the like can be inhibited even if the load is large at the time of transmitting image data and the like from the circuit 840 to the source driver circuit 822 and the like.

The shift register circuit 844 has a function of generating a signal for controlling the operation of the latch circuit 845. The latch circuit 845 has a function of holding or outputting image data output from the buffer circuit 843. Whether the latch circuit 845 holds or outputs image data is selected in accordance with a signal supplied from the shift register circuit 844.

The D/A converter circuit 846 has a function of converting digital image data, which is output from the latch circuit 845, into an analog image signal. The potential generator circuit 846*a* has a function of generating potentials that correspond to the number of bits of image data capable of being subjected to D/A conversion and supplying the potentials to the pass transistor logic circuit 846*b*. For example, when the D/A converter circuit 846 has a function of converting 8-bit image data into an analog image signal, the potential generator circuit 846*a* can generate 256 potentials with different levels.

The pass transistor logic circuit 846*b* has a function of receiving image data from the latch circuit 845 and outputting any of the potentials generated by the potential generator circuit 846*a* on the basis of the digital value of the received image data. For example, a potential output from the pass transistor logic circuit 846*b* can be higher as the digital value of image data is higher. The potential output from the pass transistor logic circuit 846*b* can be used as an image signal.

As illustrated in FIG. 15, in the display device 810, the circuits constituting the D/A converter circuit 846 can be provided in both the source driver circuit 822 and the circuit 840. Specifically, a circuit that is preferably provided in each source driver circuit (e.g., the pass transistor logic circuit 846*b*) can be provided in the source driver circuit 822, and a circuit that is not necessarily provided in each source driver circuit (e.g., the potential generator circuit 846*a*) can be provided in the circuit 840. In that case, the area occupied by the source driver circuit 822 can be reduced as compared with the case where all circuits constituting the D/A converter circuit 846 are provided in the source driver circuit 822, for example; hence, the number of source driver circuits 822 provided in the layer 820 can be increased. Thus, the number of pixel arrays 833 provided in the layer 830 can be increased, and it is possible to achieve high speed operation, low power consumption, and high definition of the display device 810, for example, as well as high resolution of images that the display device 810 can display. Here, the components of a circuit other than the D/A converter circuit 846 can also be provided in both the source driver circuit 822 and the circuit 840.

When the circuits constituting the D/A converter circuit 846 are provided in both the source driver circuit 822 and the circuit 840 as illustrated in FIG. 15, the display device 810 can include one potential generator circuit 846*a* and pass transistor logic circuits 846*b* as many as the source driver circuits 822.

The amplifier circuit 847 has a function of amplifying an image signal output from the pass transistor logic circuit 846*b* and outputting the amplified signal to the wiring 832 functioning as a data line. Providing the amplifier circuit 847 allows an image signal to be supplied to the pixel 834 stably. As the amplifier circuit 847, a voltage follower circuit including an operational amplifier and the like can be used, for example. Note that in the case where a circuit including a differential input circuit is used as the amplifier circuit, the offset voltage of the differential input circuit is preferably set as close to 0 V as possible.

In the circuit 840, a variety of circuits can be provided in addition to the receiver circuit 841, the serial-to-parallel converter circuit 842, and the potential generator circuit 846*a*. For example, the circuit 840 can include a control circuit having a function of generating a start pulse signal, a clock signal, and the like.

<Configuration Example of D/A Converter Circuit 846>

Figure 16:
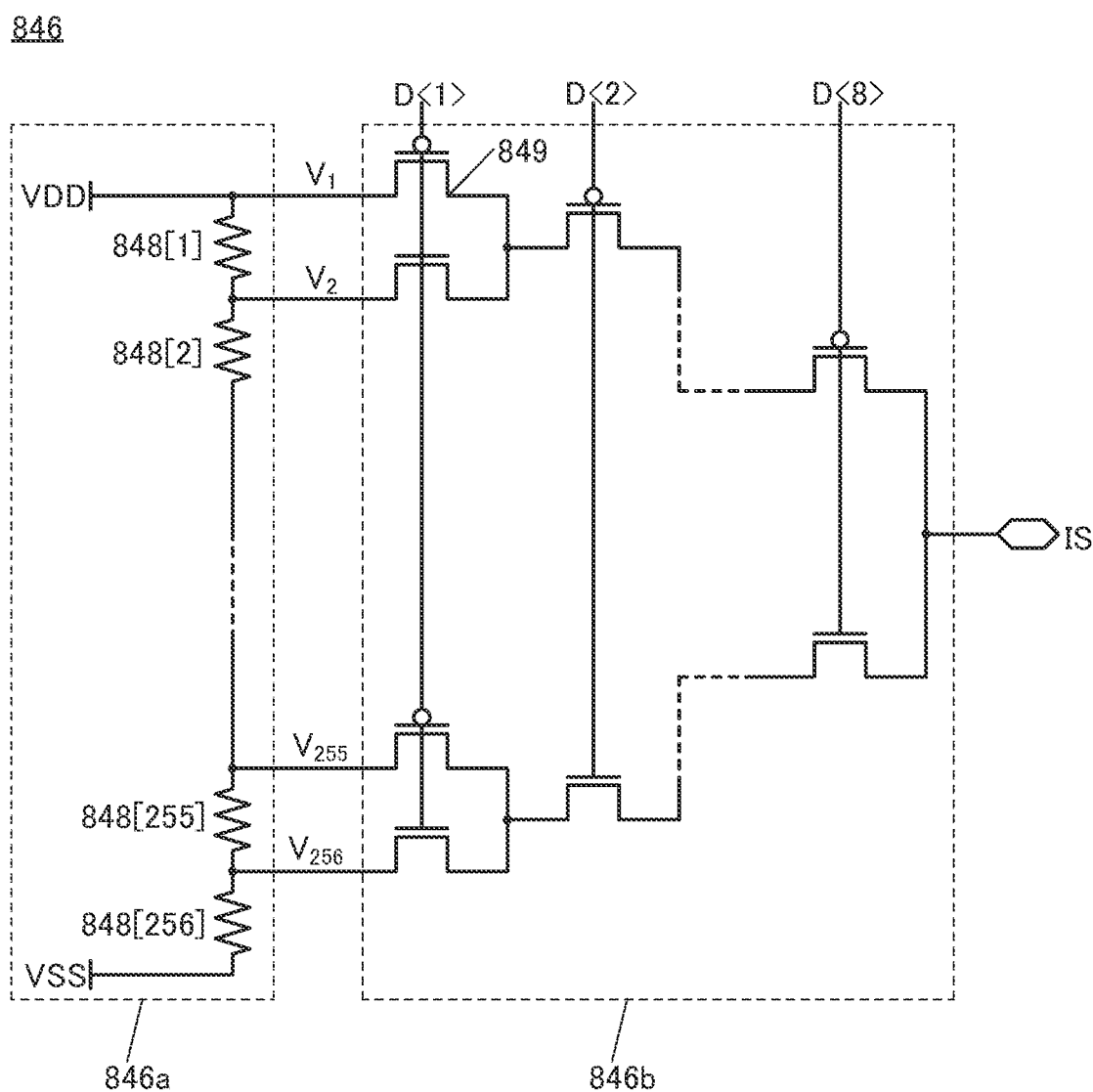
FIG. 16 is a circuit diagram illustrating a configuration example of a D/A converter circuit.

FIG. 16 is a circuit diagram illustrating a configuration example of the potential generator circuit 846*a* and the pass transistor logic circuit 846*b*, which constitute the D/A converter circuit 846. The D/A converter circuit 846 having the configuration illustrated in FIG. 16 is capable of converting 8-bit image data D<1> to D<8> into an analog image signal IS.

In this specification and the like, for example, first-bit image data D is denoted as the image data D<1>, second-bit image data D as the image data D<2>, and eighth-bit image data D as the image data D<8>.

The potential generator circuit 846*a* having the configuration in FIG. 16 includes resistors 848[1] to 848[256] that are connected in series. In other words, the D/A converter circuit 846 can be a resistor-string D/A converter circuit.

A potential VDD can be supplied to one terminal of the resistor 848[1]. A potential VSS can be supplied to one terminal of the resistor 848[256]. Thus, potentials $V_1$ to $V_{256}$ that have different levels can be output from the terminals of the resistors 848[1] to 848[256]. Although FIG. 16 illustrates a configuration example of the potential generator circuit 846*a* in which the potential $V_1$ is the potential VDD, the potential $V_{256}$ may be the potential VSS. Alternatively, the potential $V_1$ may be the potential VDD and the potential $V_{256}$ may be the potential VSS without providing the resistor 848[256].

In this specification and the like, the potential VDD can be a high potential and the potential VSS can be a low potential, for example. Here, the low potential can be a ground potential, for example. The high potential is a potential higher than the low potential, and can be a positive potential when the low potential is a ground potential.

The pass transistor logic circuit 846*b* having the configuration in FIG. 16 is formed of 8-stage pass transistors 849. Specifically, the pass transistor logic circuit 846*b* has a structure in which one stage is separated into two electrical paths; i.e., the pass transistor logic circuit 846*b* has a total of 256 paths. That is, the pass transistors 849 can be regarded as being electrically connected in a tournament manner. The analog image signal IS can be output from one of a source and a drain of the pass transistor 849 in the eighth stage, which is the last stage.

For example, the image data D<1> can be supplied to the pass transistor 849 in the first stage, the image data D<2> can be supplied to the pass transistors 849 in the second stage, and the image data D<8> can be supplied to the pass transistors 849 in the eighth stage. In this manner, the potential of the image signal IS can be set to any of the potentials $V_1$ to $V_{256}$ in accordance with the image data D. Consequently, digital image data can be converted into the analog image signal IS.

The pass transistor logic circuit 846*b* in FIG. 16 includes n-channel pass transistors 849 and p-channel pass transistors 849; alternatively, the pass transistor logic circuit 846*b* can include only re-channel pass transistors 849. The pass transistors 849 provided in the pass transistor logic circuit 846b can be all n-channel transistors when the image data D<1> to D<8> and their complementary data are supplied to the gates of the pass transistors 849, for example.

The configuration illustrated in FIG. 16 can also be applied to the D/A converter circuit 846 having a function of performing D/A conversion on the image data D with bits other than 8 bits. For example, when 1024 or 1023 resistors 848 are provided in the potential generator circuit 846a and 10-stage pass transistors 849 are provided in the pass transistor logic circuit 846b, the D/A converter circuit 846 can have a function of performing D/A conversion on 10-bit image data D.

<Configuration Example of Gate Driver Circuit 821>

Figure 17:
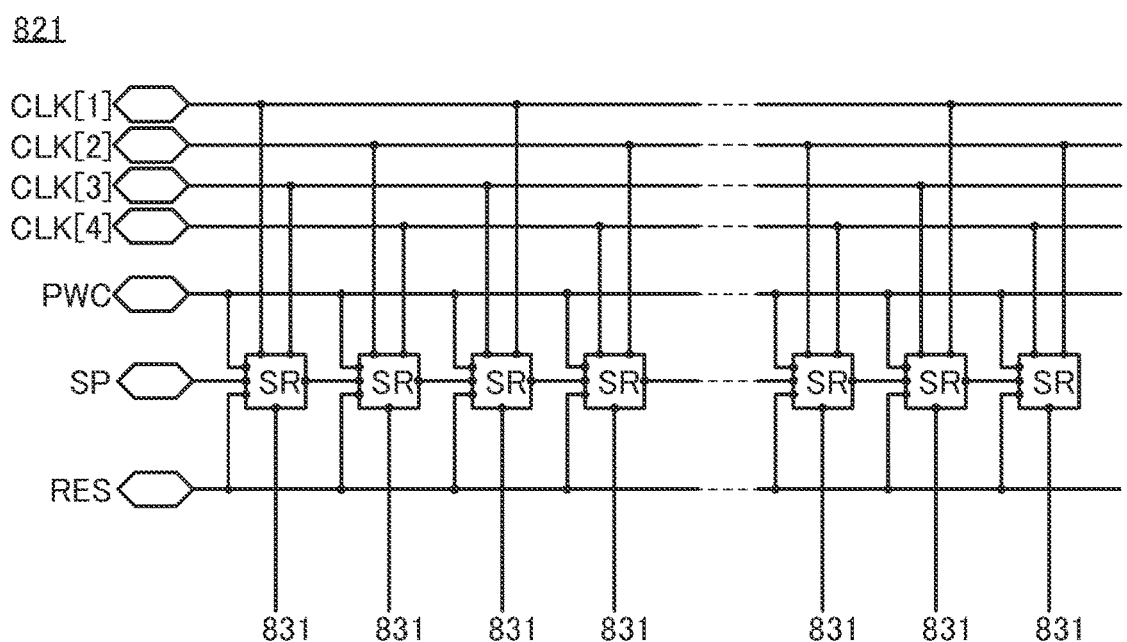
FIG. 17 is a block diagram illustrating a configuration example of a shift register.

FIG. 17 is a block diagram illustrating a configuration example of the gate driver circuit 821. The gate driver circuit 821 includes shift register circuits SR composed of a plurality of set-reset flip-flops. The shift register circuit SR is electrically connected to the wiring 831 having a function of a scan line, and has a function of outputting a signal to the wiring 831.

A signal RES is reset signal. When the signal RES is set to a high potential, for example, all the outputs of the shift register circuits SR can be a low potential. A signal SP is a start pulse signal. When the signal SP is input to the gate driver circuit 821, the shift operation of the shift register circuits SR can be started. A signal PWC is a pulse width control signal and has a function of controlling the pulse width of a signal output from the shift register circuit SR to the wiring 831. A signal CLK[1], a signal CLK[2], a signal CLK[3], and a signal CLK[4] are clock signals. For example, two of the signals CLK[1] to CLK[4] can be input to one shift register circuit SR.

Note that the configuration illustrated in FIG. 17 can be applied to the shift register circuit 844 included in the source driver circuit 822 when the wiring 831 electrically connected to the shift register circuit SR is replaced with another wiring, for example.

Figure 18A:
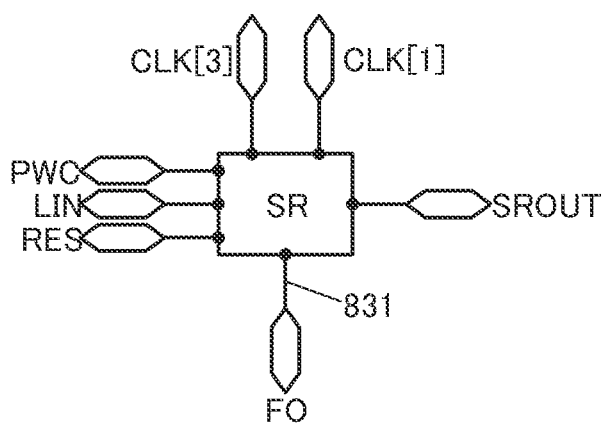
FIG. 18A is a block diagram illustrating a structure example of a shift register.

FIG. 18A illustrates signals input to the shift register circuit SR and signals output from the shift register circuit SR. Here, FIG. 18A illustrates the case where the signal CLK[1] and the signal CLK[3] are input as the clock signals.

A signal FO is an output signal and is output to the wiring 831, for example. A signal SROUT is a shift signal and can be used as a signal LIN that is input to the next-stage shift register circuit SR. Among the signals illustrated in FIG. 18A, the signal RES, the signal PWC, the signal CLK[1], the signal CLK[3], and the signal LIN are input to the shift register circuit SR; the signal FO and the signal SROUT are output from the shift register circuit SR.

Figure 18B:
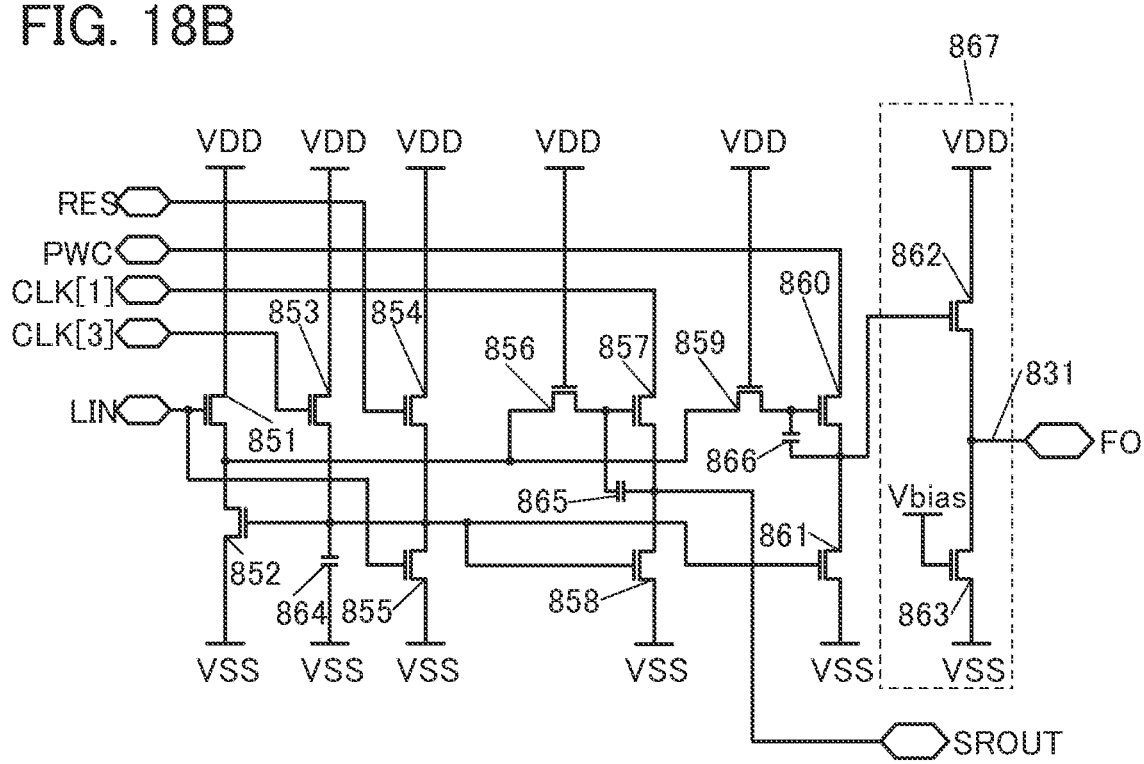
FIG. 18B is a circuit diagram illustrating a configuration example of the shift register.

FIG. 18B is a circuit diagram illustrating a configuration example of the shift register circuit SR that inputs and outputs the signals illustrated in FIG. 18A. The shift register circuit SR includes transistors 851 to 863 and capacitors 864 to 866.

One of a source and a drain of the transistor 851 is electrically connected to one of a source and a drain of the transistor 852, one of a source and a drain of the transistor 856, and one of a source and a drain of the transistor 859. A gate of the transistor 852 is electrically connected to one of a source and a drain of the transistor 853, one of a source and a drain of the transistor 854, one of a source and a drain of the transistor 855, a gate of the transistor 858, a gate of the transistor 861, and one electrode of the capacitor 864. The other of the source and the drain of the transistor 856 is electrically connected to a gate of the transistor 857 and one electrode of the capacitor 865. The other of the source and the drain of the transistor 859 is electrically connected to a gate of the transistor 860 and one electrode of the capacitor 866. One of a source and a drain of the transistor 860 is electrically connected to one of a source and a drain of the transistor 861, a gate of the transistor 862, and the other electrode of the capacitor 866.

The signal LIN is input to a gate of the transistor 851 and a gate of the transistor 855. The signal CLK[3] is input to a gate of the transistor 853. The signal RES is input to a gate of the transistor 854. The signal CLK[1] is input to one of a source and a drain of the transistor 857. The signal PWC is input to the other of the source and the drain of the transistor 860.

One of a source and a drain of the transistor 862 and one of a source and a drain of the transistor 863 are electrically connected to the wiring 831, and the signal FO is output from the wiring 831 as described above. The signal SROUT is output from the other of the source and the drain of the transistor 857, one of a source and a drain of the transistor 858, and the other electrode of the capacitor 865.

The potential VDD is supplied to the other of the source and the drain of the transistor 851, the other of the source and the drain of the transistor 853, the other of the source and the drain of the transistor 854, a gate of the transistor 856, a gate of the transistor 859, and other of the source and drain of the transistor 862. The potential VSS is supplied to the other of the source and the drain of the transistor 852, the other of the source and the drain of the transistor 855, the other of the source and the drain of the transistor 858, the other of the source and the drain of the transistor 861, the other of the source and the drain of the transistor 863, and the other electrode of the capacitor 864.

The transistor 863 is a bias transistor and has a function of a constant current source. A potential Vbias that is a bias potential can be supplied to a gate of the transistor 863.

The transistor 862 and the transistor 863 form a source follower circuit 867. Even if signal decay or the like due to wiring resistance, parasitic capacitance, or the like occurs inside the register circuit SR, the source follower circuit 867 in the shift register circuit SR can prevent the potential of the signal FO from being lowered by the signal decay or the like. This increases the operating speed of the display device 810. Note that the source follower circuit 867 may be replaced with another circuit as long as the circuit has a function of a buffer.

<Structure Example of Region 823>

Figure 19:
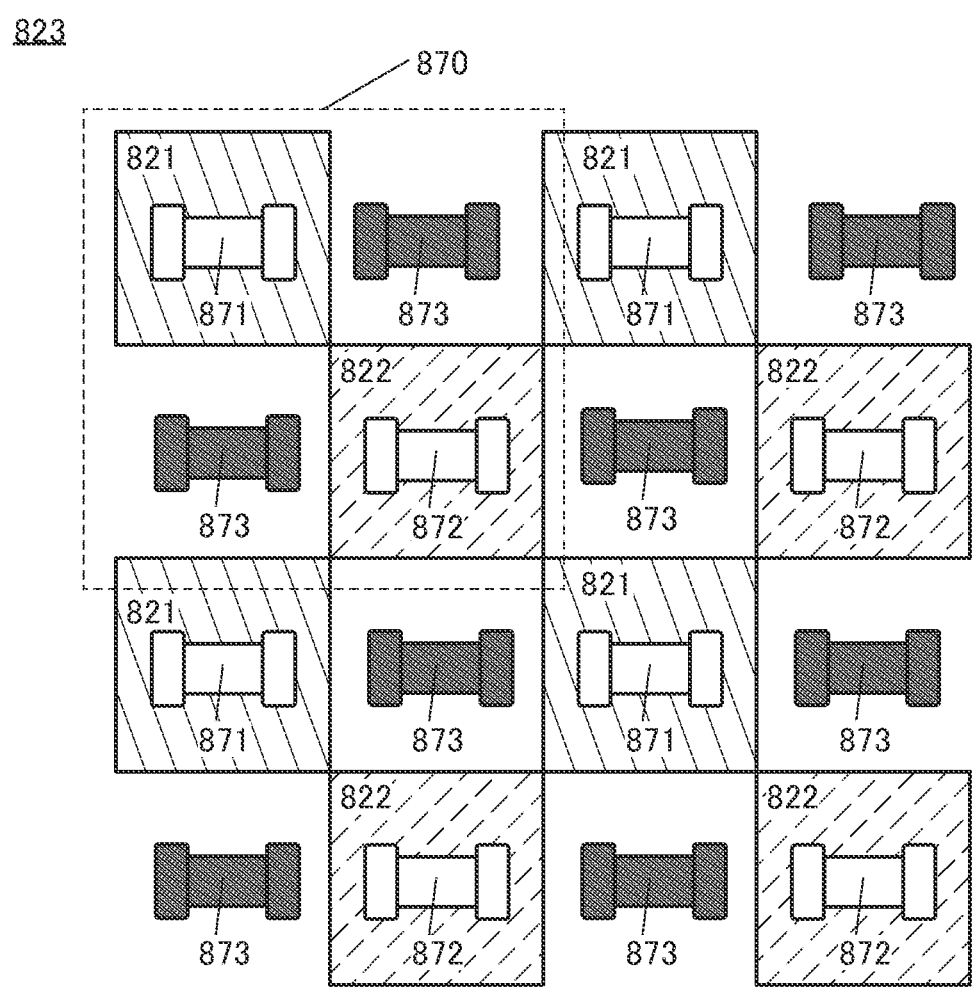
FIG. 19 is a schematic diagram illustrating an arrangement example of a gate driver circuit and a source driver circuit.

FIG. 19 illustrates a structure example of the region 823, where the gate driver circuit 821 and the source driver circuit 822 overlap with each other. As illustrated in FIG. 19, regions including a component of the gate driver circuit 821 and regions including a component of the source driver circuit 822 are arranged in a certain regular pattern in the region 823. FIG. 19 shows a transistor 871 as a component of the gate driver circuit 821, and a transistor 872 as a component of the source driver circuit 822.

FIG. 19 illustrates the case where the regions including the component of the gate driver circuit 821 are provided in the first row and the third row, and the regions including the component of the source driver circuit 822 are provided in the second row and the fourth row. In the region 823, a dummy element is provided between the regions including the component of the gate driver circuit 821. A dummy element is provided between the regions including the component of the source driver circuit 822. FIG. 19 illustrates a structure example of the region 823 in which four dummy transistors 873 as dummy elements are provided around each of the transistors 871 and 872.

When the dummy elements such as the dummy transistors 873 are provided in the region 823, the dummy elements can absorb impurities and inhibit diffusion of impurities into the transistors 871 and 872 and the like. Thus, the reliability of the transistors 871 and 872 and the like can be increased, leading to higher reliability of the display device 810. Although the transistors 871, the transistors 872, and the dummy transistors 873 are arranged in a matrix in FIG. 19, they are not necessarily arranged in a matrix.

Figure 20:
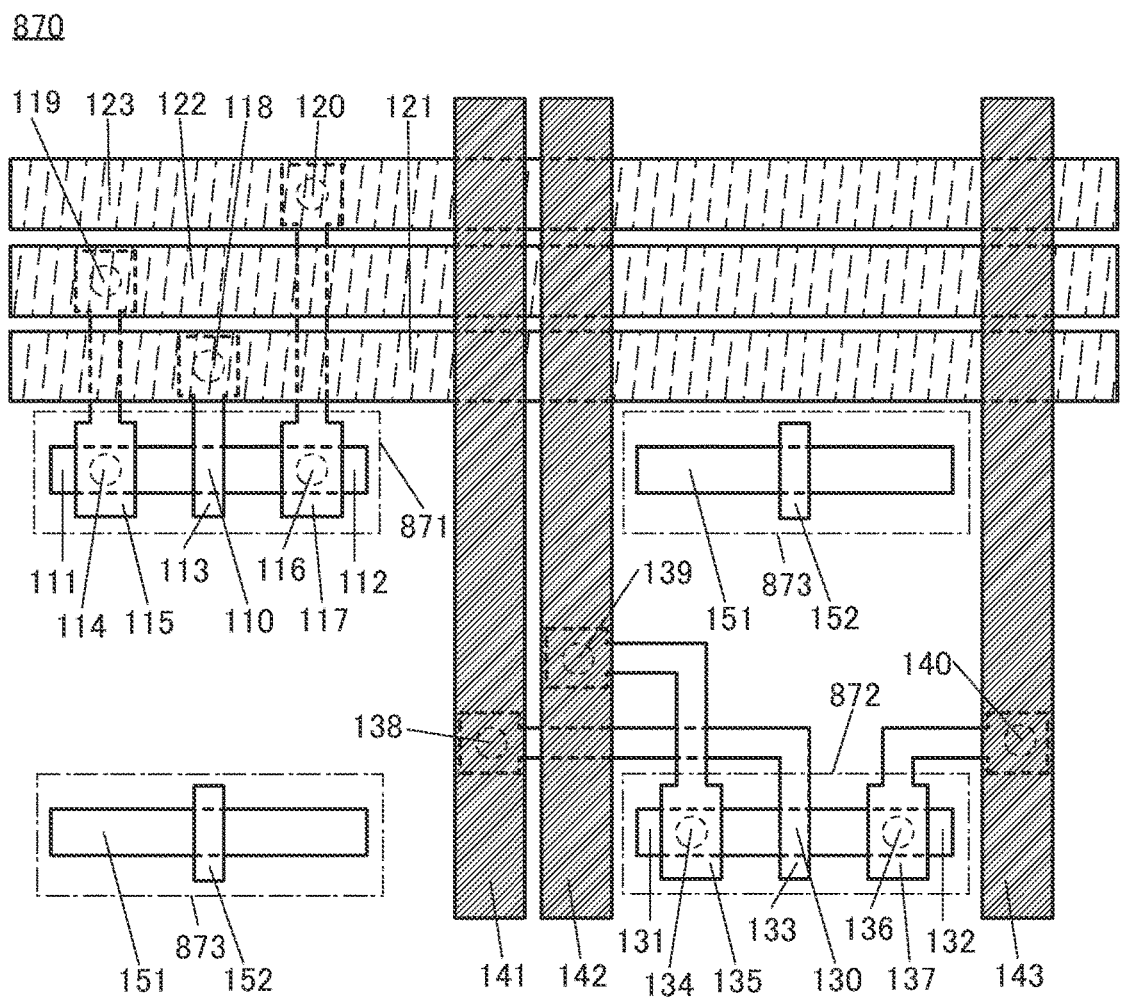
FIG. 20 is a top view illustrating a structure example of a gate driver circuit and a source driver circuit.

FIG. 20 is a top view illustrating a structure example of a region 870 that is part of the region 823. As illustrated in FIG. 19 and FIG. 20, one transistor 871, one transistor 872, and two dummy transistors 873 are provided in the region 870. As illustrated in FIG. 20, the transistor 871 includes a channel formation region 110, a source region 111, and a drain region 112. The transistor 871 also includes a gate electrode 113 that has a region overlapping with the channel formation region 110.

Note that components such as a gate insulator are not illustrated in FIG. 20. The channel formation region, the source region, and the drain region are not illustrated as clearly separated regions in FIG. 20.

An opening 114 is provided in the source region 111, and the source region 111 is electrically connected to a wiring 115 through the opening 114. An opening 116 is provided in the drain region 112, and the drain region 112 is electrically connected to a wiring 117 through the opening 116.

An opening 118 is provided in the gate electrode 113, and the gate electrode 113 is electrically connected to a wiring 121 through the opening 118. An opening 119 is provided in the wiring 115, and the wiring 115 is electrically connected to a wiring 122 through the opening 119. An opening 120 is provided in the wiring 117, and the wiring 117 is electrically connected to a wiring 123 through the opening 120. In other words, the source region 111 is electrically connected to the wiring 122 through the wiring 115, and the drain region 112 is electrically connected to the wiring 123 through the wiring 117.

The transistor 872 includes a channel formation region 130, a source region 131, and a drain region 132. The transistor 872 also includes a gate electrode 133 that has a region overlapping with the channel formation region 130.

An opening 134 is provided in the source region 131, and the source region 131 is electrically connected to a wiring 135 through the opening 134. An opening 136 is provided in the drain region 132, and the drain region 132 is electrically connected to a wiring 137 through the opening 136.

An opening 138 is provided in the gate electrode 133, and the gate electrode 133 is electrically connected to a wiring 141 through the opening 138. An opening 139 is provided in the wiring 135, and the wiring 135 is electrically connected to a wiring 142 through the opening 139. An opening 140 is provided in the wiring 137, and the wiring 137 is electrically connected to a wiring 143 through the opening 140. In other words, the source region 131 is electrically connected to the wiring 142 through the wiring 135, and the drain region 132 is electrically connected to the wiring 143 through the wiring 137.

Note that the channel formation region 110 and the channel formation region 130 can be provided in one layer. The source region 111 and the drain region 112 can be provided in the same layer as the source region 131 and the drain region 132. The gate electrode 113 and the gate electrode 133 can be provided in one layer. The wirings 115 and 117 and the wirings 135 and 137 can be provided in one layer. That is, the transistor 871 and the transistor 872 can be provided in one layer. Consequently, the manufacturing process of the display device 810 can be simpler than the case where the transistor 871 and the transistor 872 are provided in different layers, making the display device 810 inexpensive.

The wirings 121 to 123 electrically connected to the transistor 871 included in the gate driver circuit 821 are provided in one layer. The wirings 141 to 143 electrically connected to the transistor 872 included in the source driver circuit 822 are provided in one layer. The wirings 121 to 123 are provided in a layer different from the layer where the wirings 141 to 143 are provided. In the above manner, an electrical short circuit between the transistor 871, which is the component of the gate driver circuit 821, and the transistor 872, which is the component of the source driver circuit 822, can be inhibited. Accordingly, a malfunction of the gate driver circuit 821 and the source driver circuit 822 can be inhibited even when the gate driver circuit 821 and the source driver circuit 822 are not strictly separated from each other and have an overlap region. As a result, the reliability of the display device 810 can be increased.

In this specification and the like, the expression "the same layer as A" means a layer that is formed in the same step as A and contains the same material as A, for example.

Although FIG. 20 illustrates a structure in which the wirings 141 to 143 are provided above the wirings 121 to 123, the wirings 141 to 143 may be provided below the wirings 121 to 123.

Although FIG. 20 illustrates a structure in which the wirings 121 to 123 extend in the horizontal direction and the wirings 141 to 143 extend in the perpendicular direction, one embodiment of the present invention is not limited thereto. For example, the wirings 121 to 123 may extend in the perpendicular direction, and the wirings 141 to 143 may extend in the horizontal direction. Alternatively, the wirings 121 to 123 and the wirings 141 to 143 may all extend in the horizontal direction or in the perpendicular direction.

The dummy transistor 873 includes a semiconductor 151 and a conductor 152. The conductor 152 includes a region overlapping with the semiconductor 151. The semiconductor 151 can be formed in the same layer as the channel formation regions of the transistor 871 and the transistor 872. The conductor 152 can be formed in the same layer as the gate electrodes of the transistor 871 and the transistor 872. Note that one of the semiconductor 151 and the conductor 152 may be omitted in the dummy transistor 873.

The semiconductor 151 and the conductor 152 can be electrically isolated from other wirings or the like. A constant potential may be supplied to the semiconductor 151 and/or the conductor 152. For example, a ground potential may be supplied.

<Structure Example of Pixel 834>

Figure 21A:
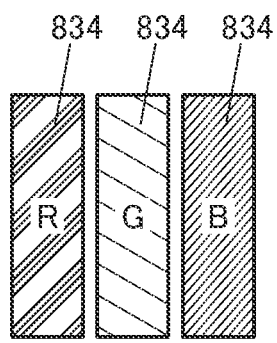
FIGS. 21A to 21G illustrate structure examples of pixels.
Figure 21B:
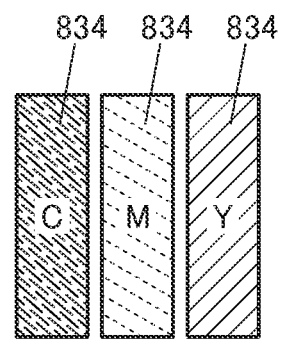

FIGS. 21A to 21E are diagrams for describing colors exhibited by the pixels 834 provided in the display device 810. As illustrated in FIG. 21A, the display device 810 can include the pixel 834 having a function of emitting red light (R), the pixel 834 having a function of emitting green light (G), and the pixel 834 having a function of emitting blue light (B). Alternatively, as illustrated in FIG. 21B, the display device 810 may include the pixel 834 having a function of emitting cyan light (C), the pixel 834 having a function of emitting magenta light (M), and the pixel 834 having a function of emitting yellow light (Y).

Figure 21C:
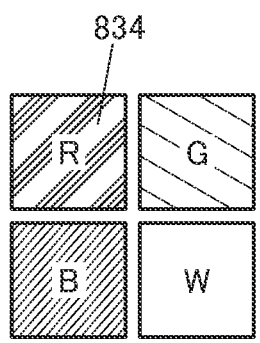
Figure 21D:
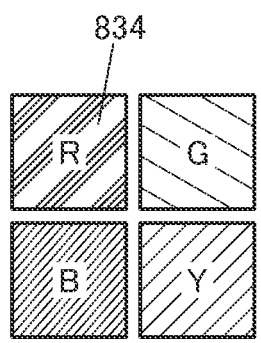

Alternatively, as illustrated in FIG. 21C, the display device 810 may include the pixel 834 having a function of emitting red light (R), the pixel 834 having a function of emitting green light (G), the pixel 834 having a function of emitting blue light (B), and the pixel 834 having a function of emitting white light (W). Alternatively, as illustrated in FIG. 21D, the display device 810 may include the pixel 834 having a function of emitting red light (R), the pixel 834 having a function of emitting green light (G), the pixel 834 having a function of emitting blue light (B), and the pixel 834 having a function of emitting yellow light (Y). Alternatively, as illustrated in FIG. 21E, the display device 810 may include the pixel 834 having a function of emitting cyan light (C), the pixel 834 having a function of emitting magenta light (M), the pixel 834 having a function of emitting yellow light (Y), and the pixel 834 having a function of emitting white light (W).

Figure 21E:
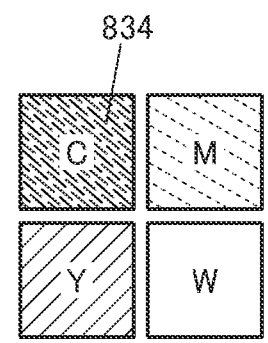

Providing the pixel 834 having a function of emitting white light (W) in the display device 810 as illustrated in FIGS. 21C and 21E can increase the luminance of a displayed image. Furthermore, increasing the number of colors exhibited by the pixels 834 as illustrated in FIG. 21D and the like can increase the reproducibility of intermediate colors and improve the display quality.

Figure 21F:
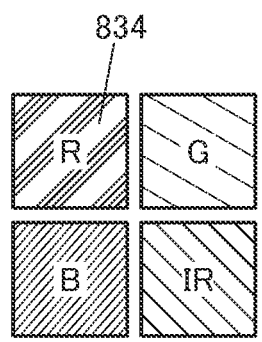
Figure 21G:
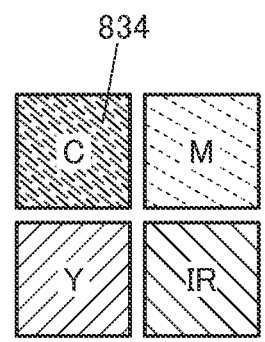

As illustrated in FIG. 21F, the display device 810 may include the pixel 834 having a function of emitting infrared light (IR) in addition to the pixel 834 having a function of emitting red light (R), the pixel 834 having a function of emitting green light (G), and the pixel 834 having a function of emitting blue light (B). Alternatively, as illustrated in FIG. 21G, the display device 810 may include the pixel 834 having a function of emitting infrared light (IR) in addition to the pixel 834 having a function of emitting cyan light (C), the pixel 834 having a function of emitting magenta light (M), and the pixel 834 having a function of emitting yellow light (Y). Alternatively, the display device 810 may include the pixel 834 having a function of emitting white light (W) in addition to the pixels 834 illustrated in FIG. 21F or FIG. 21G.

Figure 22A:
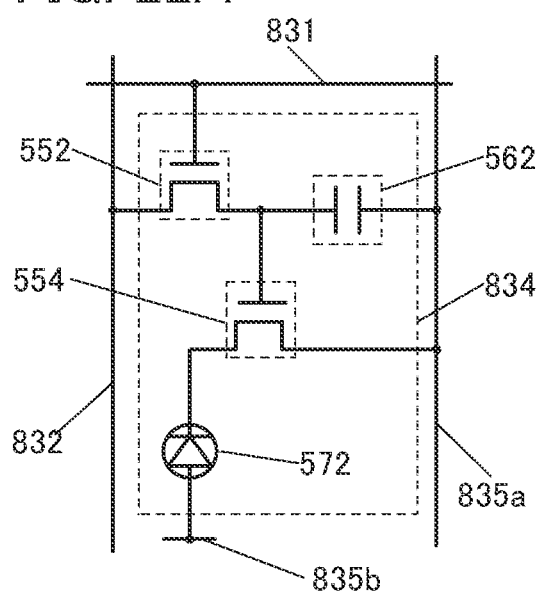
FIGS. 22A and 22B are circuit diagrams each illustrating a configuration example of a pixel.
Figure 22B:
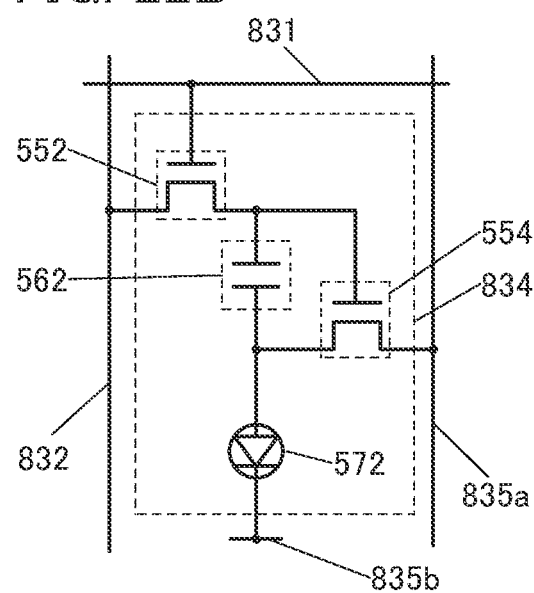

FIGS. 22A and 22B are circuit diagrams each illustrating a configuration example of the pixel 834. The pixel 834 having the configuration illustrated in FIG. 22A includes a transistor 552, a transistor 554, a capacitor 562, and a light-emitting element 572. As the light-emitting element 572, an EL element utilizing electroluminescence can be used, for example. The EL element includes a layer containing a light-emitting compound (hereinafter also referred to as EL layer) between a pair of electrodes. When a potential difference that is greater than the threshold voltage of the EL element is generated between the pair of electrodes, holes are injected to the EL layer from the anode side and electrons are injected to the EL layer from the cathode side. The injected electrons and holes are recombined in the EL layer and a light-emitting substance contained in the EL layer emits light.

EL elements are classified according to whether a light-emitting material is an organic compound or an inorganic compound. In general, the former is referred to as an organic EL element, and the latter is referred to as an inorganic EL element.

In an organic EL element, by voltage application, electrons are injected from one electrode to the EL layer and holes are injected from the other electrode to the EL layer. Then, the carriers (electrons and holes) are recombined, and thus, a light-emitting organic compound is excited. The light-emitting organic compound returns to a ground state from the excited state, thereby emitting light. Owing to such a mechanism, this light-emitting element is referred to as a current-excitation light-emitting element.

In addition to the light-emitting compound, the EL layer may further include any of a substance with a high hole-injection property, a substance with a high hole-transport property, a hole-blocking material, a substance with a high electron-transport property, a substance with a high electron-injection property, a substance with a bipolar property (a substance with a high electron- and hole-transport properties), and the like.

The EL layer can be formed by an evaporation method (including a vacuum evaporation method), a transfer method, a printing method, an inkjet method, a coating method, or the like.

The inorganic EL elements are classified according to their device structures into a dispersion-type inorganic EL element and a thin-film inorganic EL element. A dispersion-type inorganic EL element includes a light-emitting layer where particles of a light-emitting material are dispersed in a binder, and its light emission mechanism is donor-acceptor recombination type light emission that utilizes a donor level and an acceptor level. A thin-film inorganic EL element has a structure where a light-emitting layer is positioned between dielectric layers, which are further positioned between electrodes, and its light emission mechanism is localization type light emission that utilizes inner-shell electron transition of metal ions.

In order to extract light emitted from the light-emitting element, at least one of the pair of electrodes needs to be transparent. The light-emitting element that is formed over a substrate together with a transistor can have any of a top emission structure in which emitted light is extracted through the surface opposite to the substrate; a bottom emission structure in which emitted light is extracted through the surface on the substrate side; and a dual emission structure in which emitted light is extracted through both sides.

Note that an element similar to the light-emitting element 572 can be used as light-emitting elements other than the light-emitting element 572.

One of a source and a drain of the transistor 552 is electrically connected to the wiring 832. The other of the source and the drain of the transistor 552 is electrically connected to one electrode of the capacitor 562 and a gate of the transistor 554. The other electrode of the capacitor 562 is electrically connected to a wiring 835*a*. A gate of the transistor 552 is electrically connected to the wiring 831. One of a source and a drain of the transistor 554 is electrically connected to the wiring 835*a*. The other of the source and the drain of the transistor 554 is electrically connected to one electrode of the light-emitting element 572. The other electrode of the light-emitting element 572 is electrically connected to a wiring 835*b*. The potential VSS is supplied to the wiring 835*a*, and the potential VDD is supplied to the wiring 835*b*. The wiring 835*a* and the wiring 835*b* function as power supply lines.

In the pixel 834 having the configuration illustrated in FIG. 22A, a current flowing through the light-emitting element 572 is controlled in accordance with a potential supplied to the gate of the transistor 554, whereby the luminance of light emitted from the light-emitting element 572 is controlled.

FIG. 22B illustrates a configuration different from that of the pixel 834 in FIG. 22A. In the pixel 834 having the configuration illustrated in FIG. 22B, one of the source and the drain of the transistor 552 is electrically connected to the wiring 832. The other of the source and the drain of the transistor 552 is electrically connected to one electrode of the capacitor 562 and the gate of the transistor 554. The gate of the transistor 552 is electrically connected to the wiring 831. One of the source and the drain of the transistor 554 is electrically connected to the wiring 835*a*. The other of the source and the drain of the transistor 554 is electrically connected to the other electrode of the capacitor 562 and one electrode of the light-emitting element 572. The other electrode of the light-emitting element 572 is electrically connected to the wiring 835b. The potential VDD is supplied to the wiring 835a, and the potential VSS is supplied to the wiring 835b.

Figure 23A:
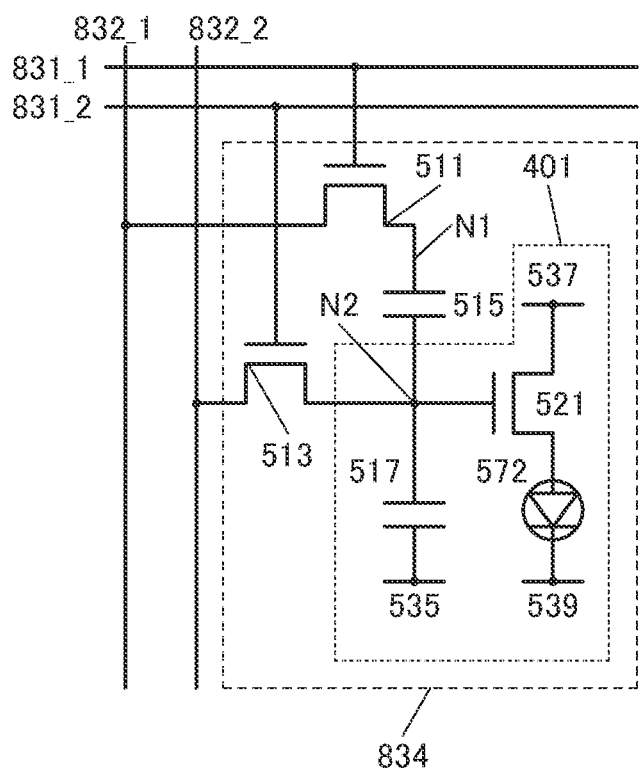
FIG. 23A is a circuit diagram illustrating a configuration example of a pixel.

FIG. 23A illustrates a configuration example of the pixel 834 different from that having the configuration in FIG. 22A or FIG. 22B in including a memory. The pixel 834 having the configuration in FIG. 23A includes a transistor 511, a transistor 513, a transistor 521, a capacitor 515, a capacitor 517, and the light-emitting element 572. To the pixel 834, a wiring 831_1 and a wiring 8312 are electrically connected as the wiring 831 functioning as a scan line, and a wiring 832_1 and a wiring 832_2 are electrically connected as the wiring 832 functioning as a data line.

One of a source and a drain of the transistor 511 is electrically connected to the wiring 832_1. The other of the source and the drain of the transistor 511 is electrically connected to one electrode of the capacitor 515. A gate of the transistor 511 is electrically connected to the wiring 831_1. One of a source and a drain of the transistor 513 is electrically connected to the wiring 832_2. The other of the source and the drain of the transistor 513 is electrically connected to the other electrode of the capacitor 515. A gate of the transistor 513 is electrically connected to the wiring 831_2. The other electrode of the capacitor 515 is electrically connected to one electrode of the capacitor 517. The one electrode of the capacitor 517 is electrically connected to a gate of the transistor 521. One of a source and a drain of the transistor 521 is electrically connected to one electrode of the light-emitting element 572. The other electrode of the capacitor 517 is electrically connected to a wiring 535. The other of the source and the drain of the transistor 521 is electrically connected to a wiring 537. The other electrode of the light-emitting element 572 is electrically connected to a wiring 539.

In this specification and the like, a voltage supplied to a light-emitting element indicates a difference between a potential supplied to one electrode of the light-emitting element and a potential supplied to the other electrode of the light-emitting element.

A node where the other of the source and the drain of the transistor 511 and the one electrode of the capacitor 515 are electrically connected to each other is referred to as a node N1. A node where the other of the source and the drain of the transistor 513, the one electrode of the capacitor 517, and the gate of the transistor 521 are electrically connected to each other is referred to as a node N2. In FIG. 23A, a circuit composed of the capacitor 517, the transistor 521, and the light-emitting element 572 is referred to as a circuit 401.

The wiring 535 can be shared by all pixels 834 provided in the display device 810, for example. In that case, a potential supplied to the wiring 535 is a common potential. A constant potential can be supplied to the wiring 537 and the wiring 539. For example, a high potential can be supplied to the wiring 537, and a low potential can be supplied to the wiring 539. The wirings 537 and 539 function as power supply lines.

The transistor 521 has a function of controlling a current to be supplied to the light-emitting element 572. The capacitor 517 functions as a storage capacitor. The capacitor 517 may be omitted.

Note that FIG. 23A illustrates a configuration in which the anode of the light-emitting element 572 is electrically connected to the transistor 521; alternatively, the transistor 521 may be electrically connected to the cathode. In that case, the value of the potential of the wiring 537 and the value of the potential of the wiring 539 can be changed as appropriate.

In the pixel 834, turning off the transistor 511 enables retention of the potential of the node N1. Turning off the transistor 513 enables retention of the potential of the node N2. Furthermore, by turning off the transistor 513 and then writing a predetermined potential to the node N1 through the transistor 511, the potential of the node N2 can be changed in accordance with a change in the potential of the node N1 by capacitive coupling through the capacitor 515.

A transistor containing a metal oxide in a channel formation region (hereinafter also referred to as OS transistor) can be used as the transistors 511 and 513. A metal oxide can have a band gap of 2 eV or more, or 2.5 eV or more. Thus, an OS transistor exhibits an extremely low leakage current (off-state current) in an off state. Accordingly, the use of OS transistors as the transistors 511 and 513 enables the potentials of the nodes N1 and N2 to be held for a long time.

The metal oxide can be, for example, an In-M-Zn oxide (the element M is one or more of aluminum, gallium, yttrium, tin, copper, vanadium, beryllium, boron, titanium, iron, nickel, germanium, zirconium, molybdenum, lanthanum, cerium, neodymium, hafnium, tantalum, tungsten, magnesium, and the like). In particular, aluminum, gallium, yttrium, or tin is preferably used for the element M. Alternatively, indium oxide, zinc oxide, an In—Ga oxide, an In—Zn oxide, a Ga—Zn oxide, or gallium oxide may be used as the metal oxide.

[Example of Operation Method for Pixel 834]

Figure 23B:
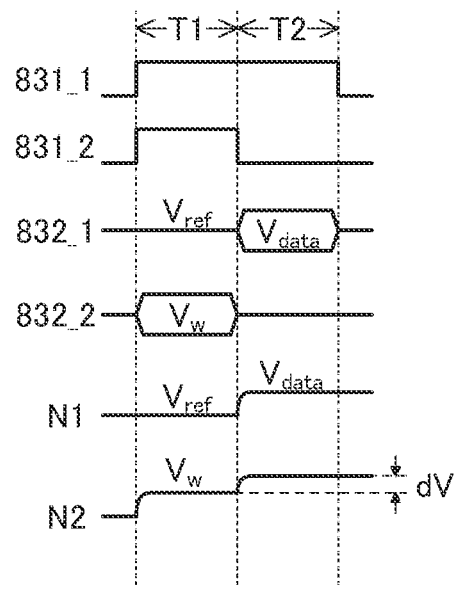
FIG. 23B is a timing chart illustrating an example of an operation method of the pixel.

Next, an example of an operation method for the pixel 834 having the configuration in FIG. 23A will be described with reference to FIG. 23B. FIG. 23B is a timing chart of the operation of the pixel 834 having the configuration in FIG. 23A. Note that for simplification of the description, the influence of various kinds of resistance such as wiring resistance; parasitic capacitance of a transistor, a wiring, or the like; and the threshold voltage of a transistor, for example, is not taken into consideration here.

In the operation shown in FIG. 23B, one frame period is divided into a period T1 and a period T2. The period T1 is a period in which a potential is written to the node N2, and the period T2 is a period in which a potential is written to the node N1.

In the period T1, a potential for turning on the transistor is supplied to both the wiring 831_1 and the wiring 831_2. In addition, a potential $V_{ref}$ that is a fixed potential is supplied to the wiring 832_1, and a potential $V_w$ is supplied to the wiring 832_2.

The potential $V_{ref}$ is supplied from the wiring 832_1 to the node N1 through the transistor 511. The potential $V_w$ is supplied from the wiring 832_2 to the node N2 through the transistor 513. Thus, a potential difference $V_w$-$V_{ref}$ is retained in the capacitor 515.

Then, in the period T2, a potential for turning on the transistor 511 is supplied to the wiring 831_1, and a potential for turning off the transistor 513 is supplied to the wiring 831_2. A potential $V_{data}$ is supplied to the wiring 832_1, and a predetermined constant potential is supplied to the wiring 832_2. Note that the potential of the wiring 832_2 may be floating.

The potential $V_{data}$ is supplied to the node N1 through the transistor 511. At this time, owing to capacitive coupling through the capacitor 515, the potential of the node N2 is changed by a potential dV in accordance with the potential $V_{data}$. That is, a potential that is the sum of the potential $V_w$ and the potential dV is input to the circuit 401. Note that although the potential dV is shown as having a positive value in FIG. 23B, the potential dV may have a negative value. That is, the potential $V_{data}$ may be lower than the potential $V_{ref}$.

Here, the potential dV is roughly determined by the capacitance of the capacitor 515 and the capacitance of the circuit 401. When the capacitance of the capacitor 515 is sufficiently larger than the capacitance of the circuit 401, the potential dV becomes close to a potential difference $V_{data}-V_{ref}$.

As described above, the pixel 834 can generate the potential supplied to the node N2 in combination with two kinds of data signals; thus, an image displayed on the pixel array 833 can be corrected inside the pixel 834. Here, one of the two kinds of data signals can be the aforementioned image signal, and the other can be a correction signal, for example. For example, when the potential $V_w$ corresponding to a correction signal is supplied to the node N2 in the period T1 and then the potential $V_{data}$ corresponding to an image signal is supplied to the node N1 in the period T2, an image based on the image signal corrected by the correction signal can be displayed on the pixel array 833. Note that not only image signals but also correction signals and the like can be generated by the source driver circuit 822 included in the display device 810.

In the pixel 834 having the configuration in FIG. 23A, the potential of the node N2 can be set higher than the maximum potential that can be supplied to the wirings 832_1 and 832_2. Thus, a high voltage can be supplied to the light-emitting element 572. Specifically, the potential of the wiring 537 can be set higher, for example. Accordingly, when the light-emitting element 572 is an organic EL element, the light-emitting element can employ a tandem structure described later. This increases the current efficiency and external quantum efficiency of the light-emitting element 572. Thus, a high-luminance image can be displayed on the display device 810. Moreover, power consumption of the display device 810 can be reduced.

Note that the pixel configuration is not limited to that illustrated in FIG. 23A, and a transistor, a capacitor, or the like may be added. For example, when one transistor and one capacitor are added to the configuration in FIG. 23A, three nodes capable of holding a potential can be provided. That is, the pixel 834 can have another node capable of holding a potential, in addition to the node N1 and the node N2. Thus, the potential of the node N2 can be further increased. Consequently, a larger amount of current can flow through the light-emitting element 572.

FIGS. 24A to 24E illustrate configuration examples of the circuit 401 different from that in FIG. 23A. Like the circuit 401 with the configuration illustrated in FIG. 23A, the circuit 401 with the configuration illustrated in FIG. 24A includes the capacitor 517, the transistor 521, and the light-emitting element 572.

Figure 24A:
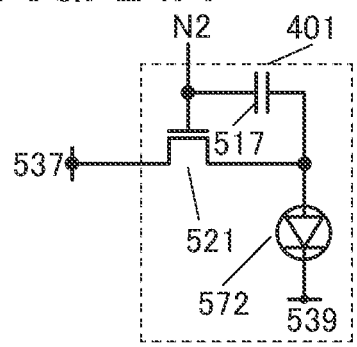
FIGS. 24A to 24E are circuit diagrams each illustrating a configuration example of a pixel.

In the circuit 401 with the configuration illustrated in FIG. 24A, the gate of the transistor 521 and one electrode of the capacitor 517 are electrically connected to the node N2. One of the source and the drain of the transistor 521 is electrically connected to the wiring 537. The other of the source and the drain of the transistor 521 is electrically connected to the other electrode of the capacitor 517. The other electrode of the capacitor 517 is electrically connected to one electrode of the light-emitting element 572. The other electrode of the light-emitting element 572 is electrically connected to the wiring 539.

Figure 24B:
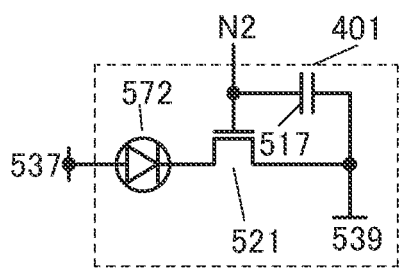

Like the circuit 401 with the configuration illustrated in FIG. 23A, the circuit 401 with the configuration illustrated in FIG. 24B includes the capacitor 517, the transistor 521, and the light-emitting element 572.

In the circuit 401 with the configuration illustrated in FIG. 24B, the gate of the transistor 521 and one electrode of the capacitor 517 are electrically connected to the node N2. One electrode of the light-emitting element 572 is electrically connected to the wiring 537. The other electrode of the light-emitting element 572 is electrically connected to one of the source and the drain of the transistor 521. The other of the source and the drain of the transistor 521 is electrically connected to the other electrode of the capacitor 517. The other electrode of the capacitor 517 is electrically connected to the wiring 539.

Figure 24C:
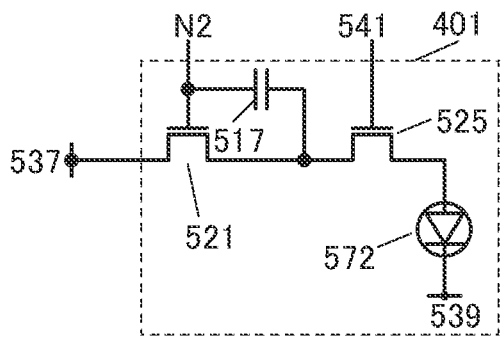

FIG. 24C illustrates a configuration example of the circuit 401 in which a transistor 525 is added to the circuit 401 in FIG. 24A. One of a source and a drain of the transistor 525 is electrically connected to the other of the source and the drain of the transistor 521 and the other electrode of the capacitor 517. The other of the source and the drain of the transistor 525 is electrically connected to one electrode of the light-emitting element 572. A gate of the transistor 525 is electrically connected to a wiring 541. The wiring 541 has a function of a scan line for controlling the conduction of the transistor 525.

In the pixel 834 including the circuit 401 with the configuration illustrated in FIG. 24C, even when the potential of the node N2 becomes higher than the threshold voltage of the transistor 521, a current does not flow through the light-emitting element 572 unless the transistor 525 is turned on. Thus, a malfunction of the display device 810 can be inhibited.

Figure 24D:
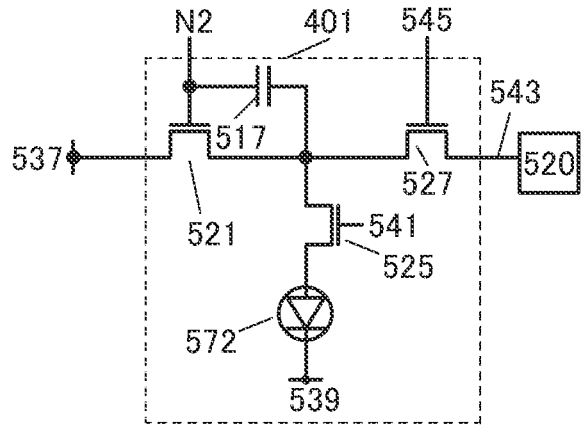

FIG. 24D illustrates a configuration example of the circuit 401 in which a transistor 527 is added to the circuit 401 in FIG. 24C. One of a source and a drain of the transistor 527 is electrically connected to the other of the source and the drain of the transistor 521. The other of the source and the drain of the transistor 527 is electrically connected to a wiring 543. A gate of the transistor 527 is electrically connected to a wiring 545. The wiring 545 has a function of a scan line for controlling the conduction of the transistor 527.

The wiring 543 can be electrically connected to a supply source of a certain potential such as a reference potential. That is, the wiring 543 has a function of a power supply line. Supplying a certain potential from the wiring 543 to the other of the source and the drain of the transistor 521 enables stable writing of an image signal to the pixel 834.

The wiring 543 can be electrically connected to a circuit 520. The circuit 520 can have at least one of a function of a supply source of the certain potential, a function of obtaining electrical characteristics of the transistor 521, and a function of generating a correction signal.

Figure 24E:
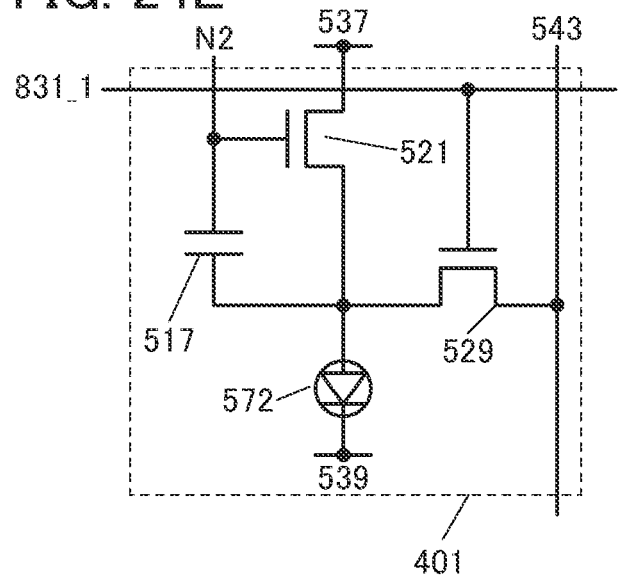

The circuit 401 having the configuration illustrated in FIG. 24E includes the capacitor 517, the transistor 521, a transistor 529, and the light-emitting element 572.

In the circuit 401 with the configuration illustrated in FIG. 24E, the gate of the transistor 521 and one electrode of the capacitor 517 are electrically connected to the node N2. One of the source and the drain of the transistor 521 is electrically connected to the wiring 537. One of a source and a drain of the transistor 529 is electrically connected to the wiring 543.

The other electrode of the capacitor 517 is electrically connected to the other of the source and the drain of the transistor 521. The other of the source and the drain of the transistor 521 is electrically connected to the other of the source and the drain of the transistor 529. The other of the source and the drain of the transistor 529 is electrically connected to one electrode of the light-emitting element 572.

A gate of the transistor 529 is electrically connected to the wiring 831_1. The other electrode of the light-emitting element 572 is electrically connected to the wiring 539.

<Structure Example 2 of Display Device>

Figure 25:
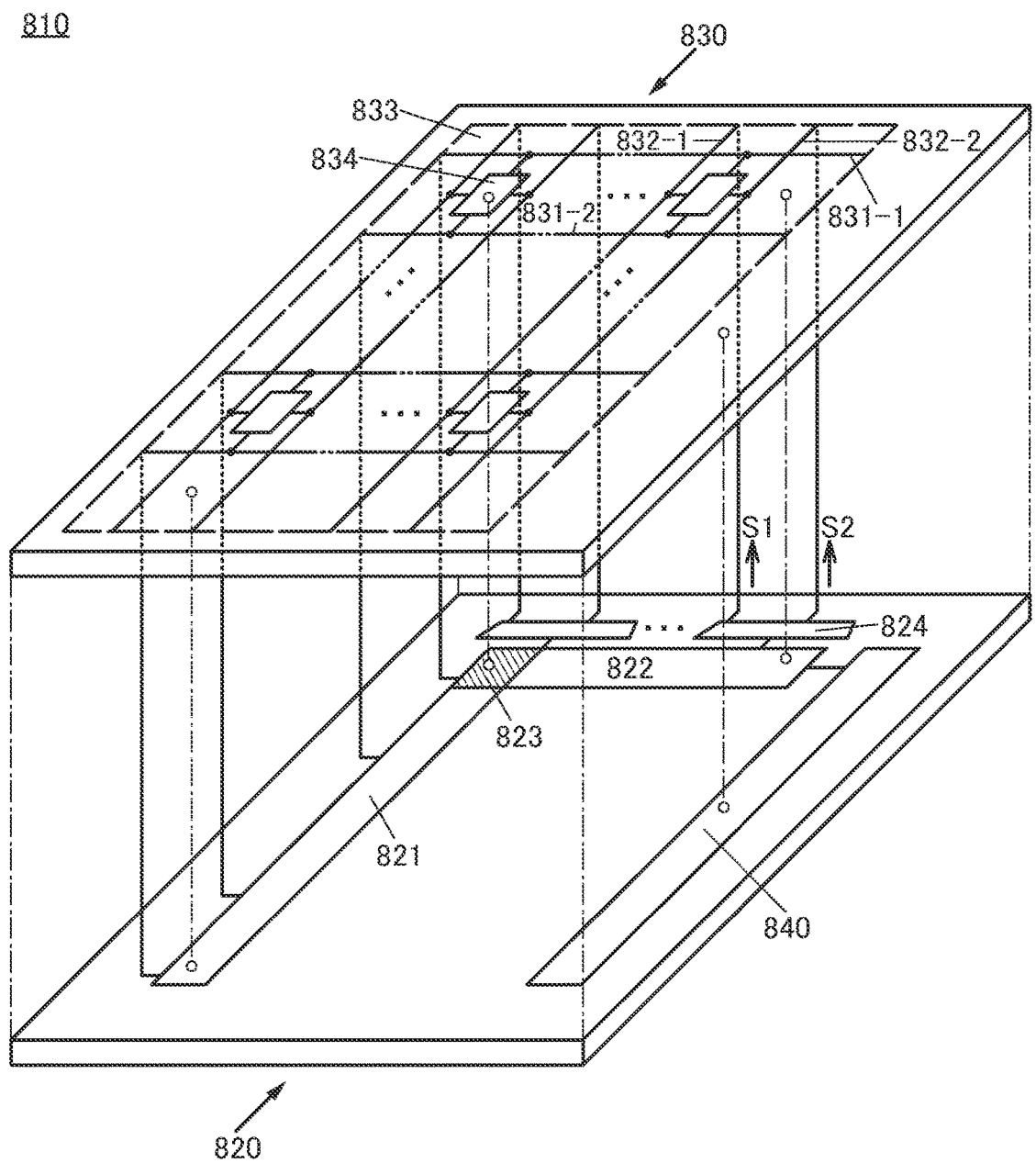
FIG. 25 is a block diagram illustrating a structure example of a display device.

FIG. 25 is a block diagram illustrating a structure example of the display device 810 in which the pixels 834 have the configuration illustrated in FIG. 23A. In the display device 810 having the structure illustrated in FIG. 25, a demultiplexer circuit 824 is provided in addition to the components of the display device 810 illustrated in FIG. 8. The demultiplexer circuit 824 can be provided in the layer 820 as illustrated in FIG. 25, for example. Note that the number of demultiplexer circuits 824 can be equal to the number of columns of the pixels 834 arranged in the pixel array 833, for example.

The gate driver circuit 821 is electrically connected to the pixel 834 through a wiring 831-1. The gate driver circuit 821 is electrically connected to the pixel 834 through a wiring 831-2. The wiring 831-1 and the wiring 831-2 function as scan lines.

The source driver circuit 822 is electrically connected to an input terminal of the demultiplexer circuit 824. A first output terminal of the demultiplexer circuit 824 is electrically connected to the pixel 834 through a wiring 832-1. A second output terminal of the demultiplexer circuit 824 is electrically connected to the pixel 834 through a wiring 832-2. The wiring 832-1 and the wiring 832-2 function as data lines.

Note that the source driver circuit 822 and the demultiplexer circuits 824 may be collectively referred to as a source driver circuit. In other words, the demultiplexer circuits 824 may be included in the source driver circuit 822.

In the display device 810 having the structure in FIG. 25, the source driver circuit 822 has a function of generating an image signal S1 and an image signal S2. The demultiplexer circuit 824 has a function of supplying the image signal S1 to the pixel 834 through the wiring 832-1, and a function of supplying the image signal S2 to the pixel 834 through the wiring 832-2. Here, when the display device 810 having the structure in FIG. 25 operates with the method illustrated in FIG. 23B, the potential $V_{data}$ can be a potential corresponding to the image signal S1 and the potential $V_w$ can be a potential corresponding to the image signal S2.

When the potential $V_w$ is supplied to the node N2 and then the potential $V_{data}$ is supplied to the node N1 as shown in FIG. 23B, the potential of the node N2 becomes $V_w$+dV. Here, the potential dV corresponds to the potential $V_{data}$ as described above. As a result, the image signal S1 can be added to the image signal S2. That is, the image signal S1 can be superimposed on the image signal S2.

The level of the potential $V_{data}$ corresponding to the image signal S1 and the level of the potential $V_w$ corresponding to the image signal S2 are limited by the withstand voltage of the source driver circuit 822, for example. In view of this, superimposing the image signal S1 and the image signal S2 enables an image corresponding to an image signal having a potential higher than a potential that the source driver circuit 822 can output, to be displayed on the pixel array 833. Thus, a large amount of current can flow through the light-emitting element 572; hence, the pixel array 833 can display a high-luminance image. Moreover, the dynamic range, which is the range of luminance of images that the pixel array 833 can display, can be enlarged.

An image corresponding to the image signal S1 and an image corresponding to the image signal S2 may be the same or different from each other. When an image corresponding to the image signal S1 and an image corresponding to the image signal S2 are the same, the pixel array 833 can display an image with higher luminance than the luminance of the image corresponding to either the image signal S1 or the image signal S2.

Figure 26:
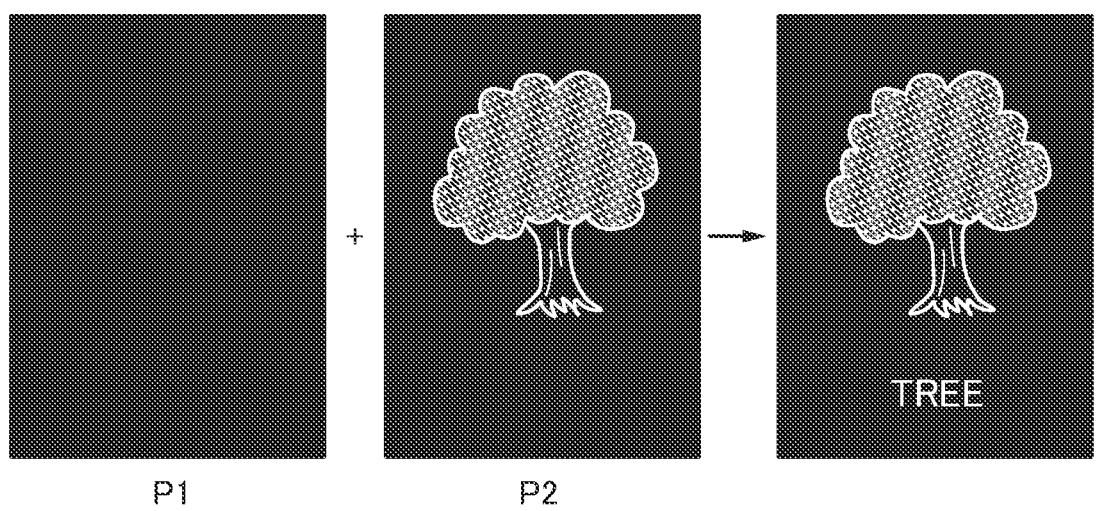
FIG. 26 illustrates an operation example of a display device.

FIG. 26 shows the case where an image P1 corresponding to the image signal S1 includes only letters, and an image P2 corresponding to the image signal S2 includes a picture and letters. In this case, when the image P1 and the image P2 are superimposed on each other, the luminance of the letters can be increased, whereby the letters can be emphasized, for example. As illustrated in FIG. 23B, the potential of the node N2 is changed in accordance with the potential $V_{data}$ after the potential $V_w$ is written to the node N2; hence, to rewrite the potential $V_w$ corresponding to the image signal S2, the potential $V_{data}$ of the image signal S1 needs to be written again. Meanwhile, to rewrite the potential $V_{data}$, the potential $V_w$ does not need to be rewritten as long as the charge written to the node N2 at the time T1 shown in FIG. 23B is retained without being leaked through the transistor 513 or the like. Therefore, in the case illustrated in FIG. 26, the luminance of the letters can be controlled by adjusting the level of the potential $V_{data}$.

Here, to rewrite the potential $V_w$ corresponding to the image signal S2, the potential $V_{data}$ corresponding to the image signal S1 needs to be written again as described above. On the other hand, to rewrite the potential $V_{data}$, the potential $V_w$ does not need to be rewritten. Therefore, the image P2 is preferably an image that needs to be rewritten less frequently than the image P1. Note that the image P1 is not limited to an image including only letters, and the image P2 is not limited to an image including a picture and letters.

<Example of Cross-Sectional Structure of Display Device>

Figure 27:
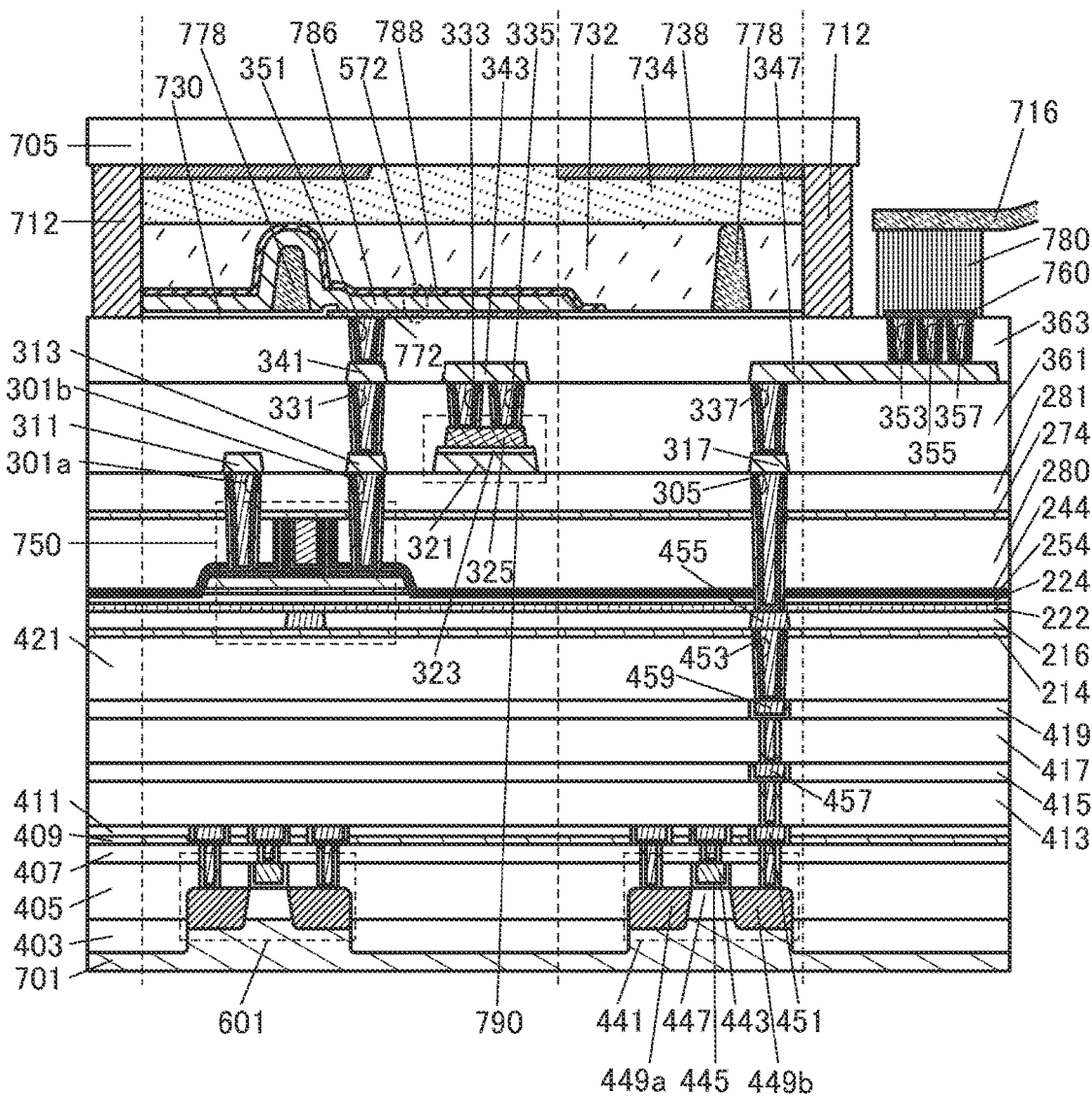
FIG. 27 is a cross-sectional view of a structure example of a display device.

FIG. 27 is a cross-sectional view illustrating a structure example of the display device 810. The display device 810 includes a substrate 701 and a substrate 705. The substrate 701 and the substrate 705 are attached to each other with a sealant 712.

As the substrate 701, a single crystal semiconductor substrate such as a single crystal silicon substrate can be used. Note that a semiconductor substrate other than a single crystal semiconductor substrate may be used as the substrate 701.

A transistor 441 and a transistor 601 are provided on the substrate 701. The transistor 441 can be a transistor provided in the circuit 840. The transistor 601 can be a transistor provided in the gate driver circuit 821 or a transistor provided in the source driver circuit 822. That is, the transistor 441 and the transistor 601 can be provided in the layer 820 illustrated in FIG. 8 and the like.

The transistor 441 is formed of a conductor 443 functioning as a gate electrode, an insulator 445 functioning as a gate insulator, and part of the substrate 701 and includes a semiconductor region 447 including a channel formation region, a low-resistance region 449a functioning as one of a source region and a drain region, and a low-resistance region 449b functioning as the other of the source region and the drain region. The transistor 441 can be a p-channel transistor or an n-channel transistor.

The transistor 441 is electrically isolated from other transistors by an element isolation layer 403. FIG. 27 illustrates the case where the transistor 441 and the transistor 601 are electrically isolated from each other by the element isolation layer 403. The element isolation layer 403 can be formed by a local oxidation of silicon (LOCOS) method, a shallow trench isolation (STI) method, or the like.

Here, in the transistor 441 illustrated in FIG. 27, the semiconductor region 447 has a projecting shape. Moreover, the conductor 443 is provided to cover a side surface and a top surface of the semiconductor region 447 with the insulator 445 therebetween. Note that FIG. 27 does not illustrate the state where the conductor 443 covers the side surface of the semiconductor region 447. A material for adjusting the work function can be used for the conductor 443.

A transistor having a projecting semiconductor region, like the transistor 441, can be referred to as a fin-type transistor because a projecting portion of a semiconductor substrate is used. An insulator functioning as a mask for forming a projecting portion may be provided in contact with the top surface of the projecting portion. Although FIG. 27 illustrates the structure in which the projecting portion is formed by processing part of the substrate 701, a semiconductor having a projecting shape may be formed by processing an SOI substrate.

Note that the structure of the transistor 441 illustrated in FIG. 27 is only an example; the structure of the transistor 441 is not particularly limited and can be changed as appropriate in accordance with the circuit configuration, an operation method for the circuit, or the like. For example, the transistor 441 may be a planar transistor.

The transistor 601 can have the same structure as the transistor 441.

An insulator 405, an insulator 407, an insulator 409, and an insulator 411 are provided over the substrate 701, in addition to the element isolation layer 403 and the transistors 441 and 601. A conductor 451 is embedded in the insulator 405, the insulator 407, the insulator 409, and the insulator 411. Here, the top surface of the conductor 451 and the top surface of the insulator 411 can be substantially level with each other.

An insulator 413 and an insulator 415 are provided over the conductor 451 and the insulator 411. A conductor 457 is embedded in the insulator 413 and the insulator 415. The conductor 457 can be provided in the same layer as the wirings 121 to 123 illustrated in FIG. 20, for example. Here, the top surface of the conductor 457 and the top surface of the insulator 415 can be substantially level with each other.

An insulator 417 and an insulator 419 are provided over the conductor 457 and the insulator 415. A conductor 459 is embedded in the insulator 417 and the insulator 419. The conductor 459 can be provided in the same layer as the wirings 141 to 143 illustrated in FIG. 20, for example. Here, the top surface of the conductor 459 and the top surface of the insulator 419 can be substantially level with each other.

An insulator 421 and an insulator 214 are provided over the conductor 459 and the insulator 419. A conductor 453 is embedded in the insulator 421 and the insulator 214. Here, the top surface of the conductor 453 and the top surface of the insulator 214 can be substantially level with each other.

An insulator 216 is provided over the conductor 453 and the insulator 214. A conductor 455 is embedded in the insulator 216. Here, the top surface of the conductor 455 and the top surface of the insulator 216 can be substantially level with each other.

An insulator 222, an insulator 224, an insulator 254, an insulator 244, an insulator 280, an insulator 274, and an insulator 281 are provided over the conductor 455 and the insulator 216. A conductor 305 is embedded in the insulator 222, the insulator 224, the insulator 254, the insulator 244, the insulator 280, the insulator 274, and the insulator 281.

Here, the top surface of the conductor 305 and the top surface of the insulator 281 can be substantially level with each other.

An insulator 361 is provided over the conductor 305 and the insulator 281. A conductor 317 and a conductor 337 are embedded in the insulator 361. Here, the top surface of the conductor 337 and the top surface of the insulator 361 can be substantially level with each other.

An insulator 363 is provided over the conductor 337 and the insulator 361. A conductor 347, a conductor 353, a conductor 355, and a conductor 357 are embedded in the insulator 363. Here, the top surfaces of the conductors 353, 355, and 357 and the top surface of the insulator 363 can be substantially level with each other.

A connection electrode 760 is provided over the conductor 353, the conductor 355, the conductor 357, and the insulator 363. An anisotropic conductor 780 is provided to be electrically connected to the connection electrode 760. A flexible printed circuit (FPC) 716 is provided to be electrically connected to the anisotropic conductor 780. A variety of signals and the like are supplied to the display device 810 from the outside through the FPC 716.

As illustrated in FIG. 27, the low-resistance region 449b functioning as the other of the source region and the drain region of the transistor 441 is electrically connected to the FPC 716 through the conductor 451, the conductor 457, the conductor 459, the conductor 453, the conductor 455, the conductor 305, the conductor 317, the conductor 337, the conductor 347, the conductor 353, the conductor 355, the conductor 357, the connection electrode 760, and the anisotropic conductor 780. Although FIG. 27 illustrates three conductors 353, 355, and 357 as conductors that electrically connect the connection electrode 760 and the conductor 347, one embodiment of the present invention is not limited thereto. The number of conductors having a function of electrically connecting the connection electrode 760 and the conductor 347 may be one, two, or four or more. Providing a plurality of conductors having a function of electrically connecting the connection electrode 760 and the conductor 347 can reduce the contact resistance.

A transistor 750 is provided over the insulator 214. The transistor 750 can be a transistor provided in the pixel 834. That is, the transistor 750 can be provided in the layer 830 illustrated in FIG. 8 and the like. An OS transistor can be used as the transistor 750. Owing to an extremely low off-state current of the OS transistor, an image signal or the like can be held for a longer time, so that the refresh operation can be less frequent. Thus, power consumption of the display device 810 can be reduced.

A conductor 301a and a conductor 301b are embedded in the insulator 254, the insulator 244, the insulator 280, the insulator 274, and the insulator 281. The conductor 301a is electrically connected to one of the source and the drain of the transistor 750, and the conductor 301b is electrically connected to the other of the source and the drain of the transistor 750. Here, the top surfaces of the conductors 301a and 301b and the top surface of the insulator 281 can be substantially level with each other.

A conductor 311, a conductor 313, a conductor 331, a capacitor 790, a conductor 333, and a conductor 335 are embedded in the insulator 361. The conductor 311 and the conductor 313 are electrically connected to the transistor 750 and serve as wirings. The conductor 333 and the conductor 335 are electrically connected to the capacitor 790. Here, the top surfaces of the conductors 331, 333, and 335 and the top surface of the insulator 361 can be substantially level with each other.

A conductor 341, a conductor 343, and a conductor 351 are embedded in the insulator 363. Here, the top surface of the conductor 351 and the top surface of the insulator 363 can be substantially level with each other.

The insulators 405, 407, 409, 411, 413, 415, 417, 419, 421, 214, 280, 274, 281, 361, and 363 function as an interlayer film and may also function as a planarization film that covers unevenness thereunder. For example, the top surface of the insulator 363 may be planarized by planarization treatment using a chemical mechanical polishing (CMP) method or the like to increase the level of planarity.

As illustrated in FIG. 27, the capacitor 790 includes a lower electrode 321 and an upper electrode 325. An insulator 323 is provided between the lower electrode 321 and the upper electrode 325. That is, the capacitor 790 has a stacked-layer structure in which the insulator 323 functioning as a dielectric is positioned between the pair of electrodes. Although FIG. 27 illustrates an example in which the capacitor 790 is provided over the insulator 281, the capacitor 790 may be provided over an insulator other than the insulator 281.

In the example in FIG. 27, the conductors 301a, 301b, and 305 are formed in one layer. The conductors 311, 313, and 317 and the lower electrode 321 are formed in one layer. The conductors 331, 333, 335, and 337 are formed in one layer. The conductors 341, 343, and 347 are formed in one layer. The conductors 351, 353, 355, and 357 are formed in one layer. Forming a plurality of conductors in one layer in this manner simplifies the process of manufacturing the display device 810 and thus makes the display device 810 inexpensive. Note that these conductors may be formed in different layers or may contain different types of materials.

The display device 810 illustrated in FIG. 27 includes the light-emitting element 572. The light-emitting element 572 includes a conductor 772, an EL layer 786, and a conductor 788. The conductor 788 is provided on the second substrate 705 side and functions as a common electrode. The conductor 772 is electrically connected to the other of the source and the drain of the transistor 750 through the conductor 351, the conductor 341, the conductor 331, the conductor 313, and the conductor 301b. The conductor 772 is formed over the insulator 363 and functions as a pixel electrode. The EL layer 786 contains an organic compound or an inorganic compound such as a quantum dot.

Examples of materials that can be used for an organic compound include a fluorescent material and a phosphorescent material. Examples of materials that can be used for a quantum dot include a colloidal quantum dot material, an alloyed quantum dot material, a core-shell quantum dot material, and a core quantum dot material.

In the display device 810 illustrated in FIG. 27, an insulator 730 is provided over the insulator 363. Here, the insulator 730 can cover part of the conductor 772. The light-emitting element 572 includes the light-transmitting conductor 788 and thus can be a top-emission light-emitting element. Note that the light-emitting element 572 may have a bottom-emission structure in which light is emitted towards the conductor 772 or a dual-emission structure in which light is emitted towards both the conductor 772 and the conductor 788.

The light-emitting element 572 can have a microcavity structure, which will be described later in detail. Thus, light of predetermined colors (e.g., RGB) can be extracted without a coloring layer, and the display device 810 can perform color display. The structure without a coloring layer can prevent light absorption due to the coloring layer. As a result, the display device 810 can display high-luminance images, and power consumption of the display device 810 can be reduced. Note that a structure without a coloring layer can be employed even when the EL layer 786 is formed into an island shape for each pixel or formed into a stripe shape for each pixel column, i.e., the EL layers 786 are formed by separate coloring.

A light-blocking layer 738 is provided to include a region overlapping with the insulator 730. The light-blocking layer 738 is covered with an insulator 734. A space between the light-emitting element 572 and the insulator 734 is filled with a sealing layer 732.

A component 778 is provided between the insulator 730 and the EL layer 786. Another component 778 is provided between the insulator 730 and the insulator 734. The component 778 is a columnar spacer and has a function of controlling the distance (cell gap) between the substrate 701 and the substrate 705. Note that a spherical spacer may be used as the component 778.

The light-blocking layer 738 and the insulator 734 that is in contact with the light-blocking layer 738 are provided on the substrate 705. The light-blocking layer 738 has a function of blocking light emitted from adjacent regions. Alternatively, the light-blocking layer 738 has a function of preventing external light from reaching the transistor 750 or the like.

Figure 28:
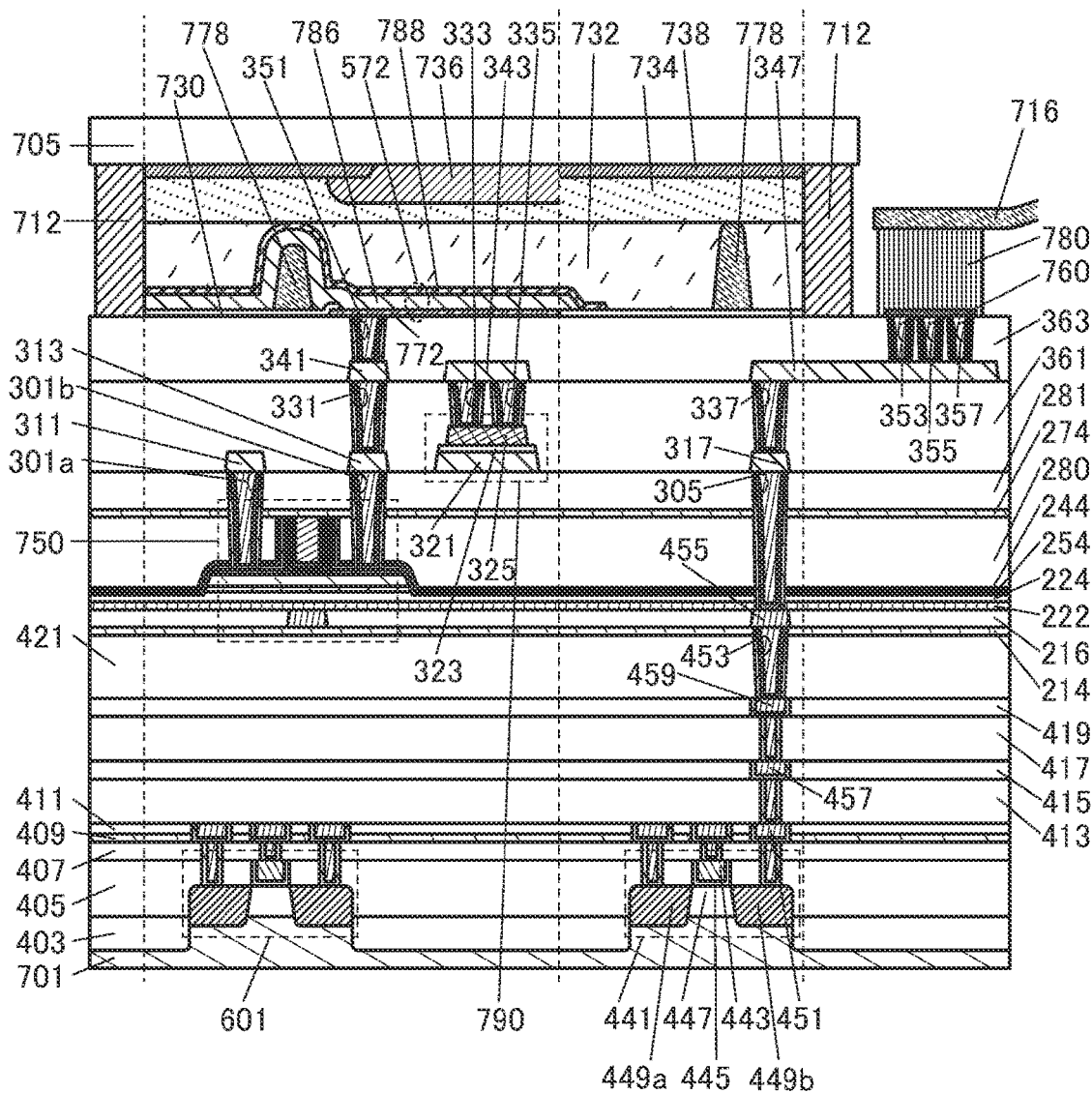
FIG. 28 is a cross-sectional view of a structure example of a display device.

FIG. 28 illustrates a variation example of the display device 810 in FIG. 27. The display device 810 in FIG. 28 is different from that in FIG. 27 in including a coloring layer 736. Providing the coloring layer 736 can improve the color purity of light extracted from the light-emitting element 572. Thus, the display device 810 can display high-quality images. Furthermore, all the light-emitting elements 572, for example, in the display device 810 can be light-emitting elements that emit white light; hence, the EL layers 786 are not necessarily formed by separate coloring, leading to higher definition of the display device 810.

Figure 29:
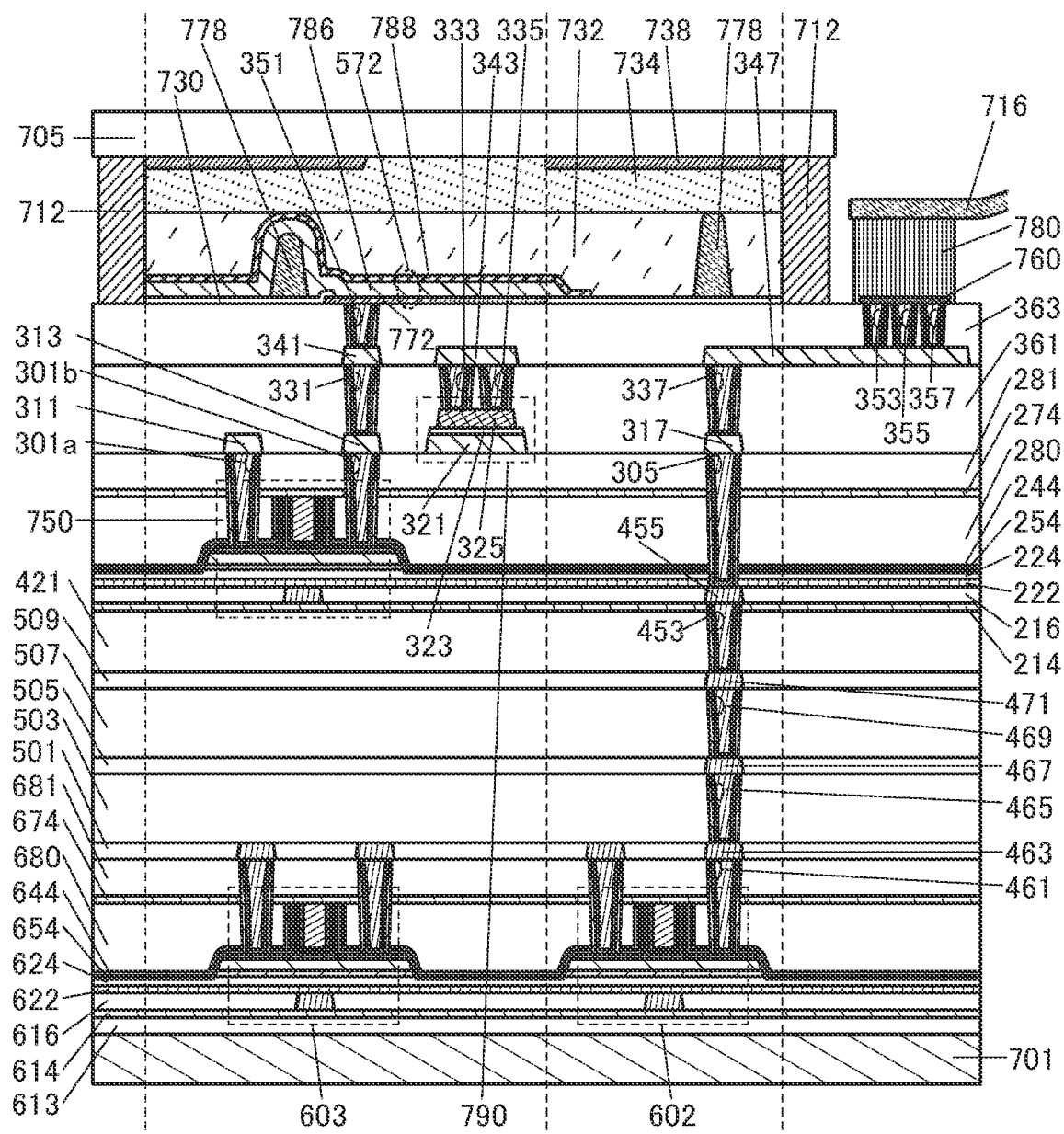
FIG. 29 is a cross-sectional view of a structure example of a display device.
Figure 30:
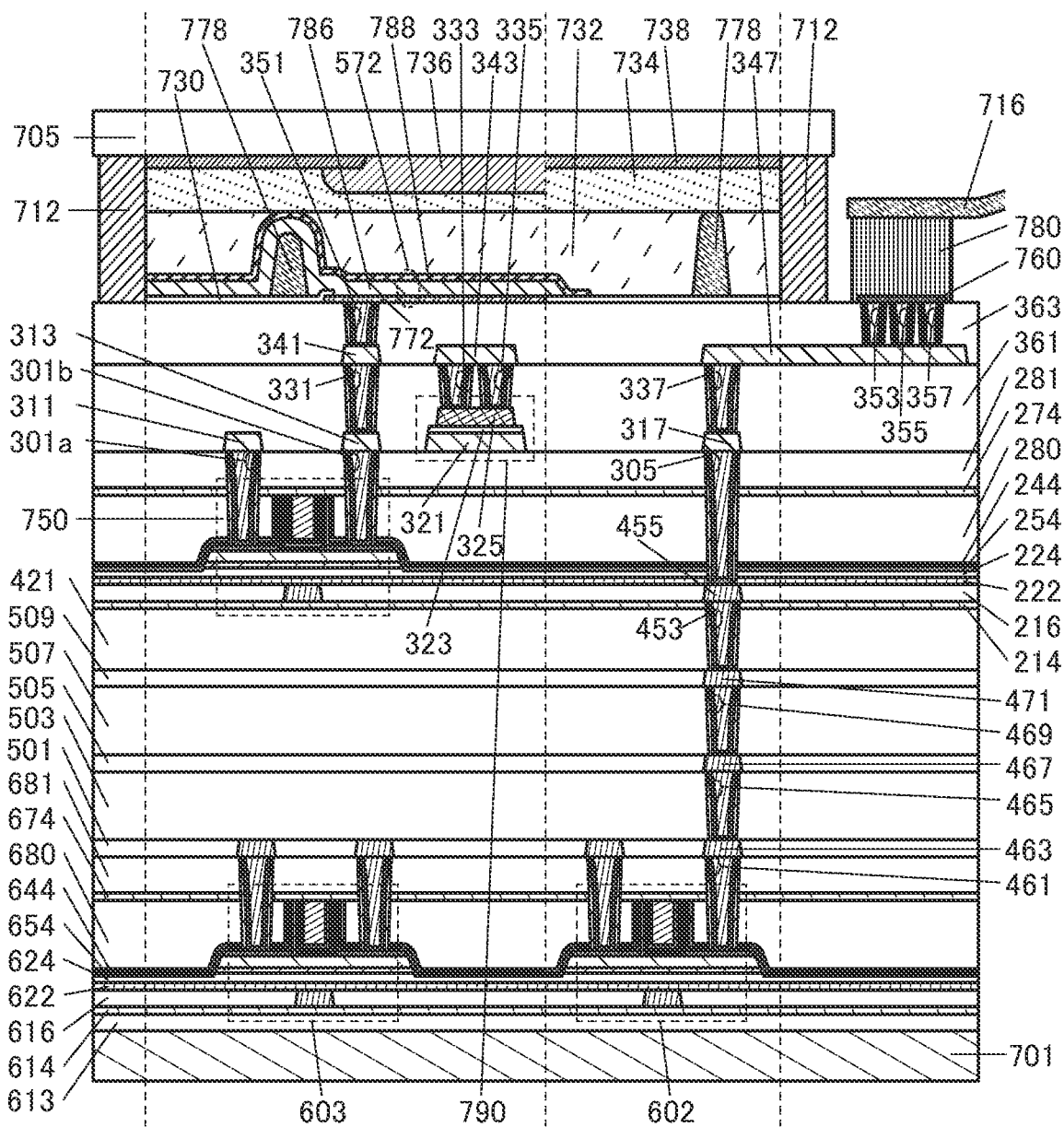
FIG. 30 is a cross-sectional view of a structure example of a display device.

Although FIG. 27 and FIG. 28 each illustrate a structure where the transistor 441 and the transistor 601 are provided so that their channel formation regions are formed inside the substrate 701 and the OS transistor is stacked over the transistor 441 and the transistor 601, one embodiment of the present invention is not limited thereto. FIG. 29 illustrates a variation example of FIG. 27, and FIG. 30 illustrates a variation example of FIG. 28. The display device 810 with the structure in FIG. 29 or FIG. 30 differs from that with the structure in FIG. 27 or FIG. 28 in that the transistor 750 is stacked over a transistor 602 and a transistor 603 that are OS transistors, instead of over the transistor 441 and the transistor 601. That is, the display device 810 with the structure in FIG. 29 or FIG. 30 includes a stack of OS transistors.

An insulator 613 and an insulator 614 are provided over the substrate 701, and the transistor 602 and the transistor 603 are provided over the insulator 614. Note that a transistor or the like may be provided between the substrate 701 and the insulator 613. For example, a transistor having a structure similar to that of the transistor 441 and the transistor 601 illustrated in FIG. 27 and FIG. 28 may be provided between the substrate 701 and the insulator 613.

The transistor 602 can be a transistor provided in the circuit 840. The transistor 603 can be a transistor provided in the gate driver circuit 821 or a transistor provided in the source driver circuit 822. That is, the transistor 602 and the transistor 603 can be provided in the layer 820 illustrated in FIG. 8 and the like. Note that when the circuit 840 is provided in the layer 830 as illustrated in FIG. 12, the transistor 602 can be provided in the layer 830.

The transistor 602 and the transistor 603 can have a structure similar to that of the transistor 750. Note that the transistor 602 and the transistor 603 may be OS transistors having a structure different from that of the transistor 750.

An insulator 616, an insulator 622, an insulator 624, an insulator 654, an insulator 644, an insulator 680, an insulator 674, and an insulator 681 are provided over the insulator 614, in addition to the transistor 602 and the transistor 603. A conductor 461 is embedded in the insulator 654, the insulator 644, the insulator 680, the insulator 674, and the insulator 681. Here, the top surface of the conductor 461 and the top surface of the insulator 681 can be substantially level with each other.

An insulator 501 is provided over the conductor 461 and the insulator 681. A conductor 463 is embedded in the insulator 501. Here, the top surface of the conductor 463 and the top surface of the insulator 501 can be substantially level with each other.

An insulator 503 is provided over the conductor 463 and the insulator 501. A conductor 465 is embedded in the insulator 503. The top surface of the conductor 465 and the top surface of the insulator 503 can be substantially level with each other.

An insulator 505 is provided over the conductor 465 and the insulator 503. A conductor 467 is embedded in the insulator 505. The conductor 467 can be provided in the same layer as the wirings 121 to 123 illustrated in FIG. 20, for example. Here, the top surface of the conductor 467 and the top surface of the insulator 505 can be substantially level with each other.

An insulator 507 is provided over the conductor 467 and the insulator 505. A conductor 469 is embedded in the insulator 507. Here, the top surface of the conductor 469 and the top surface of the insulator 507 can be substantially level with each other.

An insulator 509 is provided over the conductor 469 and the insulator 507. A conductor 471 is embedded in the insulator 509. The conductor 471 can be provided in the same layer as the wirings 141 to 143 illustrated in FIG. 20, for example. Here, the top surface of the conductor 471 and the top surface of the insulator 509 can be substantially level with each other.

The insulator 421 and the insulator 214 are provided over the conductor 471 and the insulator 509. The conductor 453 is embedded in the insulator 421 and the insulator 214. Here, the top surface of the conductor 453 and the top surface of the insulator 214 can be substantially level with each other.

As illustrated in FIG. 29 and FIG. 30, one of a source and a drain of the transistor 602 is electrically connected to the FPC 716 through the conductor 461, the conductor 463, the conductor 465, the conductor 467, the conductor 469, the conductor 471, the conductor 453, the conductor 455, the conductor 305, the conductor 317, the conductor 337, the conductor 347, the conductor 353, the conductor 355, the conductor 357, the connection electrode 760, and the anisotropic conductor 780.

The insulators 613, 614, 680, 674, 681, 501, 503, 505, 507, and 509 function as an interlayer film and may also function as a planarization film that covers unevenness thereunder.

When the display device 810 has the structure illustrated in FIG. 29 or FIG. 30, all the transistors in the display device 810 can be OS transistors while the frame and size of the display device 810 are reduced. Accordingly, the transistors provided in the layer 820 and the transistors provided in the layer 830 can be manufactured using the same apparatus, for example. Consequently, the manufacturing cost of the display device 810 can be reduced, making the display device 810 inexpensive.

<Structure Example 3 of Display Device>

Figure 31A:
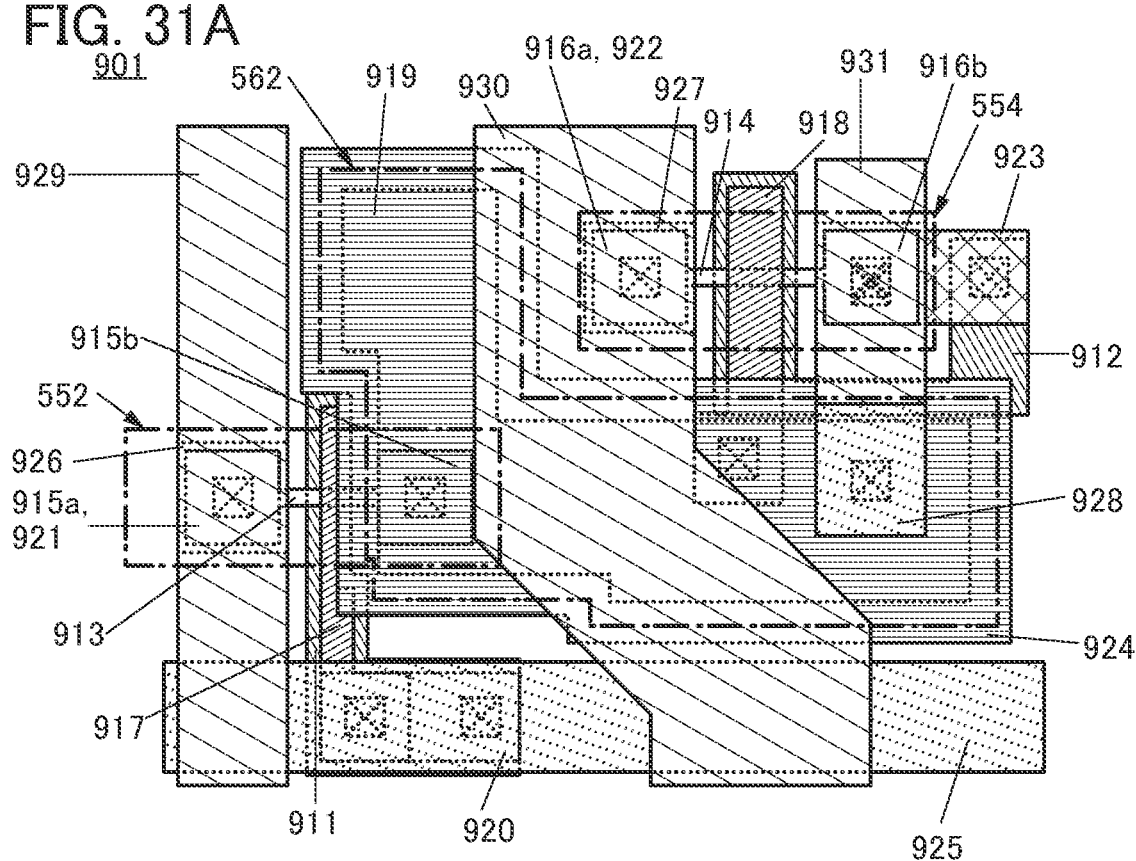
FIGS. 31A and 31B are top views illustrating a structure example of a pixel.
Figure 31B:
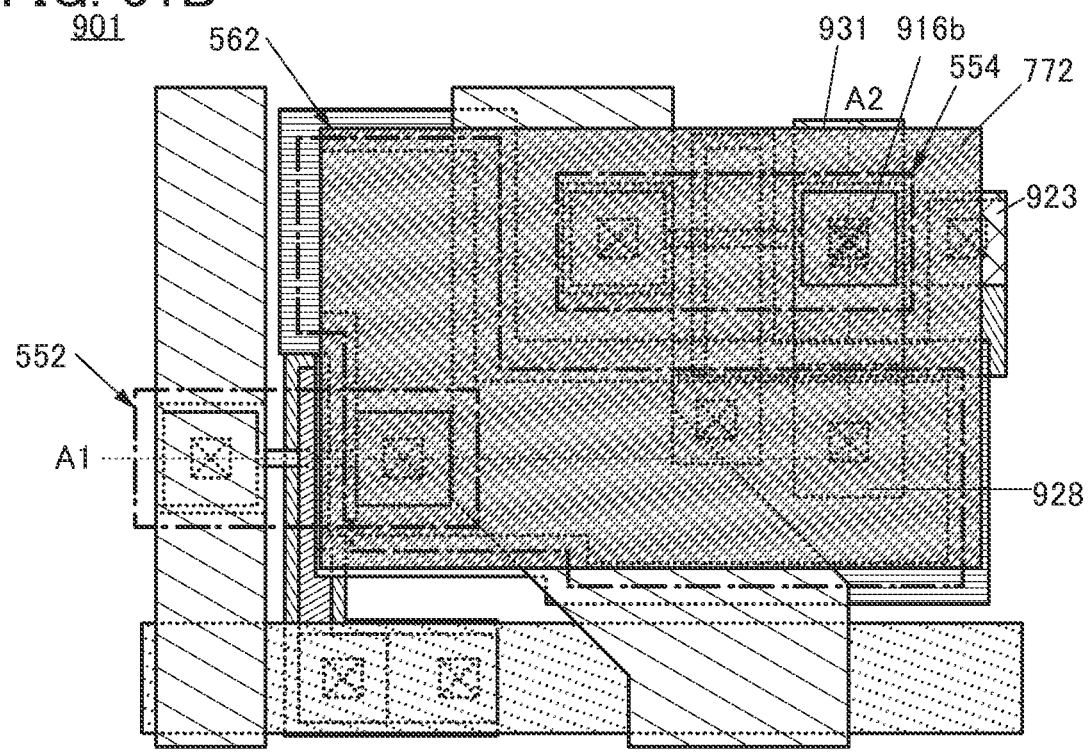

FIGS. 31A and 31B are top views illustrating structure examples of a subpixel 901 that can be used in the display device of one embodiment of the present invention. The subpixel 901 can have the circuit configuration illustrated in FIG. 22B. Here, the transistor 552 has a back gate in addition to a gate, and the back gate is electrically connected to the wiring 831. The transistor 554 has a back gate in addition to a gate, and the back gate is electrically connected to the other of the source and the drain of the transistor 554, the other electrode of the capacitor 562, and one electrode of the light-emitting element 572.

FIG. 31A illustrates conductors and semiconductors in the transistors, the capacitor, the wirings, and the like included in the subpixel 901. FIG. 31B illustrates the conductor 772 serving as one electrode of the light-emitting element 572, in addition to the components shown in FIG. 31A. Note that the conductor serving as the other electrode of the light-emitting element 572 is omitted in FIGS. 31A and 31B. Here, the one electrode of the light-emitting element 572 functions as a pixel electrode, and the other electrode of the light-emitting element 572 functions as a common electrode.

As illustrated in FIGS. 31A and 31B, the subpixel 901 includes a conductor 911, a conductor 912, a semiconductor 913, a semiconductor 914, a conductor 915a, a conductor 915b, a conductor 916a, a conductor 916b, a conductor 917, a conductor 918, a conductor 919, a conductor 920, a conductor 921, a conductor 922, a conductor 923, a conductor 924, a conductor 925, a conductor 926, a conductor 927, a conductor 928, a conductor 929, a conductor 930, a conductor 931, and the conductor 772.

The conductor 911 and the conductor 912 can be formed in the same step. The semiconductor 913 and the semiconductor 914 are formed in the same step and can be formed in a step after the formation of the conductors 911 and 912. The conductors 915a and 915b and the conductors 916a and 916b are formed in the same step and can be formed in a step after the formation of the conductors 911 and 912. The conductor 917 and the conductor 918 are formed in the same step and can be formed in a step after the formation of the semiconductors 913 and 914 and the conductors 915a, 915b, 916a, and 916b.

The conductors 919 to 923 are formed in the same step and can be formed in a step after the formation of the conductors 917 and 918. The conductor 924 can be formed in a step after the formation of the conductors 919 to 923. The conductors 925 to 928 are formed in the same step and can be formed in a step after the formation of the conductor 924. The conductors 929 to 931 are formed in the same step and can be formed in a step after the formation of the conductors 925 to 928. The conductor 772 can be formed in a step after the formation of the conductors 929 to 931.

In this specification and the like, it can be said that components formed in the same step are provided in one layer. For example, since the conductor 911 and the conductor 912 can be formed in the same step, it can be said that the conductor 911 and the conductor 912 are provided in the same layer. In addition, it can be said that components formed in a given step are provided above components formed in a step prior to the given step. For example, since the conductors 929 to 931 can be formed in a step after the formation of the conductors 925 to 928, it can be said that the conductors 929 to 931 are provided above the conductor 925 to 928.

The conductor 911 functions as the back gate electrode of the transistor 552. The semiconductor 913 includes a channel formation region of the transistor 552. The conductor 915a functions as one of the source electrode and the drain electrode of the transistor 552. The conductor 915b functions as the other of the source electrode and the drain electrode of the transistor 552. The conductor 917 functions as the gate electrode of the transistor 552.

The conductor 912 functions as the back gate electrode of the transistor 554. The semiconductor 914 includes a channel formation region of the transistor 554. The conductor 916a functions as one of the source electrode and the drain electrode of the transistor 554. The conductor 916b functions as the other of the source electrode and the drain electrode of the transistor 554. The conductor 918 functions as the gate electrode of the transistor 554.

The conductor 919 functions as one electrode of the capacitor 562. The conductor 924 functions as the other electrode of the capacitor 562. The conductor 925 corresponds to the wiring 831 functioning as a scan line. The conductor 929 corresponds to the wiring 832 functioning as a data line. The conductor 930 corresponds to the wiring 835a functioning as a power supply line. The conductor 772 functions as the one electrode of the light-emitting element 572 as described above.

The conductor 911 is electrically connected to the conductor 920. The conductor 912 is electrically connected to the conductor 923. The conductor 915a is electrically connected to the conductor 921. The conductor 915b is also electrically connected to the conductor 919. The conductor 916a is electrically connected to the conductor 922.

The conductor 916b is electrically connected to the conductor 923. That is, the conductor 912 functioning as the back gate electrode of the transistor 554 and the conductor 916b functioning as the other of the source electrode and the drain electrode of the transistor 554 are electrically connected to each other through the conductor 923.

The conductor 917 is electrically connected to the conductor 920. That is, the conductor 911 functioning as the back gate electrode of the transistor 552 and the conductor 917 functioning as the gate electrode of the transistor 552 are electrically connected to each other through the conductor 920.

The conductor 920 is electrically connected to the conductor 925. That is, the conductor 917 functioning as the gate electrode of the transistor 552 and the conductor 925 functioning as a scan line are electrically connected to each other through the conductor 920.

The conductor 918 is electrically connected to the conductor 919. The conductor 921 is electrically connected to the conductor 926. The conductor 922 is electrically connected to the conductor 927. The conductor 923 is electrically connected to the conductor 928. The conductor 924 is electrically connected to the conductor 928.

The conductor 926 is electrically connected to the conductor 929. That is, the conductor 915a functioning as one of the source electrode and the drain electrode of the transistor 552 and the conductor 929 functioning as a data line are electrically connected to each other through the conductor 921 and the conductor 926.

The conductor 927 is electrically connected to the conductor 930. That is, the conductor 916a functioning as one of the source electrode and the drain electrode of the transistor 554 and the conductor 930 functioning as a power supply line are electrically connected to each other through the conductor 922 and the conductor 927.

The conductor 928 is electrically connected to the conductor 931. The conductor 931 is electrically connected to the conductor 772.

The semiconductors 913 and 914 can contain a metal oxide, for example. Thus, the transistors 552 and 554 can be OS transistors.

Figure 32:
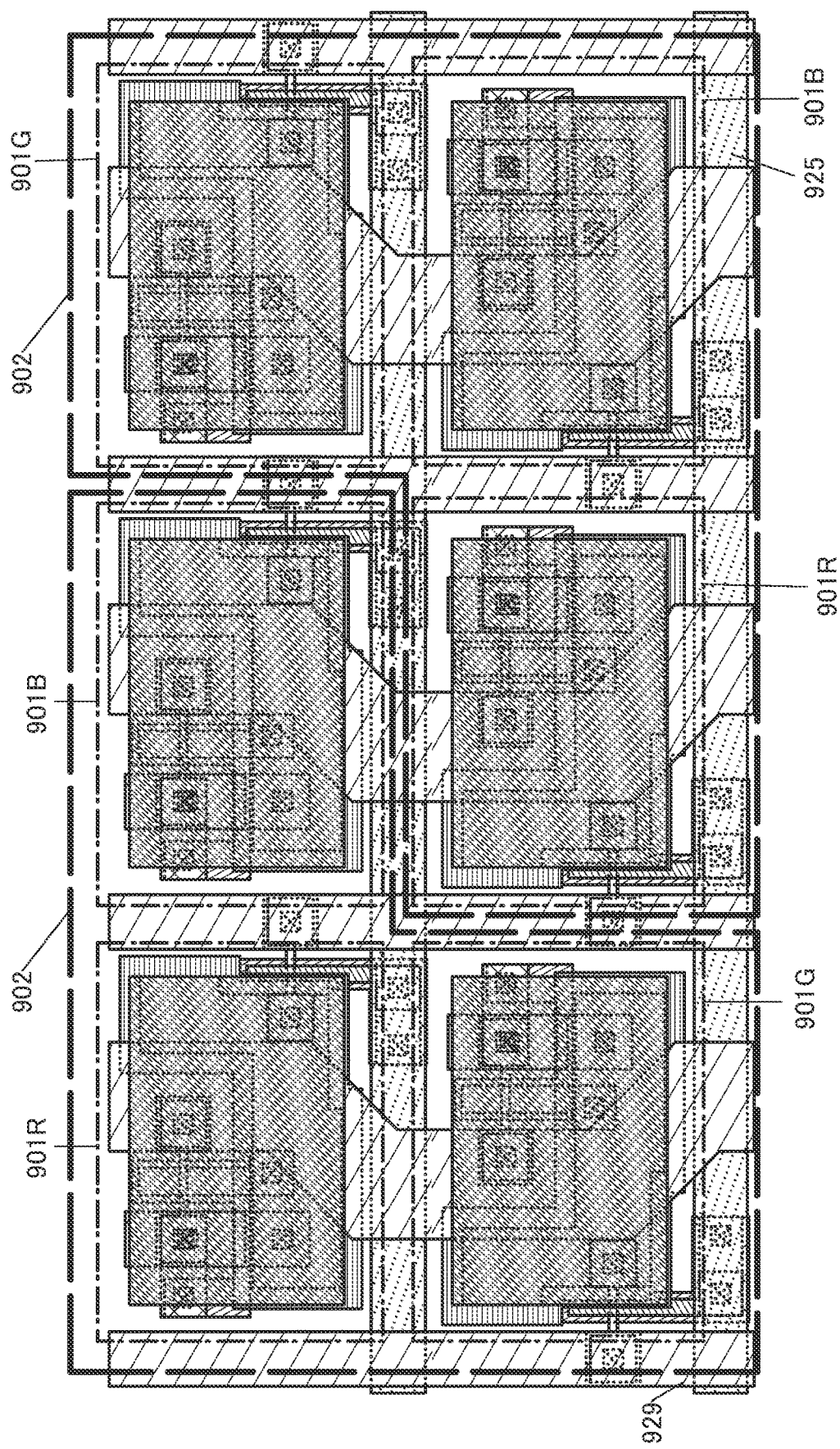
FIG. 32 is a top view illustrating a structure example of pixels.

FIG. 32 is a top view illustrating a structure example of a pixel 902 composed of subpixels 901 having the structure in FIG. 31B. In FIG. 32, a subpixel 901R indicates the subpixel 901 having a function of emitting red light, a subpixel 901G indicates the subpixel 901 having a function of emitting green light, and a subpixel 901B indicates the subpixel 901 having a function of emitting blue light. As illustrated in FIG. 32, the pixel 902 includes the subpixel 901R, the subpixel 901G, and the subpixel 901B. Specifically, one pixel 902 is composed of the subpixel 901R and the subpixel 901B that are placed on the upper side of the diagram, and the subpixel 901G placed on the lower side. Another pixel 902 is composed of the subpixel 901G placed on the upper side, and the subpixel 901R and the subpixel 901B that are placed on the lower side.

In FIG. 32, the subpixels 901R, 901G, and 901B on the upper side are laterally inverted with respect to the subpixels 901R, 901G, and 901B on the lower side. With such a structure, the subpixels 901 of the same color can be alternately arranged in the direction where the conductor 925 functioning as a scan line extends. Thus, the subpixels 901 having a function of emitting light of the same color can be electrically connected to one data line. That is, two or more kinds of subpixels 901 selected from the subpixels 901R, 901G, and 901B can be prevented from being electrically connected to one data line.

Figure 33:
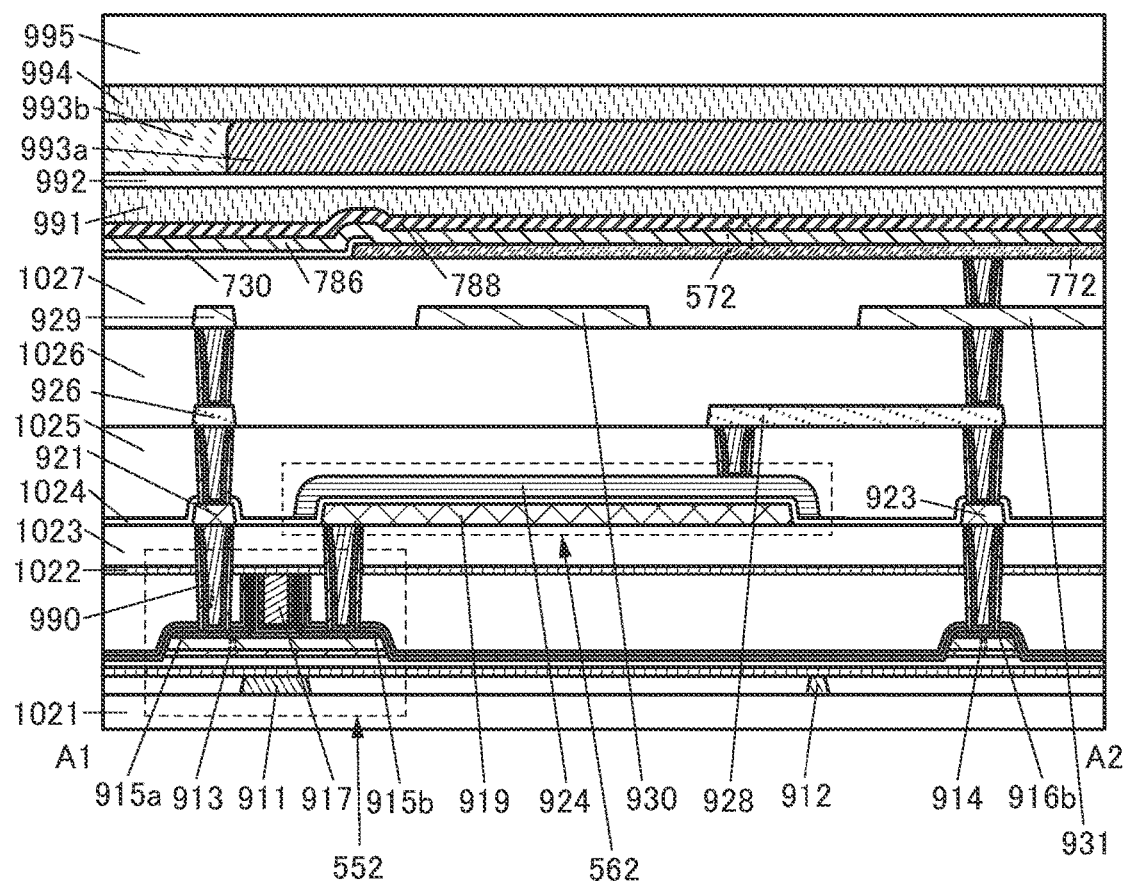
FIG. 33 is a cross-sectional view illustrating a structure example of a pixel.

FIG. 33 is a cross-sectional view along the dashed-dotted line A1-A2 in FIG. 31B. The transistor 552 and the transistor 554 are provided over an insulator 1021. An insulator 1022 is provided over the transistor 552 and the transistor 554, and an insulator 1023 is provided over the insulator 1022. Note that a substrate is provided below the insulator 1021. The components in the layer 820 illustrated in FIG. 8 and the like (e.g., the gate driver circuit 821, the source driver circuit 822, and the circuit 840) can be provided between the substrate and the insulator 1021.

As illustrated in FIG. 33, the conductors provided in different layers are electrically connected to each other through a conductor 990 functioning as a plug. For example, the conductor 915a and the conductor 921 provided above the conductor 915a are electrically connected to each other through the conductor 990. The conductor 990 can have a structure similar to that of the conductors 453, 305, 337, 353, 355, 357, 301a, 301b, 331, 351, 333, and 335 illustrated in FIG. 27 and the like.

An insulator 1024 is provided over the conductor 919 to 923 and the insulator 1023. The conductor 924 is provided over the insulator 1024. The conductor 919, the insulator 1024, and the conductor 924 form the capacitor 562.

An insulator 1025 is provided over the conductor 924 and the insulator 1024. An insulator 1026 is provided over the conductors 925 to 928 and the insulator 1025. An insulator 1027 is provided over the conductors 929 to 931 and the insulator 1026.

The conductor 772 and the insulator 730 are provided over the insulator 1027. Here, the insulator 730 can cover part of the conductor 772. The conductor 772, the EL layer 786, and the conductor 788 form the light-emitting element 572.

A bonding layer 991 is provided over the conductor 788, and an insulator 992 is provided over the bonding layer 991.

The insulator 992 over the bonding layer 991 can be formed in the following manner. First, the insulator 992 is formed over a substrate different from the substrate where the light-emitting element 572 and the like are formed. Next, the conductor 788 and the insulator 992 are bonded to each other with the bonding layer 991. After that, the substrate where the insulator 992 is formed is separated. Through the above steps, the insulator 992 can be formed over the conductor 788.

A coloring layer 993 is provided over the insulator 992. FIG. 33 illustrates a coloring layer 993a and a coloring layer 993b as the coloring layer 993. A substrate 995 is attached onto the coloring layer 993 with a bonding layer 994.

The coloring layer 993b has a function of transmitting light of a color that is different from the color of light that the coloring layer 993a transmits. For example, when the pixel 902 includes the subpixel 901R with a function of emitting red light, the subpixel 901G with a function of emitting green light, and the subpixel 901B with a function of transmitting blue light and the coloring layer 993a has a function of transmitting red light, the coloring layer 993b has a function of transmitting green light or blue light.

Forming the coloring layer 993 over the insulator 992 facilitates alignment between the coloring layer 993 and the light-emitting element 572. Thus, the definition of the display device of one embodiment of the present invention can be increased.

<Structure Example 4 of Display Device>

Figure 34A:
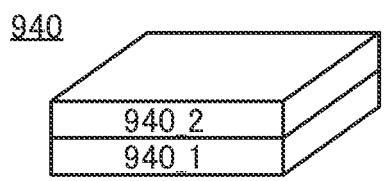
FIG. 34A is a schematic diagram illustrating a structure example of a pixel.

FIG. 34A is a schematic diagram illustrating a structure example of a subpixel 940 that can be used in the display device of one embodiment of the present invention. The subpixel 940 can have a stacked-layer structure of a subpixel 940_1 and a subpixel 940_2. The subpixel 940 can have the circuit configuration illustrated in FIG. 24E. Here, each of the transistors 511 and 529 has a back gate in addition to a gate, and their back gates are electrically connected to the wiring 831_1. The transistor 513 has a back gate, and the back gate is electrically connected to the wiring 8312. The transistor 521 has a back gate, and the back gate is electrically connected to the other electrode of the capacitor 517 and one electrode of the light-emitting element 572.

Figure 34B:
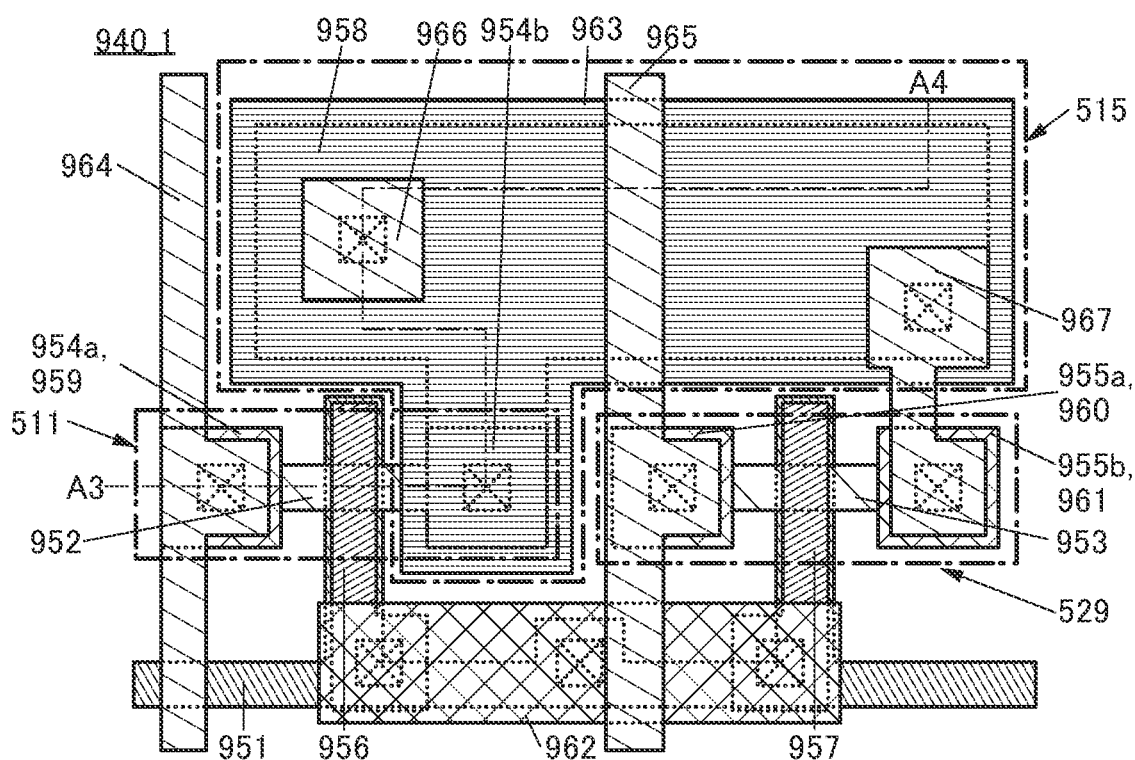
FIG. 34B is a top view of a structure example of a pixel.

FIG. 34B is a top view illustrating a structure example of the subpixel 940_1. FIG. 34B illustrates conductors and semiconductors in the transistors, the capacitor, the wirings, and the like included in the subpixel 940_1.

As illustrated in FIG. 34B, the subpixel 940_1 includes a conductor 951, a semiconductor 952, a semiconductor 953, a conductor 954a, a conductor 954b, a conductor 955a, a conductor 955b, a conductor 956, a conductor 957, a conductor 958, a conductor 959, a conductor 960, a conductor 961, a conductor 962, a conductor 963, a conductor 964, a conductor 965, a conductor 966, and a conductor 967.

The semiconductor 952 and the semiconductor 953 are formed in the same step and can be formed in a step after the formation of the conductor 951. The conductors 954a and 954b and the conductors 955a and 955b are formed in the same step and can be formed in a step after the formation of the conductor 951. The conductor 956 and the conductor 957 are formed in the same step and can be formed in a step after the formation of the semiconductors 952 and 953 and the conductors 954a, 954b, 955a, and 955b.

The conductors 958 to 962 are formed in the same step and can be formed in a step after the formation of the conductors 956 and 957. The conductor 963 can be formed in a step after the formation of the conductors 958 to 962.

The conductors 964 to 967 are formed in the same step and can be formed in a step after the formation of the conductor 963.

The conductor 951 has a function of the back gate electrode of each of the transistors 511 and 529. Moreover, the conductor 951 corresponds to the wiring 831_1 functioning as a scan line.

The semiconductor 952 includes a channel formation region of the transistor 511. The conductor 954a functions as one of the source electrode and the drain electrode of the transistor 511. The conductor 954b functions as the other of the source electrode and the drain electrode of the transistor 511. The conductor 956 functions as the gate electrode of the transistor 511.

The semiconductor 953 includes a channel formation region of the transistor 529. The conductor 955a functions as one of the source electrode and the drain electrode of the transistor 529. The conductor 955b functions as the other of the source electrode and the drain electrode of the transistor 529. The conductor 957 functions as the gate electrode of the transistor 529.

The conductor 958 functions as one electrode of the capacitor 515. The conductor 963 functions as the other electrode of the capacitor 515. The conductor 964 corresponds to the wiring 832_1 functioning as a data line. The conductor 965 corresponds to the wiring 543 functioning as a power supply line.

The conductor 951 is electrically connected to the conductor 962. The conductor 954a is electrically connected to the conductor 959. The conductor 954b is electrically connected to the conductor 958. The conductor 955a is electrically connected to the conductor 960. The conductor 955b is electrically connected to the conductor 961.

The conductor 956 and the conductor 957 are electrically connected to the conductor 962. That is, the conductor 951, which functions as the back gate electrode of each of the transistors 511 and 529 and corresponds to the wiring 831_1 serving as a scan line, is electrically connected to the conductor 956 functioning as the gate electrode of the transistor 511 and the conductor 957 functioning as the gate electrode of the transistor 529 through the conductor 962.

The conductor 959 is electrically connected to the conductor 964. That is, the conductor 954a functioning as one of the source and the drain of the transistor 511 and the conductor 964 functioning as a data line are electrically connected to each other through the conductor 959.

The conductor 960 is electrically connected to the conductor 965. That is, the conductor 955a functioning as one of the source and the drain of the transistor 529 and the conductor 965 functioning as a power supply line are electrically connected to each other through the conductor 960.

The conductor 961 is electrically connected to the conductor 967. The conductor 963 is electrically connected to the conductor 966.

The semiconductors 952 and 953 can contain a metal oxide, for example. Thus, the transistors 511 and 529 can be OS transistors.

Figure 35A:
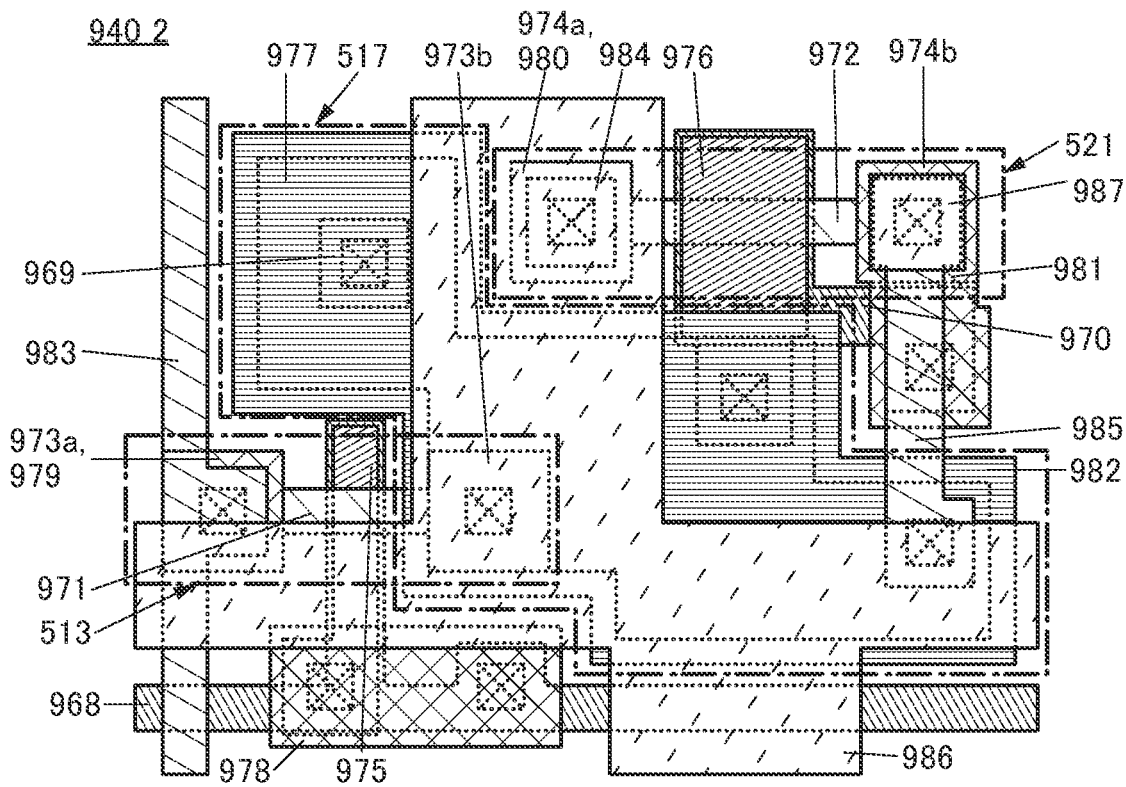
FIGS. 35A and 35B are top views illustrating a structure example of a pixel.
Figure 35B:
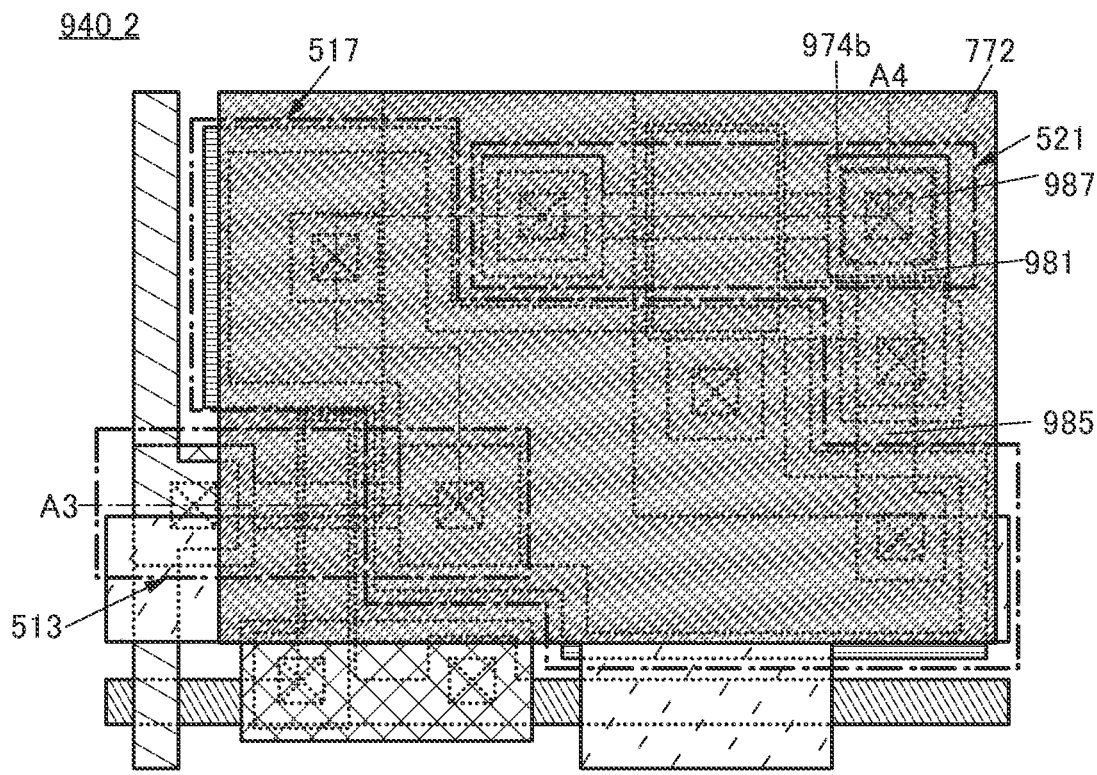

FIG. 35A illustrates conductors and semiconductors in the transistors, the capacitor, the wirings, and the like included in the subpixel 9402. FIG. 35B illustrates the conductor 772 serving as one electrode of the light-emitting element 572, in addition to the components shown in FIG. 35A. Note that the conductor serving as the other electrode of the light-emitting element 572 is omitted in FIGS. 35A and 35B.

As illustrated in FIGS. 35A and 35B, the subpixel 9402 includes a conductor 968, a conductor 969, a conductor 970, a semiconductor 971, a semiconductor 972, a conductor 973a, a conductor 973b, a conductor 974a, a conductor 974b, a conductor 975, a conductor 976, a conductor 977, a conductor 978, a conductor 979, a conductor 980, a conductor 981, a conductor 982, a conductor 983, a conductor 984, a conductor 985, a conductor 986, a conductor 987, and the conductor 772.

The conductors 968 to 970 can be formed in the same step. The semiconductors 971 and 972 are formed in the same step and can be formed in a step after the formation of the conductors 968 to 970. The conductors 973a and 973b and the conductors 974a and 974b are formed in the same step and can be formed in a step after the formation of the conductors 968 to 970. The conductors 975 and 976 are formed in the same step and can be formed in a step after the formation of the semiconductors 971 and 972 and the conductors 973a, 973b, 974a, and 974b.

The conductors 977 to 981 are formed in the same step and can be formed in a step after the formation of the conductors 975 and 976. The conductor 982 can be formed in a step after the formation of the conductors 977 to 981. The conductors 983 to 985 are formed in the same step and can be formed in a step after the formation of the conductor 982. The conductors 986 and 987 are formed in the same step and can be formed in a step after the formation of the conductors 983 to 985. The conductor 772 can be formed in a step after the formation of the conductors 986 and 987.

The conductor 968 has a function of the back gate electrode of the transistor 513 and corresponds to the wiring 831_2 serving as a scan line. The semiconductor 971 includes a channel formation region of the transistor 513. The conductor 973a functions as one of the source electrode and the drain electrode of the transistor 513. The conductor 973b functions as the other of the source electrode and the drain electrode of the transistor 513. The conductor 975 functions as the gate electrode of the transistor 513.

The conductor 970 functions as the back gate electrode of the transistor 521. The semiconductor 972 includes a channel formation region of the transistor 521. The conductor 974a functions as one of the source electrode and the drain electrode of the transistor 521. The conductor 974b functions as the other of the source electrode and the drain electrode of the transistor 521. The conductor 976 functions as the gate electrode of the transistor 521.

The conductor 977 functions as one electrode of the capacitor 517. The conductor 982 functions as the other electrode of the capacitor 517. The conductor 983 corresponds to the wiring 832_2 functioning as a data line. The conductor 986 corresponds to the wiring 537 functioning as a power supply line. The conductor 772 functions as the one electrode of the light-emitting element 572 as described above.

The conductor 968 is electrically connected to the conductor 978. The conductor 969 is electrically connected to the conductor 977. The conductor 970 is electrically connected to the conductor 981. The conductor 973a is electrically connected to the conductor 979. The conductor 973b is electrically connected to the conductor 977. The conductor 974a is electrically connected to the conductor 980.

The conductor 974b is electrically connected to the conductor 981. That is, the conductor 970 functioning as the back gate electrode of the transistor 521 and the conductor 974b functioning as the other of the source electrode and the drain electrode of the transistor 521 are electrically connected to each other through the conductor 981.

The conductor 975 is electrically connected to the conductor 978. That is, the conductor 968 functioning as the back gate electrode of the transistor 513 and the conductor 975 functioning as the gate electrode of the transistor 513 are electrically connected to each other through the conductor 978. The conductor 976 is electrically connected to the conductor 977.

The conductor 979 is electrically connected to the conductor 983. That is, the conductor 973a functioning as one of the source and the drain of the transistor 513 and the conductor 983 functioning as a data line are electrically connected to each other through the conductor 979.

The conductor 980 is electrically connected to the conductor 984. The conductor 981 is electrically connected to the conductor 985. The conductor 982 is electrically connected to the conductor 985.

The conductor 984 is electrically connected to the conductor 986. That is, the conductor 974a functioning as one of the source electrode and the drain electrode of the transistor 521 and the conductor 986 functioning as a power supply line are electrically connected to each other through the conductor 980 and the conductor 984.

The conductor 985 is electrically connected to the conductor 987. The conductor 987 is electrically connected to the conductor 772.

The semiconductors 971 and 972 can contain a metal oxide, for example. Thus, the transistors 513 and 521 can be OS transistors.

Figure 36:
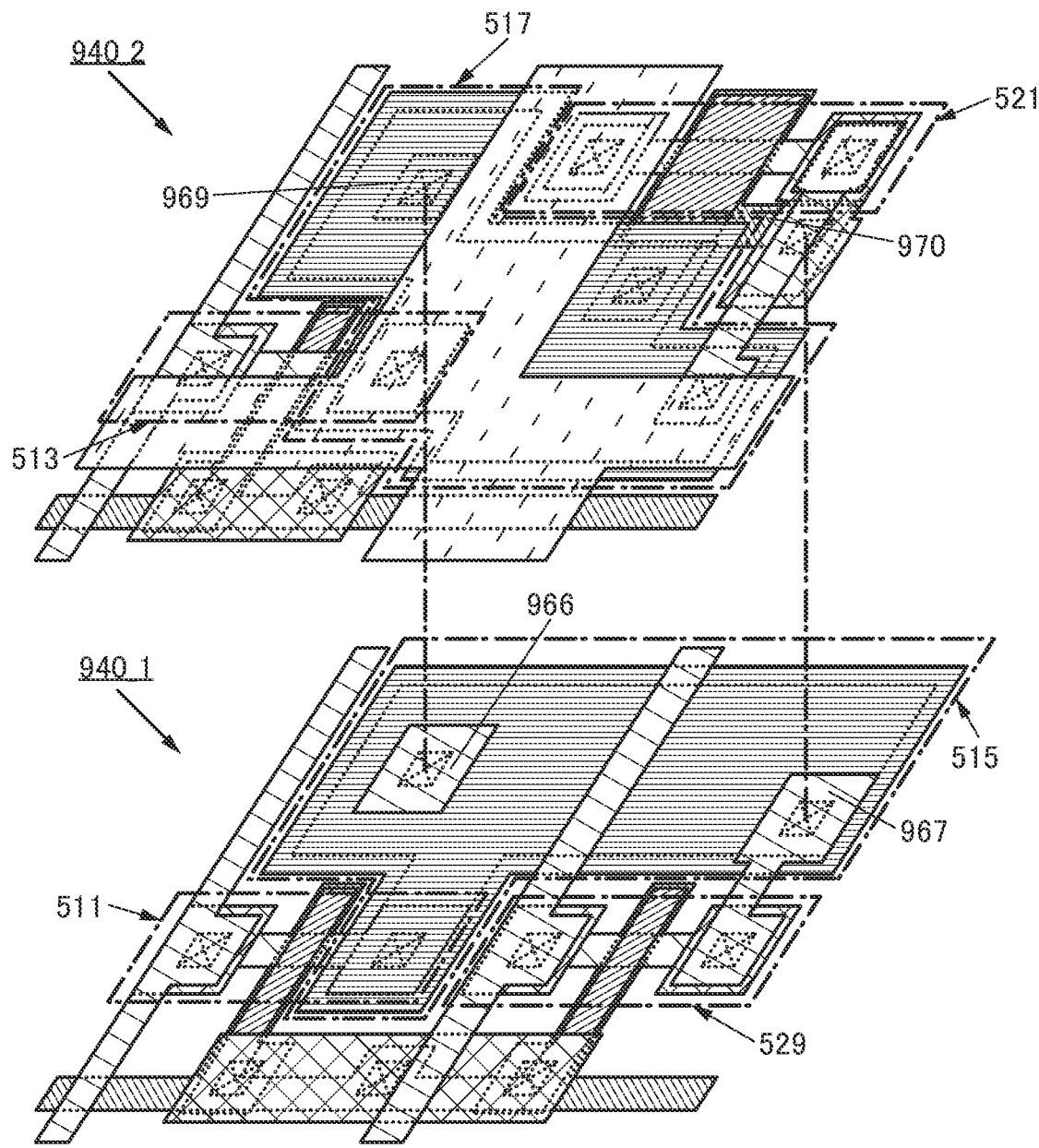
FIG. 36 is a top view illustrating a structure example of a pixel.

FIG. 36 is a top view illustrating a stacked-layer structure of the subpixel 940_1 and the subpixel 940_2, and shows the electrical connection relation between the subpixel 940_1 and the subpixel 940_2. For simplification, the conductor 772 that functions as a pixel electrode and is provided in the subpixel 940_2 is not illustrated in FIG. 36.

As illustrated in FIG. 36, the conductor 966 provided in the subpixel 940_1 and the conductor 969 provided in the subpixel 940_2 are electrically connected to each other. Thus, the other electrode of the capacitor 515 provided in the subpixel 940_1 can be electrically connected to the other of the source and the drain of the transistor 513, the gate of the transistor 521, and one electrode of the capacitor 517 that are provided in the subpixel 940_2. The conductor 967 provided in the subpixel 940_1 and the conductor 970 provided in the subpixel 940_2 are electrically connected to each other. Thus, the other of the source and the drain of the transistor 529 provided in the subpixel 940_1 can be electrically connected to the other electrode of the capacitor 517, the other of the source and the drain of the transistor 521, and one electrode of the light-emitting element 572 that are provided in the subpixel 940_2.

Figure 37:
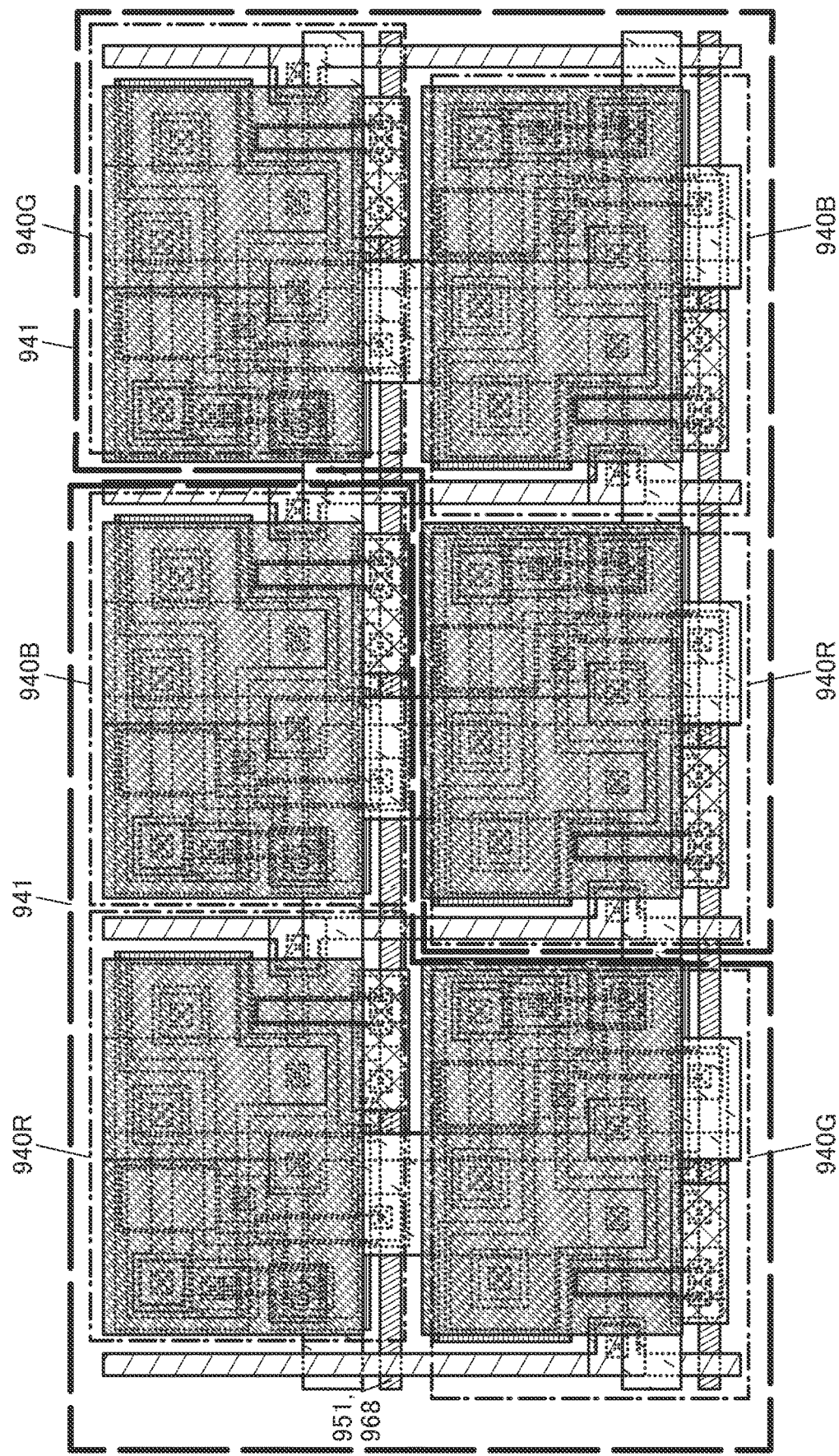
FIG. 37 is a top view illustrating a structure example of pixels.

FIG. 37 is a top view illustrating a structure example of a pixel 941 composed of the subpixels 940 having the structure in FIG. 34B or FIG. 35B. In FIG. 37, a subpixel 940R indicates the subpixel 940 having a function of emitting red light, a subpixel 940G indicates the subpixel 940 having a function of emitting green light, and a subpixel 940B indicates the subpixel 940 having a function of emitting blue light. As illustrated in FIG. 37, the pixel 941 includes the subpixel 940R, the subpixel 940G, and the subpixel 940B. Specifically, one pixel 941 is composed of the subpixel 940R and the subpixel 940B that are placed on the upper side of the diagram, and the subpixel 940G placed on the lower side. Another pixel 941 is composed of the subpixel 940G placed on the upper side, and the subpixel 940R and the subpixel 940B that are placed on the lower side.

In FIG. 37, the subpixels 940R, 940G, and 940B on the upper side are laterally inverted with respect to the subpixels 940R, 940G, and 940B on the lower side. With such a structure, the subpixels 940 of the same color can be alternately arranged in the direction where the conductors 951 and 968 functioning as scan lines extend. Thus, the subpixels 940 having a function of emitting light of the same color can be electrically connected to one data line. That is, two or more kinds of subpixels 940 selected from the subpixels 940R, 940G, and 940B can be prevented from being electrically connected to one data line.

Figure 38:
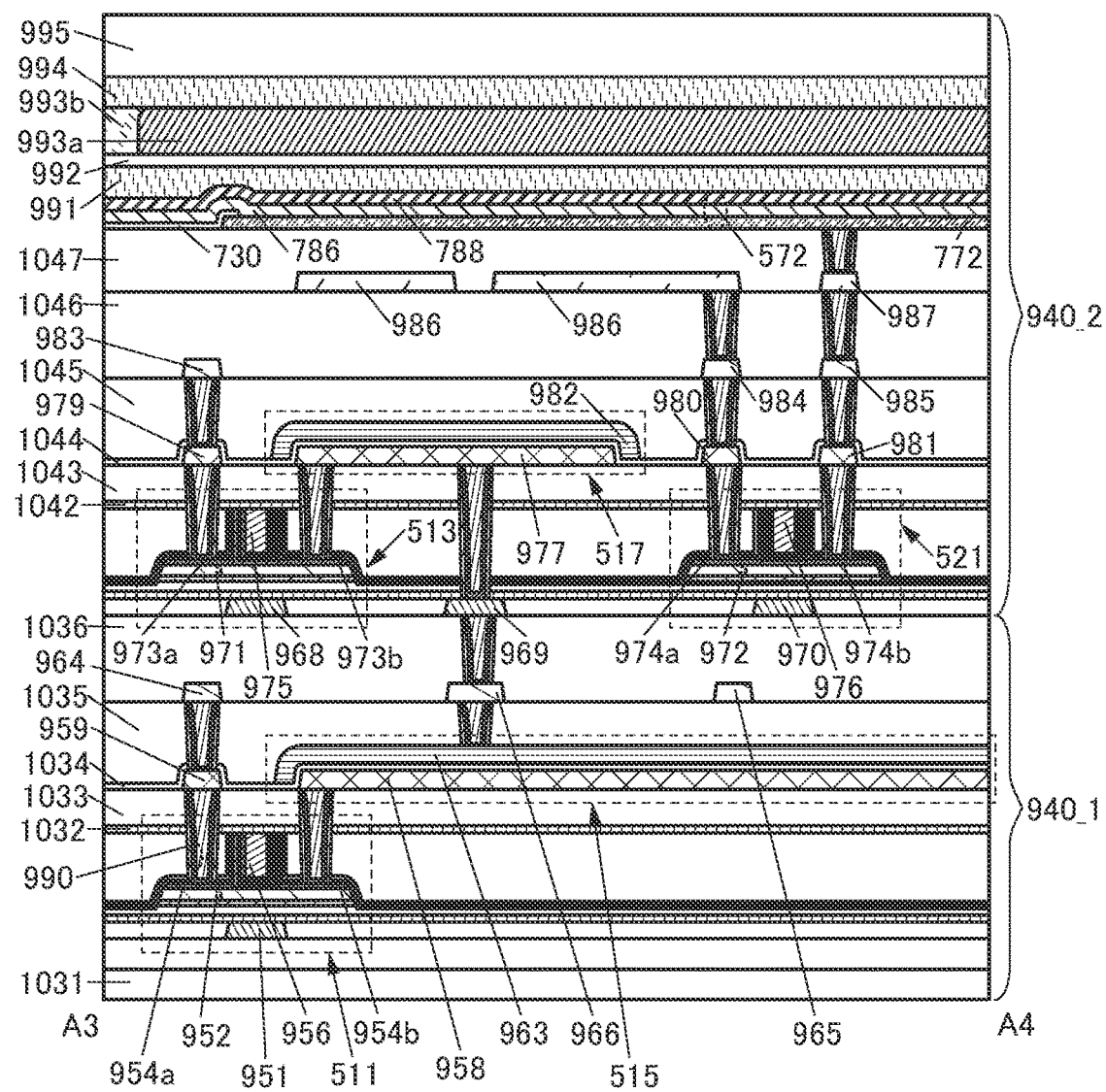
FIG. 38 is a cross-sectional view illustrating a structure example of a pixel.

FIG. 38 is a cross-sectional view along the dashed-dotted line A3-A4 in FIG. 34B and FIG. 35B. The transistor 511 and the transistor 529, which are the transistors provided in the subpixel 940_1, are provided over an insulator 1031. An insulator 1032 is provided over the transistor 511 and the transistor 529, and an insulator 1033 is provided over the insulator 1032. Note that a substrate is provided below the insulator 1031. The components in the layer 820 illustrated in FIG. 8 and the like (e.g., the gate driver circuit 821, the source driver circuit 822, and the circuit 840) can be provided between the substrate and the insulator 1031.

As illustrated in FIG. 38, the conductors provided in different layers are electrically connected to each other through the conductor 990 functioning as a plug.

An insulator 1034 is provided over the conductor 958 to 962 and the insulator 1033. The conductor 963 is provided over the insulator 1034. The conductor 958, the insulator 1034, and the conductor 963 form the capacitor 515.

An insulator 1035 is provided over the conductor 963 and the insulator 1034. An insulator 1036 is provided over the conductors 964 to 967.

The transistor 513 and the transistor 521, which are the transistors provided in the subpixel 940_2, are provided over the insulator 1036. An insulator 1042 is provided over the transistor 513 and the transistor 521, and an insulator 1043 is provided over the insulator 1042.

An insulator 1044 is provided over the conductors 977 to 981 and the insulator 1043. The conductor 982 is provided over the insulator 1044. The conductor 977, the insulator 1044, and the conductor 982 form the capacitor 517.

An insulator 1045 is provided over the conductor 982 and the insulator 1044. An insulator 1046 is provided over the conductors 983 to 985 and the insulator 1045. An insulator 1047 is provided over the conductor 986, the conductor 987, and the insulator 1046.

The conductor 772 and the insulator 730 are provided over the insulator 1047. Here, the insulator 730 can cover part of the conductor 772, as in FIG. 33. The conductor 772, the EL layer 786, and the conductor 788 form the light-emitting element 572.

As in FIG. 33, the bonding layer 991 is provided over the conductor 788, and the insulator 992 is provided over the bonding layer 991. The coloring layer 993 is provided over the insulator 992, and the substrate 995 is attached onto the coloring layer 993 with the bonding layer 994.

<Structure Example of Light-Emitting Element>

Figure 39A:
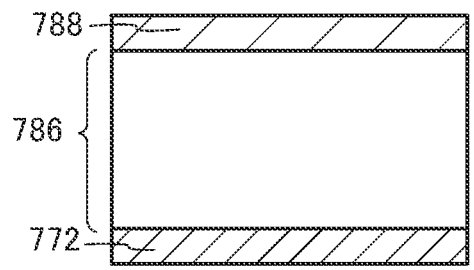
FIGS. 39A to 39E illustrate structure examples of a light-emitting element.

FIGS. 39A to 39E illustrate structure examples of the light-emitting element 572. FIG. 39A illustrates a structure where the EL layer 786 is positioned between the conductor 772 and the conductor 788 (a single structure). As described above, the EL layer 786 contains a light-emitting material, for example, a light-emitting material of an organic compound.

Figure 39B:
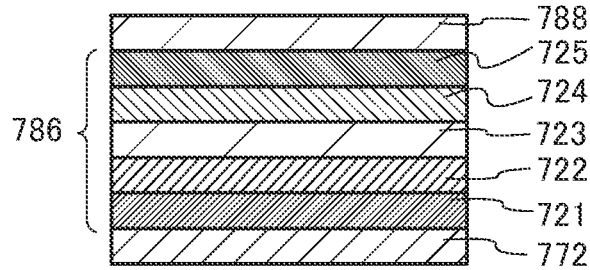

FIG. 39B illustrates a stacked-layer structure of the EL layer 786. In the light-emitting element 572 with the structure illustrated in FIG. 39B, the conductor 772 functions as an anode and the conductor 788 functions as a cathode.

The EL layer 786 has a structure in which a hole-injection layer 721, a hole-transport layer 722, a light-emitting layer 723, an electron-transport layer 724, and an electron-injection layer 725 are stacked in this order over the conductor 772. Note that the order of the stacked layers is reversed when the conductor 772 functions as a cathode and the conductor 788 functions as an anode.

The light-emitting layer 723 contains a light-emitting material and a plurality of materials in appropriate combination, so that fluorescence or phosphorescence of a desired emission color can be obtained. The light-emitting layer 723 may have a stacked-layer structure having different emission colors. In that case, the light-emitting substance and other substances are different between the stacked light-emitting layers.

For example, when the light-emitting element 572 has a micro optical resonator (microcavity) structure with the conductor 772 and the conductor 788 in FIG. 39B serving as a reflective electrode and a transflective electrode, respectively, light emitted from the light-emitting layer 723 in the EL layer 786 can be resonated between the electrodes and thus the light emitted through the conductor 788 can be intensified.

Note that when the conductor 772 of the light-emitting element 572 is a reflective electrode having a stacked-layer structure of a reflective conductive material and a light-transmitting conductive material (transparent conductive film), optical adjustment can be performed by controlling the thickness of the transparent conductive film. Specifically, when the wavelength of light from the light-emitting layer 723 is $\lambda$, the distance between the conductor 772 and the conductor 788 is preferably adjusted to around $m\lambda/2$ (m is a natural number).

To amplify desired light (wavelength: $\lambda$) obtained from the light-emitting layer 723, the optical path length from the conductor 772 to a region where desired light is obtained in the light-emitting layer 723 (light-emitting region) and the optical path length from the conductor 788 to the region where desired light is obtained in the light-emitting layer 723 (light-emitting region) are preferably adjusted to around $(2m'+1)\lambda/4$ (m' is a natural number). Here, the light-emitting region means a region where holes and electrons are recombined in the light-emitting layer 723.

By such optical adjustment, the spectrum of specific monochromatic light emitted from the light-emitting layer 723 can be narrowed and light emission with high color purity can be obtained.

In the above case, the optical path length between the conductor 772 and the conductor 788 is, to be exact, the total thickness between a reflective region in the conductor 772 and a reflective region in the conductor 788. However, it is difficult to precisely determine the reflection region in the conductors 772 and 788; hence, it is assumed that the above effect is adequately obtained wherever the reflective region is placed in the conductors 772 and 788. Furthermore, the optical path length between the conductor 772 and the light-emitting layer emitting desired light is, to be exact, the optical path length between the reflective region in the conductor 772 and the light-emitting region where desired light is obtained in the light-emitting layer. However, it is difficult to precisely determine the reflective region in the conductor 772 and the light-emitting region where desired light is obtained in the light-emitting layer; thus, it is assumed that the above effect is adequately obtained wherever the reflective region and the light-emitting region are placed in the conductor 772 and the light-emitting layer emitting desired light.

The light-emitting element 572 illustrated in FIG. 39B has a microcavity structure, so that light (monochromatic light)

with different wavelengths can be extracted from different light-emitting elements including the same EL layer. Thus, separate coloring for obtaining a plurality of emission colors (e.g., R, G, and B) is not necessary. Therefore, high definition can be easily achieved. Note that a combination of the structure in FIG. 39B with coloring layers is also possible. Furthermore, the emission intensity of light with a specific wavelength in the front direction can be increased, whereby power consumption can be reduced.

Note that the light-emitting element 572 illustrated in FIG. 39B does not necessarily have a microcavity structure. In the case where a microcavity structure is not employed, light of predetermined colors (e.g., RGB) can be extracted when the light-emitting layer 723 has a structure for emitting white light and coloring layers are provided. When the EL layers 786 are formed by separate coloring for obtaining different emission colors, light of predetermined colors can be extracted without providing coloring layers.

At least one of the conductors 772 and 788 can be a light-transmitting electrode (e.g., a transparent electrode or a transflective electrode). In the case where the light-transmitting electrode is a transparent electrode, the transparent electrode has a visible light transmittance of higher than or equal to 40%. In the case where the light-transmitting electrode is a transflective electrode, the transflective electrode has a visible light reflectance of higher than or equal to 20% and lower than or equal to 80%, preferably higher than or equal to 40% and lower than or equal to 70%. These electrodes preferably have a resistivity of $1\times10^{-2}$ Ωcm or less.

When the conductor 772 or the conductor 788 is an electrode having reflectivity (reflective electrode), the visible light reflectance of the reflective electrode is higher than or equal to 40% and lower than or equal to 100%, preferably higher than or equal to 70% and lower than or equal to 100%. This electrode preferably has a resistivity of $1\times10^{-2}$ Ωcm or less.

Figure 39C:
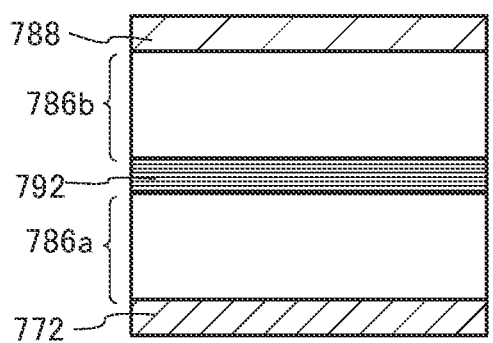

The light-emitting element 572 may have a structure illustrated in FIG. 39C. FIG. 39C illustrates the light-emitting element 572 having a stacked-layer structure (tandem structure) in which two EL layers (an EL layer 786a and an EL layer 786b) are provided between the conductor 772 and the conductor 788, and a charge generation layer 792 is provided between the EL layer 786a and the EL layer 786b. When the light-emitting element 572 has the tandem structure, the current efficiency and external quantum efficiency of the light-emitting element 572 can be increased. Therefore, the display device 810 can display high-luminance images. Moreover, power consumption of the display device 810 can be reduced. Here, the EL layer 786a and the EL layer 786b can have a structure similar to that of the EL layer 786 illustrated in FIG. 39B.

The charge generation layer 792 has a function of injecting electrons into one of the EL layers 786a and 786b and injecting holes to the other of the EL layers 786a and 786b when a voltage is supplied between the conductor 772 and the conductor 788. Accordingly, when a voltage is supplied such that the potential of the conductor 772 becomes higher than the potential of the conductor 788, electrons are injected into the EL layer 786a from the charge generation layer 792 and holes are injected into the EL layer 786b from the charge generation layer 792.

Note that in terms of light extraction efficiency, the charge generation layer 792 preferably transmits visible light (specifically, the visible light transmittance of the charge generation layer 792 is preferably 40% or higher). The conductivity of the charge generation layer 792 may be lower than that of the conductor 772 or the conductor 788.

Figure 39D:
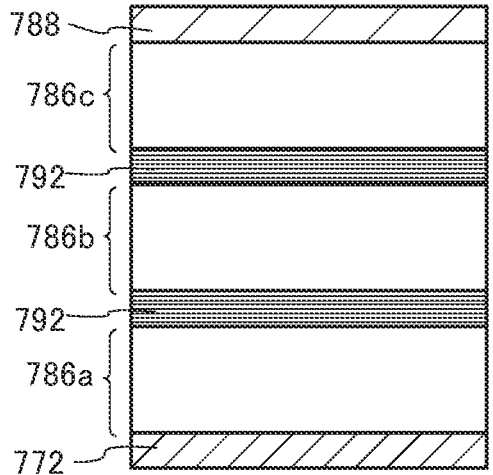

The light-emitting element 572 may have a structure illustrated in FIG. 39D. FIG. 39D illustrates the light-emitting element 572 having a tandem structure in which three EL layers (the EL layer 786a, the EL layer 786b, and an EL layer 786c) are provided between the conductor 772 and the conductor 788, and the charge generation layer 792 is provided between the EL layers 786a and 786b and between the EL layers 786b and 786c. Here, the EL layers 786a, 786b, and 786c can have a structure similar to that of the EL layer 786 illustrated in FIG. 39B. When the light-emitting element 572 has the structure illustrated in FIG. 39D, the current efficiency and external quantum efficiency of the light-emitting element 572 can be further increased. As a result, the display device 810 can display higher-luminance images. Moreover, power consumption of the display device 810 can be further reduced.

Figure 39E:
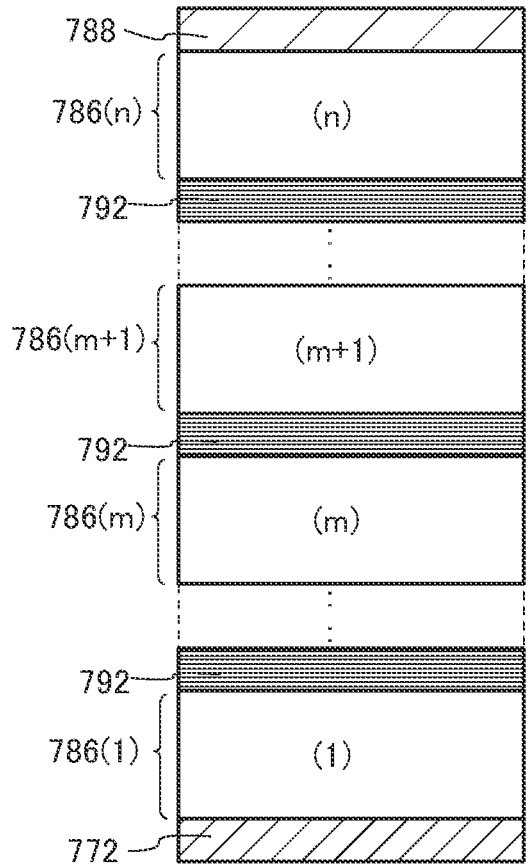

The light-emitting element 572 may have a structure illustrated in FIG. 39E. FIG. 39E illustrates the light-emitting element 572 having a tandem structure in which n EL layers (EL layers 786(1) to 786(n)) are provided between the conductor 772 and the conductor 788, and the charge generation layer 792 is provided between the EL layers 786. Here, the EL layers 786(1) to 786(n) can have a structure similar to that of the EL layer 786 illustrated in FIG. 39B. Note that FIG. 39E illustrates the EL layer 786(1), the EL layer 786(m), the EL layer 786(m+1), and the EL layer 786(n) among the EL layers 786. Here, m is an integer greater than or equal to 2 and less than n, and n is an integer greater than m. As n becomes larger, the current efficiency and external quantum efficiency of the light-emitting element 572 can be increased. As a result, the display device 810 can display high-luminance images. Moreover, power consumption of the display device 810 can be reduced.

<Materials for Light-Emitting Element>

Next, materials that can be used for the light-emitting element 572 will be described.

<<Conductor 772 and Conductor 788>>

For the conductors 772 and 788, any of the following materials can be used in an appropriate combination as long as the functions of the anode and the cathode can be fulfilled. For example, a metal, an alloy, an electrically conductive compound, a mixture of these, and the like can be appropriately used. Specifically, an In—Sn oxide (also referred to as ITO), an In—Si—Sn oxide (also referred to as ITSO), an In—Zn oxide, or an In—W—Zn oxide can be used. In addition, it is possible to use a metal such as aluminum (Al), titanium (Ti), chromium (Cr), manganese (Mn), iron (Fe), cobalt (Co), nickel (Ni), copper (Cu), gallium (Ga), zinc (Zn), indium (In), tin (Sn), molybdenum (Mo), tantalum (Ta), tungsten (W), palladium (Pd), gold (Au), platinum (Pt), silver (Ag), yttrium (Y), or neodymium (Nd) or an alloy containing an appropriate combination of any of these metals. It is also possible to use a Group 1 element or a Group 2 element in the periodic table, which is not described above (e.g., lithium (Li), cesium (Cs), calcium (Ca), or strontium (Sr)), a rare earth metal such as europium (Eu) or ytterbium (Yb), an alloy containing an appropriate combination of any of these elements, graphene, or the like.

<<Hole-Injection Layer 721 and Hole-Transport Layer 722>>

The hole-injection layer 721 injects holes to the EL layer 786 from the conductor 772, which is an anode, or the charge generation layer 792 and contains a material with a high hole-injection property. Here, the EL layer 786 includes the EL layer 786*a*, the EL layer 786*b*, the EL layer 786*c*, and the EL layer 786(1) to 786(*n*).

Examples of the material with a high hole-injection property include transition metal oxides such as molybdenum oxide, vanadium oxide, ruthenium oxide, tungsten oxide, and manganese oxide. Alternatively, it is possible to use any of the following materials: phthalocyanine-based compounds such as phthalocyanine (abbreviation: H$_2$Pc) and copper phthalocyanine (abbreviation: CuPc); aromatic amine compounds such as 4,4'-bis[N-(4-diphenylaminophenyl)-N-phenylamino]biphenyl (abbreviation: DPAB) and N,N'-bis-{4-[bis(3-methylphenyl)amino]phenyl}-N,N'-diphenyl-(1,1'-biphenyl)-4,4'-diamine (abbreviation: DNTPD); high molecular compounds such as poly(3,4-ethylenedioxythiophene)/poly(styrenesulfonic acid) (abbreviation: PEDOT/PSS); and the like.

Alternatively, as the material with a high hole-injection property, a composite material containing a hole-transport material and an acceptor material (electron-accepting material) can be used. In that case, the acceptor material extracts electrons from the hole-transport material, so that holes are generated in the hole-injection layer 721 and the holes are injected into the light-emitting layer 723 through the hole-transport layer 722. Note that the hole-injection layer 721 may be formed to have a single-layer structure using a composite material containing a hole-transport material and an acceptor material (electron-accepting material), or a stacked-layer structure in which a layer containing a hole-transport material and a layer containing an acceptor material (electron-accepting material) are stacked.

The hole-transport layer 722 transports the holes, which are injected from the conductor 772 by the hole-injection layer 721, to the light-emitting layer 723. Note that the hole-transport layer 722 contains a hole-transport material. It is particularly preferable that the HOMO level of the hole-transport material used for the hole-transport layer 722 be the same as or close to that of the hole-injection layer 721.

Examples of the acceptor material used for the hole-injection layer 721 include oxides of a metal belonging to any of Group 4 to Group 8 of the periodic table. Specific examples include molybdenum oxide, vanadium oxide, niobium oxide, tantalum oxide, chromium oxide, tungsten oxide, manganese oxide, and rhenium oxide. Among these oxides, molybdenum oxide is especially preferable since it is stable in the air, has a low hygroscopic property, and is easy to handle. Alternatively, organic acceptors such as a quinodimethane derivative, a chloranil derivative, and a hexaazatriphenylene derivative can be used. Specifically, 7,7,8,8-tetracyano-2,3,5,6-tetrafluoroquinodimethane (abbreviation: F$_4$-TCNQ), chloranil, 2,3,6,7,10,11-hexacyano-1,4,5,8,9,12-hexaazatriphenylene (abbreviation: HAT-CN), and the like can be used.

The hole-transport materials used for the hole-injection layer 721 and the hole-transport layer 722 are preferably substances with a hole mobility of greater than or equal to $10^{-6}$ cm$^2$/Vs. Note that other substances can also be used as long as the substances have a hole-transport property higher than an electron-transport property.

Preferred hole-transport materials are π-electron rich heteroaromatic compounds (e.g., carbazole derivatives and indole derivatives) and aromatic amine compounds. Specific examples include compounds having an aromatic amine skeleton, such as 4,4'-bis[N-(1-naphthyl)-N-phenylamino]biphenyl (abbreviation: NPB or α-NPD), N,N-bis(3-methylphenyl)-N,N-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 3-[4-(9-phenanthryl)-phenyl]-9-phenyl-9H-carbazole (abbreviation: PCPPn), N-(4-biphenyl)-N-(9,9-dimethyl-9H-fluoren-2-yl)-9-phenyl-9H-carbazol-3-amine (abbreviation: PCBiF), N-(1,1'-biphenyl-4-yl)-N-[4-(9-phenyl-9H-carbazol-3-yl)phenyl]-9,9-dimethyl-9H-fluoren-2-amine (abbreviation: PCBBiF), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), N-phenyl-N-[4-(9-phenyl-9H-carbazol-3-yl)phenyl]spiro-9,9'-bifluoren-2-amine (abbreviation: PCBASF), 4,4',4"-tris(carbazol-9-yl)triphenylamine (abbreviation: TCTA), 4,4',4"-tris(N,N-diphenylamino)triphenylamine (abbreviation: TDATA), and 4,4',4"-tris[N-(3-methylphenyl)-N-phenylamino]triphenylamine (abbreviation: MTDATA); compounds having a carbazole skeleton, such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), 3,3'-bis(9-phenyl-9H-carbazole) (abbreviation: PCCP), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), 1,3,5-tris[4-(N-carbazolyl)phenyl]benzene (abbreviation: TCPB), and 9-[4-(10-phenyl-9-anthracenyl)phenyl]-9H-carbazole (abbreviation: CzPA); compounds having a thiophene skeleton, such as 4,4',4"-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV); and compounds having a furan skeleton, such as 4,4',4"-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II).

High molecular compounds such as poly(N-vinylcarbazole) (abbreviation: PVK), poly(4-vinyltriphenylamine) (abbreviation: PVTPA), poly[N-(4-{N-[4-(4-diphenylamino)phenyl]phenyl-N-phenylamino}phenyl)methacrylamide] (abbreviation: PTPDMA), and poly[N,N-bis(4-butylphenyl)-N,N-bis(phenyl)benzidine] (abbreviation: Poly-TPD) can also be used.

Note that the hole-transport material is not limited to the above examples, and one of or a combination of various known materials can be used as the hole-transport material for the hole-injection layer 721 and the hole-transport layer 722. Note that the hole-transport layer 722 may be formed of a plurality of layers. That is, for example, the hole-transport layer 722 may have a stacked-layer structure of a first hole-transport layer and a second hole-transport layer.

<<Light-Emitting Layer 723>>

The light-emitting layer 723 is a layer containing a light-emitting substance. As the light-emitting substance, a substance whose emission color is blue, violet, bluish violet, green, yellowish green, yellow, orange, red, or the like is appropriately used. Here, when the light-emitting element 572 includes a plurality of EL layers as illustrated in FIGS.

39C to 39E, the use of different light-emitting substances for the light-emitting layers 723 in the EL layers enables different emission colors to be exhibited (e.g., it enables white light emission obtained by combining complementary emission colors). For example, when the light-emitting element 572 has the structure illustrated in FIG. 39C, the use of different light-emitting substances for the light-emitting layer 723 in the EL layer 786a and the light-emitting layer 723 in the EL layer 786b can achieve different emission colors of the EL layer 786a and the EL layer 786b. Note that the light-emitting element 572 may have a stacked-layer structure of light-emitting layers containing different light-emitting substances.

The light-emitting layer 723 may contain one or more kinds of organic compounds (a host material and an assist material) in addition to a light-emitting substance (guest material). As the organic compound(s), one or both of the hole-transport material and the electron-transport material can be used.

When the light-emitting element 572 has the structure illustrated in FIG. 39C, it is preferred that a light-emitting substance that emits blue light (a blue-light-emitting substance) be used as a guest material in one of the EL layers 786a and 786b and a substance that emits green light (a green-light-emitting substance) and a substance that emits red light (a red-light-emitting substance) be used in the other EL layer. This structure is effective when the blue-light-emitting substance (blue-light-emitting layer) has lower light emission efficiency or a shorter lifetime than the others. Here, it is preferred that a light-emitting substance that converts singlet excitation energy into light in the visible light range be used as the blue-light-emitting substance and light-emitting substances that convert triplet excitation energy into light in the visible light range be used as the green- and red-light-emitting substances, whereby the spectrum balance between R, G, and B is improved.

There is no particular limitation on the light-emitting substance that can be used for the light-emitting layer 723, and it is possible to use a light-emitting substance that converts singlet excitation energy into light in the visible light range or a light-emitting substance that converts triplet excitation energy into light in the visible light range. Examples of the light-emitting substance are given below.

Examples of the light-emitting substance that converts singlet excitation energy into light include substances that exhibit fluorescence (fluorescent materials). Specific examples include a pyrene derivative, an anthracene derivative, a triphenylene derivative, a fluorene derivative, a carbazole derivative, a dibenzothiophene derivative, a dibenzofuran derivative, a dibenzoquinoxaline derivative, a quinoxaline derivative, a pyridine derivative, a pyrimidine derivative, a phenanthrene derivative, and a naphthalene derivative. A pyrene derivative is particularly preferable because it has a high emission quantum yield. Specific examples of the pyrene derivative include N,N-bis(3-methylphenyl)-N,N-bis[3-(9-phenyl-9H-fluoren-9-yl)phenyl]pyrene-1,6-diamine (abbreviation: 1,6mMemFLPAPrn), N,N-diphenyl-N,N-bis[4-(9-phenyl-9H-fluoren-9-yl)phenyl]pyrene-1,6-diamine (abbreviation: 1,6FLPAPrn), N,N-bis(dibenzofuran-2-yl)-N,N-diphenylpyrene-1,6-diamine (abbreviation: 1,6FrAPrn), NN-bis(dibenzothiophen-2-yl)-N,N-diphenylpyrene-1,6-diamine (abbreviation: 1,6ThAPrn), N,N-(pyrene-1,6-diyl)bis[(N-phenylbenzo[b]naphtho[1,2-d]furan)-6-amine] (abbreviation: 1,6BnfAPrn), N,N-(pyrene-1,6-diyl)bis[(N-phenylbenzo[b]naphtho[1,2-d]furan)-8-amine] (abbreviation: 1,6BnfAPrn-02), and N,N-(pyrene-1,6-diyl)bis[(6,N-diphenylbenzo[b]naphtho[1,2-d]furan)-8-amine] (abbreviation: 1,6BnfAPrn-03). In addition, pyrene derivatives are compounds effective for meeting the chromaticity of blue in one embodiment of the present invention.

In addition, it is possible to use 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N-bis[4-(9H-carbazol-9-yl)phenyl]-N,N-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), 4-(10-phenyl-9-anthryl)-4'-(9-phenyl-9H-carbazol-3-yl)triphenylamine (abbreviation: PCBAPA), 4-[4-(10-phenyl-9-anthryl)phenyl]-4'-(9-phenyl-9H-carbazol-3-yl)triphenylamine (abbreviation: PCBAPBA), perylene, 2,5,8,11-tetra(tert-butyl)perylene (abbreviation: TBP), N,N'-(2-tert-butylanthracene-9,10-diyldi-4,1-phenylene)bis[N,N',N'-triphenyl-1,4-phenylenediamine](abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), or the like.

Examples of the light-emitting substance that converts triplet excitation energy into light include a substance that exhibits phosphorescence (phosphorescent material) and a thermally activated delayed fluorescence (TADF) material that exhibits thermally activated delayed fluorescence.

Examples of a phosphorescent material include an organometallic complex, a metal complex (platinum complex), and a rare earth metal complex. These substances exhibit the respective emission colors (emission peaks) and thus, any of them is selected appropriately according to need.

As examples of a phosphorescent material which emits blue or green light and whose emission spectrum has a peak wavelength at greater than or equal to 450 nm and less than or equal to 570 nm, the following substances can be given.

Examples include organometallic complexes having a 4H-triazole skeleton, such as tris{2-[5-(2-methylphenyl)-4-(2,6-dimethylphenyl)-4H-1,2,4-triazol-3-yl-κ$N^2$]phenyl-κC}iridium(III) (abbreviation: [Ir(mpptz-dmp)$_3$]), tris(5-methyl-3,4-diphenyl-4H-1,2,4-triazolato)iridium(III) (abbreviation: [Ir(Mptz)$_3$]), tris[4-(3-biphenyl)-5-isopropyl-3-phenyl-4H-1,2,4-triazolato]iridium(III) (abbreviation: [Ir(iPrptz-3b)$_3$]), and tris[3-(5-biphenyl)-5-isopropyl-4-phenyl-4H-1,2,4-triazolato]iridium(III) (abbreviation: [Ir(iPr5btz)$_3$]); organometallic complexes having a 1H-triazole skeleton, such as tris[3-methyl-1-(2-methylphenyl)-5-phenyl-1H-1,2,4-triazolato]iridium(III) (abbreviation: [Ir(Mptz1-mp)$_3$]) and tris(1-methyl-5-phenyl-3-propyl-1H-1,2,4-triazolato)iridium(III) (abbreviation: [Ir(Prptz1-Me)$_3$]); organometallic complexes having an imidazole skeleton, such as fac-tris[1-(2,6-diisopropylphenyl)-2-phenyl-1H-imidazole]iridium(III) (abbreviation: [Ir(iPrpmi)$_3$]) and tris[3-(2,6-dimethylphenyl)-7-methylimidazo[1,2-J]phenanthridinato]iridium(III) (abbreviation: [Ir(dmpimpt-Me)$_3$]); and organometallic complexes in which a phenylpyridine derivative having an electron-withdrawing group is a ligand, such as bis[2-(4',6'-difluorophenyl)pyridinato-N,$C^{2'}$]iridium(III) tetrakis(1-pyrazolyl)borate (abbreviation: FIr6), bis[2-(4',6'-difluorophenyl)pyridinato-N,$C^{2'}$] iridium(III) picolinate (abbreviation: FIrpic), bis[2-(3,5-bistrifluoromethyl-phenyl)-pyridinato-N,$C^{2'}$]iridium(III) picolinate (abbreviation: [Ir(CF$_3$ppy)$_2$(pic)]), and bis[2-(4', 6'-difluorophenyl)pyridinato-N,C$^{2'}$]iridium(III) acetylacetonate (abbreviation: FIr(acac)).

As examples of a phosphorescent material which emits green or yellow light and whose emission spectrum has a peak wavelength at greater than or equal to 495 nm and less than or equal to 590 nm, the following substances can be given.

Examples include organometallic iridium complexes having a pyrimidine skeleton, such as tris(4-methyl-6-phenylpyrimidinato)iridium(III) (abbreviation: [Ir(mppm)$_3$]), tris(4-t-butyl-6-phenylpyrimidinato)iridium(III) (abbreviation: [Ir(tBuppm)$_3$]), (acetylacetonato)bis(6-methyl-4-phenylpyrimidinato)iridium(III) (abbreviation: [Ir(mppm)$_2$(acac)]), (acetylacetonato)bis(6-tert-butyl-4-phenylpyrimidinato)iridium(III) (abbreviation: [Ir(tBuppm)$_2$(acac)]), (acetylacetonato)bis[6-(2-norbornyl)-4-phenylpyrimidinato]iridium(III) (abbreviation: [Ir(nbppm)$_2$(acac)]), (acetylacetonato)bis[5-methyl-6-(2-methylphenyl)-4-phenylpyrimidinato]iridium(III) (abbreviation: [Ir(mpmppm)$_2$(acac)]), (acetylacetonato)bis{4,6-dimethyl-2-[6-(2,6-dimethylphenyl)-4-pyrimidinyl-κN$^3$]phenyl-κC}iridium(III) (abbreviation: [Ir(dmppm-dmp)$_2$(acac)]), and (acetylacetonato)bis(4,6-diphenylpyrimidinato)iridium(III) (abbreviation: [Ir(dppm)$_2$(acac)]); organometallic iridium complexes having a pyrazine skeleton, such as (acetylacetonato)bis(3,5-dimethyl-2-phenylpyrazinato)iridium(III) (abbreviation: [Ir(mppr-Me)$_2$(acac)]) and (acetylacetonato)bis(5-isopropyl-3-methyl-2-phenylpyrazinato)iridium(III) (abbreviation: [Ir(mppr-iPr)$_2$(acac)]); organometallic iridium complexes having a pyridine skeleton, such as tris(2-phenylpyridinato-N,C$^{2'}$)iridium(III) (abbreviation: [Ir(ppy)$_3$]), bis(2-phenylpyridinato-N,C$^{2'}$)iridium(III) acetylacetonate (abbreviation: [Ir(ppy)$_2$(acac)]), bis(benzo[h]quinolinato)iridium(III) acetylacetonate (abbreviation: [Ir(bzq)$_2$(acac)]), tris(benzo[h]quinolinato)iridium(III) (abbreviation: [Ir(bzq)$_3$]), tris(2-phenylquinolinato-N,C$^{2'}$)iridium(III) (abbreviation: [Ir(pq)$_3$]), and bis(2-phenylquinolinato-N,C$^{2'}$)iridium(III) acetylacetonate (abbreviation: [Ir(pq)$_2$(acac)]); organometallic complexes such as bis(2,4-diphenyl-1,3-oxazolato-N,C$^{2'}$)iridium(III) acetylacetonate (abbreviation: [Ir(dpo)$_2$(acac)]), bis{2-[4'-(perfluorophenyl)phenyl]pyridinato-N,C$^{2'}$}iridium(III) acetylacetonate (abbreviation: [Ir(p-PF-ph)$_2$(acac)]), and bis(2-phenylbenzothiazolato-N,C$^{2'}$)iridium(III) acetylacetonate (abbreviation: [Ir(bt)$_2$(acac)]); and rare earth metal complexes such as tris(acetylacetonato)(monophenanthroline)terbium(III) (abbreviation: [Tb(acac)$_3$(Phen)]).

Among the above, organometallic iridium complexes having a pyridine skeleton (particularly, a phenylpyridine skeleton) or a pyrimidine skeleton are compounds effective for meeting the chromaticity of green in one embodiment of the present invention.

As examples of a phosphorescent material which emits yellow or red light and whose emission spectrum has a peak wavelength at greater than or equal to 570 nm and less than or equal to 750 nm, the following substances can be given.

Examples include organometallic complexes having a pyrimidine skeleton, such as (diisobutyrylmethanato)bis[4,6-bis(3-methylphenyl)pyrimidinato]iridium(III) (abbreviation: [Ir(5mdppm)$_2$(dibm)]), bis[4,6-bis(3-methylphenyl)pyrimidinato](dipivaloylmethanato)iridium(III) (abbreviation: [Ir(5mdppm)$_2$(dpm)]), and (dipivaloylmethanato)bis[4,6-di(naphthalen-1-yl)pyrimidinato]iridium(III) (abbreviation: [Ir(dlnpm)$_2$(dpm)]); organometallic complexes having a pyrazine skeleton, such as (acetylacetonato)bis(2,3,5-triphenylpyrazinato)iridium(III) (abbreviation: [Ir(tppr)$_2$(acac)]), bis(2,3,5-triphenylpyrazinato)(dipivaloylmethanato)iridium(III) (abbreviation: [Ir(tppr)$_2$(dpm)]), bis{4,6-dimethyl-2-[3-(3,5-dimethylphenyl)-5-phenyl-2-pyrazinyl-κN]phenyl-κC}(2,6-dimethyl-3,5-heptanedionato-κ$^2$O,O')iridium(III) (abbreviation: [Ir(dmdppr-P)$_2$(dibm)]), bis{4,6-dimethyl-2-[5-(4-cyano-2,6-dimethylphenyl)-3-(3,5-dimethylphenyl)-2-pyrazinyl-κN]phenyl-κC}(2,2,6,6-tetramethyl-3,5-heptanedionato-κ2O,O')iridium(III) (abbreviation: [Ir(dmdppr-dmCP)$_2$(dpm)]), (acetylacetonato)bis[2-methyl-3-phenylquinoxalinato-N,C$^{2'}$]iridium(III) (abbreviation: [Ir(mpq)$_2$(acac)]), (acetylacetonato)bis(2,3-diphenylquinoxalinato-N,C$^{2'}$)iridium(III) (abbreviation: [Ir(dpq)$_2$(acac)]), and (acetylacetonato)bis[2,3-bis(4-fluorophenyl)quinoxalinato]iridium(III) (abbreviation: [Ir(Fdpq)$_2$(acac)]); organometallic complexes having a pyridine skeleton, such as tris(1-phenylisoquinolinato-N,C$^{2'}$)iridium(III) (abbreviation: [Ir(piq)$_3$]) and bis(1-phenylisoquinolinato-N,C$^2$)iridium(III) acetylacetonate (abbreviation: [Ir(piq)$_2$(acac)]); platinum complexes such as 2,3,7,8,12,13,17,18-octaethyl-21H,23H-porphyrinplatinum(II) (abbreviation: [PtOEP]); and rare earth metal complexes such as tris(1,3-diphenyl-1,3-propanedionato)(monophenanthroline)europium(III) (abbreviation: [Eu(DBM)$_3$(Phen)]) and tris[1-(2-thenoyl)-3,3,3-trifluoroacetonato](monophenanthroline)europium(III) (abbreviation: [Eu(TTA)$_3$(Phen)]).

Among the above, organometallic iridium complexes having a pyrazine skeleton are compounds effective for meeting the chromaticity of red in one embodiment of the present invention. In particular, organometallic iridium complexes having a cyano group (e.g., [Ir(dmdppr-dmCP)$_2$(dpm)]) are preferable because of their high stability.

Note that as the blue-light-emitting substance, a substance whose photoluminescence peak wavelength is greater than or equal to 430 nm and less than or equal to 470 nm, preferably greater than or equal to 430 nm and less than or equal to 460 nm is used. As the green-light-emitting substance, a substance whose photoluminescence peak wavelength is greater than or equal to 500 nm and less than or equal to 540 nm, preferably greater than or equal to 500 nm and less than or equal to 530 nm is used. As the red-light-emitting substance, a substance whose photoluminescence peak wavelength is greater than or equal to 610 nm and less than or equal to 680 nm, preferably greater than or equal to 620 nm and less than or equal to 680 nm is used. Note that the photoluminescence may be measured with either a solution or a thin film.

With the parallel use of such compounds and the microcavity effect, the above chromaticity can be met more easily. Here, a transflective electrode (a metal thin film portion) that is needed for obtaining the microcavity effect has a thickness of preferably greater than or equal to 20 nm and less than or equal to 40 nm, further preferably greater than 25 nm and less than or equal to 40 nm. Note that the thickness greater than 40 nm possibly reduces the efficiency.

As the organic compounds (the host material and the assist material) used in the light-emitting layer 723, one or more kinds of substances having a larger energy gap than the light-emitting substance (the guest material) are used. Note that the hole-transport materials listed above and the electron-transport materials given below can be used as the host material and the assist material, respectively.

When the light-emitting substance is a fluorescent material, it is preferable to use, as the host material, an organic compound that has a high energy level in a singlet excited state and has a low energy level in a triplet excited state. For example, an anthracene derivative or a tetracene derivative is preferably used. Specific examples include 9-phenyl-3-

[4-(10-phenyl-9-anthryl)phenyl]-9H-carbazole (abbreviation: PCzPA), 3-[4-(1-naphthyl)-phenyl]-9-phenyl-9H-carbazole (abbreviation: PCPN), 9-[4-(10-phenyl-9-anthracenyl)phenyl]-9H-carbazole (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d]furan (abbreviation: 2mBnfPPA), 9-phenyl-10-{4-(9-phenyl-9H-fluoren-9-yl)biphenyl-4'-yl}anthracene (abbreviation: FLPPA), 5,12-diphenyltetracene, and 5,12-bis(biphenyl-2-yl)tetracene.

When the light-emitting substance is a phosphorescent material, an organic compound having triplet excitation energy (energy difference between a ground state and a triplet excited state) higher than that of the light-emitting substance can be selected as the host material. In that case, it is possible to use a zinc- or aluminum-based metal complex, an oxadiazole derivative, a triazole derivative, a benzimidazole derivative, a quinoxaline derivative, a dibenzoquinoxaline derivative, a dibenzothiophene derivative, a dibenzofuran derivative, a pyrimidine derivative, a triazine derivative, a pyridine derivative, a bipyridine derivative, a phenanthroline derivative, an aromatic amine, a carbazole derivative, or the like.

Specific examples include metal complexes such as tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ); heterocyclic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2''-(1,3,5-benzenetriyl)-tris(1-phenyl-1H-benzimidazole) (abbreviation: TPBI), bathophenanthroline (abbreviation: BPhen), bathocuproine (abbreviation: BCP), 2,9-bis(naphthalen-2-yl)-4,7-diphenyl-1,10-phenanthroline (abbreviation: NBphen), and 9-[4-(5-phenyl-1,3,4-oxadiazol-2-yl)phenyl]-9H-carbazole (abbreviation: CO11); and aromatic amine compounds such as NPB, TPD, and BSPB.

In addition, condensed polycyclic aromatic compounds such as anthracene derivatives, phenanthrene derivatives, pyrene derivatives, chrysene derivatives, and dibenzo[g,p]chrysene derivatives can be used. Specifically, it is possible to use, for example, 9,10-diphenylanthracene (abbreviation: DPAnth), N,N-diphenyl-9-[4-(10-phenyl-9-anthryl)phenyl]-9H-carbazol-3-amine (abbreviation: CzAIPA), 4-(10-phenyl-9-anthryl)triphenylamine (abbreviation: DPhPA), YGAPA, PCAPA, N,9-diphenyl-N-{4-[4-(10-phenyl-9-anthryl)phenyl]phenyl}-9H-carbazol-3-amine (abbreviation: PCAPBA), 9,10-diphenyl-2-[N-phenyl-N-(9-phenyl-9H-carbazol-3-yl)amino]anthracene (abbreviation: 2PCAPA), 6,12-dimethoxy-5,11-diphenylchrysene, N,N,N',N',N'',N'',N''',N'''-octaphenyldibenzo[g,p]chrysene-2,7,10,15-tetraamine (abbreviation: DBC1), 9-[4-(10-phenyl-9-anthracenyl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), or 1,3,5-tri(1-pyrenyl)benzene (abbreviation: TPB3).

When a plurality of organic compounds are used for the light-emitting layer 723, compounds that form an exciplex are preferably mixed with a light-emitting substance. In that case, any of various organic compounds can be used in an appropriate combination; to form an exciplex efficiently, it is particularly preferable to combine a compound that easily accepts holes (hole-transport material) and a compound that easily accepts electrons (electron-transport material). As the hole-transport material and the electron-transport material, specifically, any of the materials described in this embodiment can be used.

The TADF material enables up-conversion of a triplet excited state into a singlet excited state (i.e., reverse intersystem crossing) using a little thermal energy and efficiently emits light from the singlet excited state (efficiently exhibits fluorescence). Thermally activated delayed fluorescence is efficiently obtained under the condition where the energy difference between the triplet excitation level and the singlet excitation level is greater than or equal to 0 eV and less than or equal to 0.2 eV, preferably greater than or equal to 0 eV and less than or equal to 0.1 eV. Note that "delayed fluorescence" exhibited by the TADF material refers to light emission having the same spectrum as normal fluorescence and an extremely long lifetime. The lifetime is $1 \times 10^{-6}$ seconds or longer, preferably $1 \times 10^{-3}$ seconds or longer.

Examples of the TADF material include fullerene, a derivative thereof, an acridine derivative such as proflavine, and eosin. Other examples include a metal-containing porphyrin such as a porphyrin containing magnesium (Mg), zinc (Zn), cadmium (Cd), tin (Sn), platinum (Pt), indium (In), or palladium (Pd). Examples of the metal-containing porphyrin include a protoporphyrin-tin fluoride complex ($SnF_2$(Proto IX)), a mesoporphyrin-tin fluoride complex ($SnF_2$(Meso IX)), a hematoporphyrin-tin fluoride complex ($SnF_2$(Hemato IX)), a coproporphyrin tetramethyl ester-tin fluoride complex ($SnF_2$(Copro III-4Me)), an octaethylporphyrin-tin fluoride complex ($SnF_2$(OEP)), an etioporphyrin-tin fluoride complex ($SnF_2$(Etio I)), and an octaethylporphyrin-platinum chloride complex ($PtCl_2OEP$).

Alternatively, it is possible to use a heterocyclic compound having a it-electron rich heteroaromatic ring and a it-electron deficient heteroaromatic ring, such as 2-(biphenyl-4-yl)-4,6-bis(12-phenylindolo[2,3-a]carbazol-11-yl)-1,3,5-triazine (PIC-TRZ), 2-{4-[3-(N-phenyl-9H-carbazol-3-yl)-9H-carbazol-9-yl]phenyl}-4,6-diphenyl-1,3,5-triazine (PCCzPTzn), 2-[4-(10H-phenoxazin-10-yl)phenyl]-4,6-diphenyl-1,3,5-triazine (PXZ-TRZ), 3-[4-(5-phenyl-5,10-dihydrophenazin-10-yl)phenyl]-4,5-diphenyl-1,2,4-triazole (PPZ-3TPT), 3-(9,9-dimethyl-9H-acridin-10-yl)-9H-xanthen-9-one (ACRXTN), bis[4-(9,9-dimethyl-9,10-dihydroacridine)phenyl]sulfone (DMAC-DPS), or 10-phenyl-10H,10'H-spiro[acridin-9,9'-anthracen]-10'-one (ACRSA). Note that a substance in which a it-electron rich heteroaromatic ring is directly bonded to a it-electron deficient heteroaromatic ring is particularly preferable because both the donor property of the it-electron rich heteroaromatic ring and the acceptor property of the it-electron deficient heteroaromatic ring are improved and the energy difference between the singlet excited state and the triplet excited state becomes small.

Note that a TADF material can also be used in combination with another organic compound.

<<Electron-Transport Layer 724>>

The electron-transport layer 724 transports the electrons, which are injected from the conductor 788 by the electron-injection layer 725, to the light-emitting layer 723. Note that the electron-transport layer 724 contains an electron-transport material. The electron-transport material used for the electron-transport layer 724 is preferably a substance with an electron mobility of higher than or equal to $1\times10^{-6}$ cm$^2$/Vs. Note that any other substance can also be used as long as the substance transports electrons more easily than it transports holes.

Examples of the electron-transport material include metal complexes having a quinoline ligand, a benzoquinoline ligand, an oxazole ligand, and a thiazole ligand; an oxadiazole derivative; a triazole derivative; a phenanthroline derivative; a pyridine derivative; and a bipyridine derivative. In addition, a it-electron deficient heteroaromatic compound such as a nitrogen-containing heteroaromatic compound can also be used.

Specifically, it is possible to use any of metal complexes such as Alq$_3$, tris(4-methyl-8-quinolinolato)aluminum(III) (abbreviation: Almq$_3$), bis(10-hydroxybenzo[h]quinolinato)beryllium (abbreviation: BeBq$_2$), BAlq, Zn(BOX)$_2$, and bis[2-(2-hydroxyphenyl)benzothiazolato]zinc(II) (abbreviation: Zn(BTZ)$_2$); heteroaromatic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4'-tert-butylphenyl)-4-phenyl-5-(4"-biphenyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: Bphen), bathocuproine (abbreviation: BCP), and 4,4'-bis(5-methylbenzoxazol-2-yl)stilbene (abbreviation: BzOs); and quinoxaline derivatives and dibenzoquinoxaline derivatives such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), and 6-[3-(dibenzothiophen-4-yl)phenyl]dibenzo[f,h]quinoxaline (abbreviation: 6mDBTPDBq-II).

Alternatively, a high-molecular compound such as poly(2,5-pyridinediyl) (abbreviation: PPy), poly[(9,9-dihexylfluorene-2,7-diyl)-co-(pyridine-3,5-diyl)] (abbreviation: PF-Py), or poly[(9,9-dioctylfluorene-2,7-diyl)-co-(2,2'-bipyridine-6,6'-diyl)] (abbreviation: PF-BPy) can be used.

The electron-transport layer 724 is not limited to a single layer and may be a stack of two or more layers each containing any of the above substances.

<<Electron-Injection Layer 725>>

The electron-injection layer 725 contains a substance having a high electron-injection property. The electron-injection layer 725 can be formed using an alkali metal, an alkaline earth metal, or a compound thereof, such as lithium fluoride (LiF), cesium fluoride (CsF), calcium fluoride (CaF$_2$), or lithium oxide (LiOx). A rare earth metal compound like erbium fluoride (ErF$_3$) can also be used. An electrode may also be used for the electron-injection layer 725. An example of the electrode includes a substance in which electrons are added at high concentration to calcium oxide-aluminum oxide. Any of the above-described substances used for the electron-transport layer 724 can also be used.

A composite material in which an organic compound and an electron donor (donor) are mixed may also be used for the electron-injection layer 725. Such a composite material is excellent in an electron-injection property and an electron-transport property because electrons are generated in the organic compound by the electron donor. The organic compound here is preferably a material excellent in transporting the generated electrons; specifically, for example, the electron-transport material used for the electron-transport layer 724 (e.g., a metal complex or a heteroaromatic compound) can be used. As the electron donor, a substance showing an electron-donating property with respect to the organic compound is used. Specifically, an alkali metal, an alkaline earth metal, and a rare earth metal are preferable, and lithium, cesium, magnesium, calcium, erbium, ytterbium, and the like are given. In addition, an alkali metal oxide and an alkaline earth metal oxide are preferable, and lithium oxide, calcium oxide, barium oxide, and the like are given. Alternatively, a Lewis base such as magnesium oxide can be used. Further alternatively, an organic compound such as tetrathiafulvalene (abbreviation: TTF) can be used.

<<Charge Generation Layer 792>>

The charge generation layer 792 has a function of injecting electrons into the EL layer 786 that is closer to the conductor 772 of the two EL layers 786 in contact with the charge generation layer 792 and injecting holes to the other EL layer 786 that is closer to the conductor 788, when a voltage is applied between the conductor 772 and the conductor 788. For example, in the light-emitting element 572 having the structure illustrated in FIG. 39C, the charge generation layer 792 has a function of injecting electrons into the EL layer 786a and injecting holes into the EL layer 786b. Note that the charge generation layer 792 may have either a structure in which an electron acceptor (acceptor) is added to a hole-transport material or a structure in which an electron donor (donor) is added to an electron-transport material. Alternatively, both of these structures may be stacked. Forming the charge generation layer 792 by using any of the above materials can inhibit the increase in driving voltage of the display device 810 including the stack of the EL layers.

When the charge generation layer 792 has a structure in which an electron acceptor is added to a hole-transport material, the electron acceptor can be 7,7,8,8-tetracyano-2,3,5,6-tetrafluoroquinodimethane (abbreviation: F$_4$-TCNQ), chloranil, or the like. Other examples include oxides of metals that belong to Group 4 to Group 8 of the periodic table. Specific examples are vanadium oxide, niobium oxide, tantalum oxide, chromium oxide, molybdenum oxide, tungsten oxide, manganese oxide, and rhenium oxide.

When the charge generation layer 792 has a structure in which an electron donor is added to an electron-transport material, an alkali metal, an alkaline earth metal, a rare earth metal, or a metal that belongs to Group 2 or Group 13 of the periodic table, or an oxide or carbonate thereof can be used as the electron donor. Specifically, lithium (Li), cesium (Cs), magnesium (Mg), calcium (Ca), ytterbium (Yb), indium (In), lithium oxide, cesium carbonate, or the like is preferably used. An organic compound such as tetrathianaphthacene may be used as the electron donor.

For fabrication of the light-emitting element 572, a vacuum process such as an evaporation method or a solution process such as a spin coating method or an ink-jet method can be used. In the case of employing an evaporation method, it is possible to use a physical vapor deposition method (PVD method) such as a sputtering method, an ion plating method, an ion beam evaporation method, a molecular beam evaporation method, or a vacuum evaporation method, a chemical vapor deposition method (CVD method), or the like. Specifically, the functional layers (the hole-injection layer, the hole-transport layer, the light-emitting layer, the electron-transport layer, and the electron-injection layer) included in the EL layer and the charge generation layer of the light-emitting element can be formed by an evaporation method (e.g., a vacuum evaporation method), a coating method (e.g., a dip coating method, a die coating method, a bar coating method, a spin coating method, or a spray coating method), a printing method (e.g., an ink-jet method, screen printing (stencil), offset printing (planography), flexography (relief printing), gravure printing, or micro-contact printing), or the like.

Note that materials that can be used for the functional layers (the hole-injection layer, the hole-transport layer, the light-emitting layer, the electron-transport layer, and the electron-injection layer) included in the EL layer and the charge generation layer of the light-emitting element described in this embodiment are not limited to the above materials, and other materials can be used in combination as long as the functions of the layers are fulfilled. For example, a high molecular compound (e.g., an oligomer, a dendrimer, and a polymer), a middle molecular compound (a compound between a low molecular compound and a high molecular compound, with a molecular weight of 400 to 4000), or an inorganic compound (e.g., a quantum dot material) can be used. The quantum dot material may be a colloidal quantum dot material, an alloyed quantum dot material, a core-shell quantum dot material, a core quantum dot material, or the like.

The display device 810 described in this embodiment can be used for the light source described in Embodiment 1. With the use of the display device 810 for the light source described in Embodiment 1, light-emitting elements can be arranged at high density in the light source. Thus, the electronic device of one embodiment of the present invention can accurately recognize a facial feature of the user of the electronic device, such as the user's facial expression.

Figure 40A:
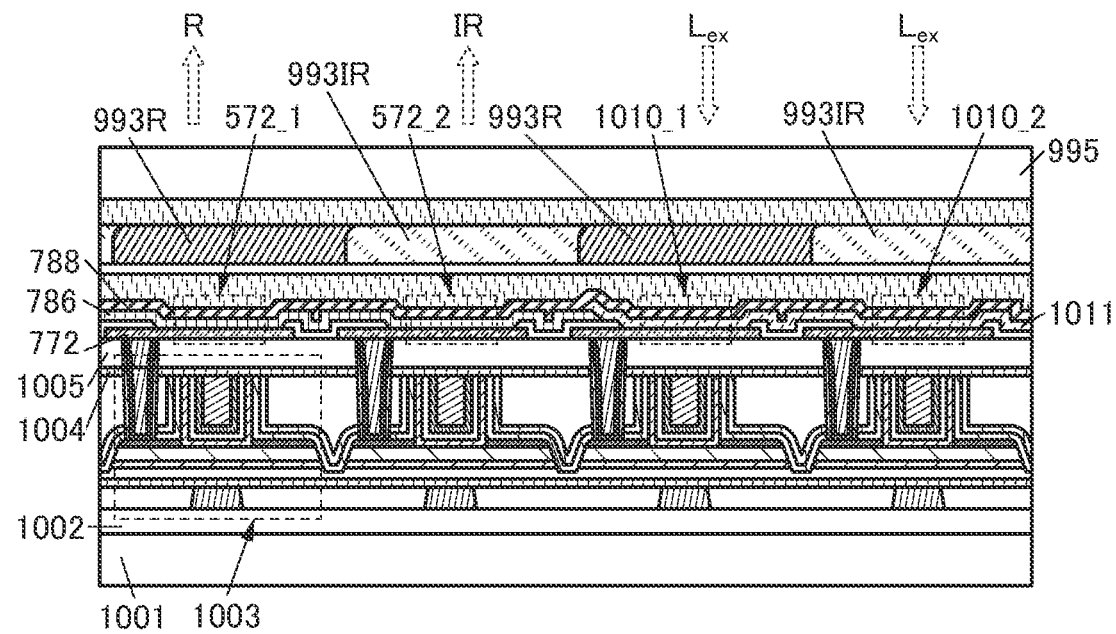
FIGS. 40A and 40B are cross-sectional views each illustrating a structure example of an imaging device.

FIG. 40A is a cross-sectional view illustrating a structure example of an imaging device of one embodiment of the present invention. As illustrated in FIG. 40A, a transistor 1003, the light-emitting element 572, a photoelectric conversion element 1010, the coloring layer 993, and the like can be provided between a substrate 1001 and the substrate 995. Here, the transistor 1003 can be an OS transistor, for example. FIG. 40A illustrates four transistors 1003.

An insulator 1002 is provided over the substrate 1001, and the transistor 1003 is provided over the insulator 1002. An insulator 1004 is provided over the transistor 1003, and an insulator 1005 is provided over the insulator 1004. The light-emitting element 572 and the photoelectric conversion element 1010 are provided over the insulator 1005. The coloring layer 993 is provided to have a region overlapping with the light-emitting element 572 or the photoelectric conversion element 1010. FIG. 40A shows that two light-emitting elements 572 (a light-emitting element 572_1 and a light-emitting element 572_2) and two photoelectric conversion elements 1010 (a photoelectric conversion element 1010_1 and a photoelectric conversion element 10102) are electrically connected to the corresponding transistors 1003. In FIG. 40A, a coloring layer 993R that is the coloring layer 993 having a function of transmitting red light is provided to have a region overlapping with the light-emitting element 572_1, and a coloring layer 993IR that is the coloring layer 993 having a function of transmitting infrared light is provided to have a region overlapping with the light-emitting element 572_2. In addition, the coloring layer 993R is provided to have a region overlapping with the photoelectric conversion element 10101, and the coloring layer 9931R is provided to have a region overlapping with the photoelectric conversion element 1010_2.

The photoelectric conversion element 1010 has a function of receiving light $L_{ex}$ that is applied from the outside of the imaging device and converting it into an electric signal corresponding to the illuminance of the received light $L_{ex}$.

The light-emitting element 572 preferably has a function of emitting white light and infrared light. Accordingly, light emitted from the light-emitting element 572_1 is emitted to the outside of the imaging device through the coloring layer 993R as red light R. Light emitted from the light-emitting element 572_2 is emitted to the outside of the imaging device through the coloring layer 993IR as infrared light IR. The red light R and the infrared light IR, which are emitted to the outside of the imaging device, strike an object and are reflected and applied to the photoelectric conversion elements 1010. For example, when the imaging device having the structure illustrated in FIG. 40A is used for the glasses-type electronic device described in Embodiment 1, the red light R and the infrared light IR are applied to the face of the user of the glasses-type electronic device, and the reflected light $L_{ex}$ can be detected by the photoelectric conversion elements 1010.

By having the function of detecting both red light and infrared light, the imaging device can detect, for example, the state of the eyes and surrounding areas of the user of the electronic device of one embodiment of the present invention more accurately than an imaging device having a function of detecting only one of red light and infrared light. Consequently, a facial feature of the user of the electronic device of one embodiment of the present invention, such as the user's facial expression, can be recognized accurately, for example; thus, the electronic device of one embodiment of the present invention can have a function of estimating the degree of fatigue or emotions of the user, for instance.

Note that when the display device of one embodiment of the present invention includes a photoelectric conversion element, the display device can have the structure illustrated in FIG. 40A. In this case, the display device includes the light-emitting element 572 including a region overlapping with the coloring layer 993 having a function of transmitting red light, the light-emitting element 572 including a region overlapping with the coloring layer 993 having a function of transmitting infrared light, the light-emitting element 572 including a region overlapping with the coloring layer 993 having a function of transmitting green light, and the light-emitting element 572 including a region overlapping with the coloring layer 993 having a function of transmitting blue light.

The light-emitting element 572 is composed of the conductor 772, the EL layer 786, and the conductor 788. The photoelectric conversion element 1010 is composed of the conductor 772, an active layer 1011, and the conductor 788. The transistor 1003 is electrically connected to the conductor 772.

The active layer 1011 can have a stacked-layer structure in which a p-type semiconductor and an n-type semiconductor are stacked to form a PN junction; or a stacked-layer structure in which a p-type semiconductor, an i-type semiconductor, and an n-type semiconductor are stacked to form a PIN junction, for example.

As the semiconductor used for the active layer 1011, an inorganic semiconductor such as silicon or an organic semiconductor containing an organic compound can be used. In particular, the use of an organic semiconductor material is preferable, in which case the EL layer 786 of the light-emitting element 572 and the active layer 1011 are easily formed by the same vacuum evaporation method, and thus the same manufacturing apparatus can be used.

When an organic semiconductor material is used for the active layer 1011, an electron-accepting organic semiconductor material such as fullerene (e.g., $C_{60}$ or $C_{70}$) or its derivative can be used as an n-type semiconductor material. As a p-type semiconductor material, an electron-donating organic semiconductor material such as copper(II) phthalocyanine (CuPc) or tetraphenyldibenzoperiflanthene (DBP) can be used. The active layer 1011 may have a stacked-layer structure (a P—N structure) including an electron-accepting semiconductor material and an electron-donating semiconductor material, or a stacked-layer structure (a P—I—N structure) in which a bulk heterostructure layer formed by co-evaporation of an electron-accepting semiconductor material and an electron-donating semiconductor material is provided between the materials of the P—N structure. Furthermore, a layer functioning as a hole blocking layer or a layer functioning as an electron blocking layer may be provided around (above or below) the P—N structure or the P—I—N structure, in order to inhibit dark current caused when light is not applied.

In the light-emitting element 572, the EL layer 786 is provided over the conductor 772. In the photoelectric conversion element 1010, the active layer 1011 is provided over the conductor 772. The conductor 788 is provided to cover the EL layer 786 and the active layer 1011. Accordingly, the conductor 788 can serve as both the electrode of the light-emitting element 572 and the electrode of the photoelectric conversion element 1010.

Figure 40B:
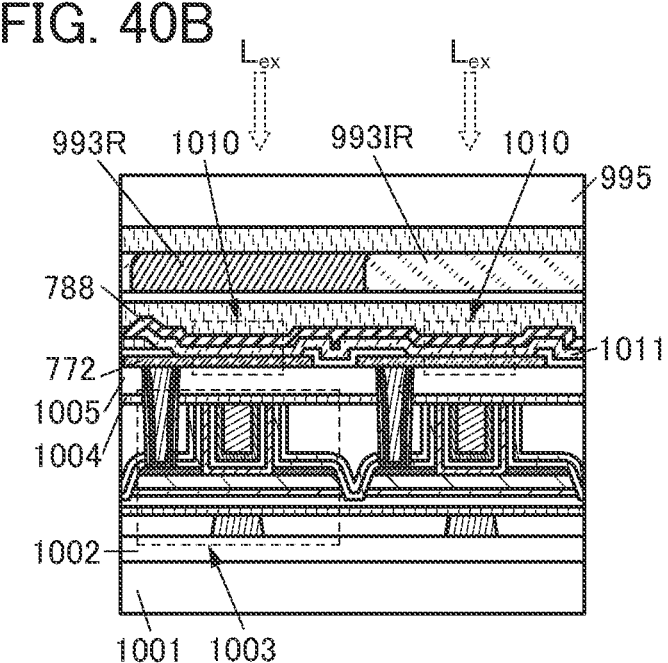

FIG. 40B is a cross-sectional view illustrating a structure example of the imaging device of one embodiment of the present invention, and illustrates a variation example of the structure in FIG. 40A. The imaging device having the structure in FIG. 40B is different from that having the structure in FIG. 40A in that the light-emitting element 572 is not provided.

When the electronic device of one embodiment of the present invention includes the imaging device having the structure in FIG. 40B, providing a light source outside the imaging device allows the imaging device to detect light emitted from the light source. For example, when the imaging device having the structure in FIG. 40B is used for the glasses-type electronic device described in Embodiment 1, red light and infrared light that are emitted from the light source are applied to the face of the user of the glasses-type electronic device, and the reflected light $L_{ex}$ can be detected by the photoelectric conversion elements 1010.

When the imaging device included in the electronic device of one embodiment of the present invention has the structure illustrated in FIG. 40B, the photoelectric conversion elements 1010 can be provided at high density in the imaging device.

At least part of any of the structure examples, the drawings corresponding thereto, and the like described in this embodiment can be implemented in combination with any of the other structure examples, the other drawings, and the like as appropriate.

At least part of this embodiment can be implemented in combination with any of the other embodiments described in this specification as appropriate.

Embodiment 3

In this embodiment, transistors that can be used in the display device of one embodiment of the present invention will be described.

<Structure Example 1 of Transistor>

Figure 41A:
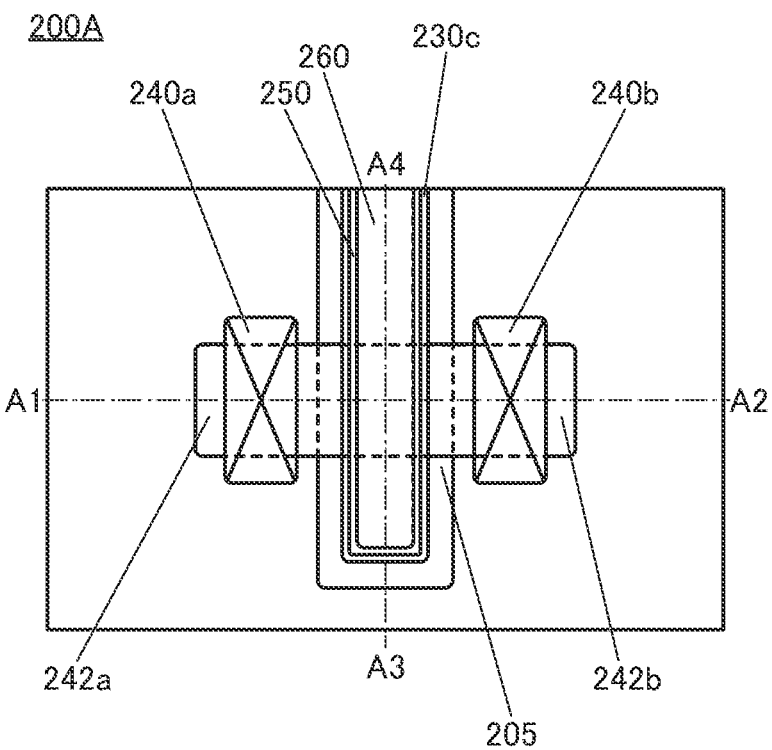
FIG. 41A is a top view illustrating a structure example of a transistor.
Figure 41C:
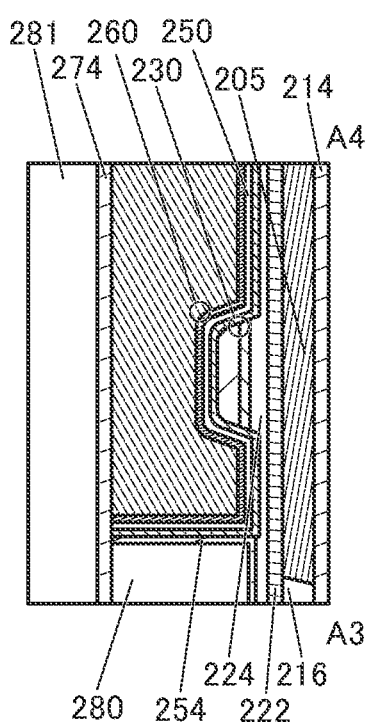
FIGS. 41B and 41C are cross-sectional views illustrating a structure example of the transistor.
Figure 41B:
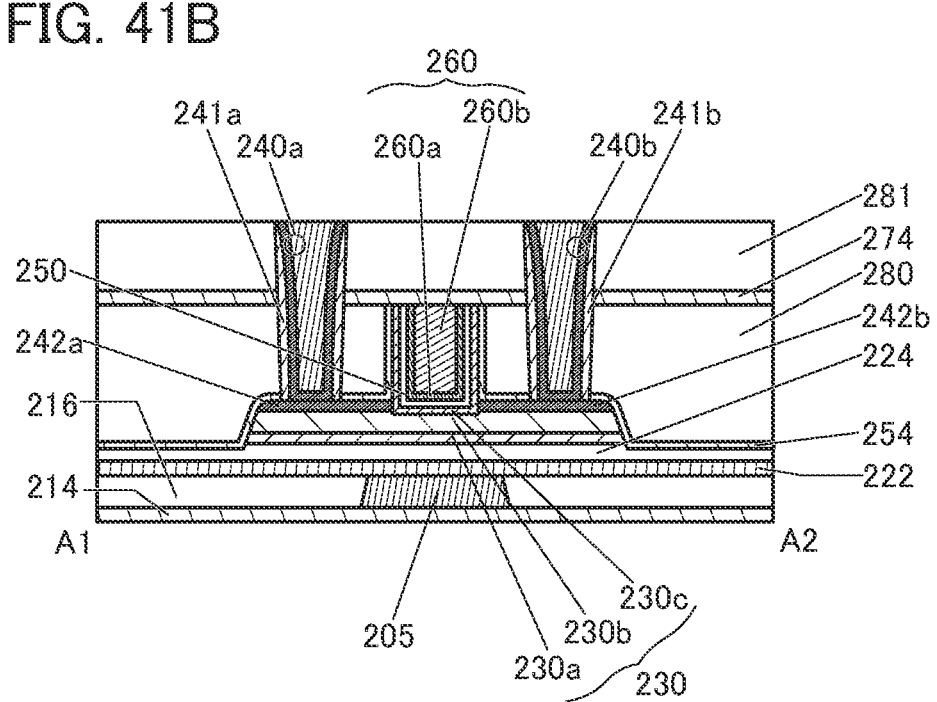

FIGS. 41A to 41C are a top view and cross-sectional views of a transistor 200A that can be used in the display device of one embodiment of the present invention, and the periphery of the transistor 200A. The transistor 200A can be used as the transistors included in the pixel array 833, the gate driver circuit 821, the source driver circuit 822, and the circuit 840 described in Embodiment 1 and the like.

FIG. 41A is a top view of the transistor 200A. FIGS. 41B and 41C are cross-sectional views of the transistor 200A. FIG. 41B is a cross-sectional view taken along the dashed-dotted line A1-A2 in FIG. 41A and shows a cross section of the transistor 200A in the channel length direction. FIG. 41C is a cross-sectional view taken along the dashed-dotted line A3-A4 in FIG. 41A and shows a cross section of the transistor 200A in the channel width direction. Note that for simplification of the drawing, some components are not illustrated in the top view in FIG. 41A.

The transistor 200A includes a metal oxide 230a over a substrate (not illustrated); a metal oxide 230b over the metal oxide 230a; a conductor 242a and a conductor 242b that are apart from each other over the metal oxide 230b; the insulator 280 that is positioned over the conductor 242a and the conductor 242b and has an opening between the conductor 242a and the conductor 242b; a conductor 260 in the opening; an insulator 250 between the conductor 260 and the metal oxide 230b, the conductor 242a, the conductor 242b, and the insulator 280; and a metal oxide 230c between the insulator 250 and the metal oxide 230b, the conductor 242a, the conductor 242b, and the insulator 280. Here, as illustrated in FIGS. 41B and 41C, the top surface of the conductor 260 is substantially aligned with the top surfaces of the insulator 250, the insulator 254, the metal oxide 230c, and the insulator 280. Hereinafter, the metal oxide 230a, the metal oxide 230b, and the metal oxide 230c may be collectively referred to as a metal oxide 230. The conductor 242a and the conductor 242b may be collectively referred to as a conductor 242 in some cases.

As illustrated in FIG. 41B, in the transistor 200A, the side surfaces of the conductors 242a and 242b closer to the conductor 260 are substantially perpendicular. Note that the transistor 200A illustrated in FIGS. 41A to 41C is not limited thereto, and the angle formed between the side surface and the bottom surface of the conductors 242a and 242b may range from 10° to 80°, preferably from 30° to 60°. The facing side surfaces of the conductors 242a and 242b may each have a plurality of surfaces.

As illustrated in FIGS. 41B and 41C, the insulator 254 is preferably provided between the insulator 280 and the insulator 224, the metal oxides 230a and 230b, the conductors 242a and 242b, and the metal oxide 230c. Here, as illustrated in FIGS. 41B and 41C, the insulator 254 preferably includes a region in contact with the side surface of the metal oxide 230c, the top surface and side surface of the conductor 242a, the top surface and side surface of the conductor 242b, the side surface of the metal oxide 230a, the side surface of the metal oxide 230b, and the top surface of the insulator 224.

In the transistor 200A, three layers of the metal oxides 230a, 230b, and 230c are stacked in and around the region where the channel is formed (hereinafter also referred to as channel formation region); however, the present invention is not limited thereto. For example, a two-layer structure of the metal oxides 230b and 230c or a stacked-layer structure of four or more layers may be employed. Although the conductor 260 has a stacked-layer structure of two layers in the transistor 200A, the present invention is not limited thereto.

For example, the conductor 260 may have a single-layer structure or a stacked-layer structure of three or more layers. Furthermore, each of the metal oxides 230*a*, 230*b*, and 230*c* may have a stacked-layer structure of two or more layers.

For example, when the metal oxide 230*c* has a stacked-layer structure including a first metal oxide and a second metal oxide over the first metal oxide, the first metal oxide preferably has a composition similar to that of the metal oxide 230*b* and the second metal oxide preferably has a composition similar to that of the metal oxide 230*a*.

Here, the conductor 260 functions as a gate electrode of the transistor, and the conductor 242*a* and the conductor 242*b* function as a source electrode and a drain electrode. As described above, the conductor 260 is formed to be embedded in the opening of the insulator 280 and the region between the conductor 242*a* and the conductor 242*b*. Here, the positions of the conductor 260, the conductor 242*a*, and the conductor 242*b* with respect to the opening of the insulator 280 are selected in a self-aligned manner. That is, in the transistor 200A, the gate electrode can be positioned between the source electrode and the drain electrode in a self-aligned manner. Thus, the conductor 260 can be formed without an alignment margin, resulting in a reduction in the footprint of the transistor 200A. Consequently, a display device can achieve high definition and have a narrow frame.

In addition, as illustrated in FIGS. 41A to 41C, the conductor 260 preferably includes a conductor 260*a* provided inside the insulator 250 and a conductor 260*b* embedded inside the conductor 260*a*.

As illustrated in FIGS. 41A to 41C, the transistor 200A preferably includes the insulator 214 over the substrate (not illustrated); the insulator 216 over the insulator 214; a conductor 205 embedded in the insulator 216; the insulator 222 over the insulator 216 and the conductor 205; and the insulator 224 over the insulator 222. The metal oxide 230*a* is preferably positioned over the insulator 224.

The insulator 274 and the insulator 281 functioning as interlayer films are preferably provided over the transistor 200A. Here, the insulator 274 is preferably provided in contact with the top surfaces of the conductor 260, the insulator 250, the insulator 254, the metal oxide 230*c*, and the insulator 280.

The insulator 222, the insulator 254, and the insulator 274 preferably have a function of inhibiting diffusion of hydrogen (e.g., at least one of hydrogen atoms and hydrogen molecules). For example, the insulators 222, 254, and 274 preferably have a lower hydrogen permeability than the insulators 224, 250, and 280. Moreover, the insulators 222 and 254 preferably have a function of inhibiting diffusion of oxygen (e.g., at least one of oxygen atoms and oxygen molecules). For example, the insulators 222 and 254 preferably have a lower oxygen permeability than the insulators 224, 250, and 280.

Here, the insulator 224, the metal oxide 230, and the insulator 250 are separated by the insulator 280, the insulator 281, the insulator 254, and the insulator 274. This can inhibit entry of impurities such as hydrogen included in the insulators 280 and 281 and excess oxygen into the insulator 224, the metal oxide 230, and the insulator 250.

A conductor 240 (a conductor 240*a* and a conductor 240*b*) that is electrically connected to the transistor 200A and functions as a plug is preferably provided. Note that an insulator 241 (an insulator 241*a* and an insulator 241*b*) is provided in contact with the side surface of the conductor 240 functioning as a plug. In other words, the insulator 241 is provided in contact with the inner wall of an opening in the insulators 254, 280, 274, and 281. Alternatively, a first conductor of the conductor 240 may be provided in contact with the side surface of the insulator 241 and a second conductor of the conductor 240 may be provided on the inner side of the first conductor. Here, the top surface of the conductor 240 and the top surface of the insulator 281 can be at substantially the same level. Although the first conductor of the conductor 240 and the second conductor of the conductor 240 are stacked in the transistor 200A, the present invention is not limited thereto. For example, the conductor 240 may have a single-layer structure or a stacked-layer structure of three or more layers. In the case where a stacked-layer structure is employed, the layers may be distinguished by numbers corresponding to the formation order.

In the transistor 200A, a metal oxide functioning as an oxide semiconductor (hereinafter such a metal oxide is also referred to as an oxide semiconductor) is preferably used for the metal oxide 230 including the channel formation region (the metal oxides 230*a*, 230*b*, and 230*c*). For example, the metal oxide to be the channel formation region of the metal oxide 230 has a band gap of preferably 2 eV or higher, further preferably 2.5 eV or higher, as described above.

As illustrated in FIG. 41B, the metal oxide 230*b* may have a smaller thickness in a region that is not overlapped by the conductor 242 than in a region overlapped by the conductor 242. The thin region is formed when part of the top surface of the metal oxide 230*b* is removed at the time of forming the conductors 242*a* and 242*b*. When a conductive film to be the conductor 242 is formed, a low-resistance region may be formed on the top surface of the metal oxide 230*b* in the vicinity of the interface with the conductive film. Removing the low-resistance region between the conductor 242*a* and the conductor 242*b* on the top surface of the metal oxide 230*b* in the above manner can inhibit formation of the channel in the region.

According to one embodiment of the present invention, a display device that includes small-size transistors and has high definition can be provided. A display device that includes transistors with a high on-state current and achieves high luminance can be provided. A display device that includes fast transistors and operates at high speed can be provided. A display device that includes transistors having stable electrical characteristics and is highly reliable can be provided. A display device that includes transistors with a low off-state current and achieves low power consumption can be provided.

The structure of the transistor 200A that can be used in the display device of one embodiment of the present invention will be described in detail.

The conductor 205 is placed so as to include a region overlapped by the metal oxide 230 and the conductor 260. The conductor 205 is preferably embedded in the insulator 216. Here, the top surface of the conductor 205 preferably has favorable planarity. For example, the average surface roughness (Ra) of the top surface of the conductor 205 is less than or equal to 1 nm, preferably less than or equal to 0.5 nm, further preferably less than or equal to 0.3 nm. This achieves favorable planarity of the insulator 224 formed over the conductor 205 and increases the crystallinity of the metal oxides 230*b* and 230*c*.

Here, the conductor 260 functions as a first gate (also referred to as top gate) electrode in some cases. The conductor 205 functions as a second gate (also referred to back gate) electrode in some cases. In that case, by changing a potential applied to the conductor 205 independently of a potential applied to the conductor 260, $V_{th}$ of the transistor 200A can be controlled. In particular, by applying a negative potential to the conductor 205, $V_{th}$ of the transistor 200A can be higher, and its off-state current can be reduced. Thus, a drain current of the transistor 200A at the time when a potential applied to the conductor 260 is 0 V can be smaller in the case where a negative potential is applied to the conductor 205 than in the case where the negative potential is not applied to the conductor 205.

The conductor 205 is preferably larger than the channel formation region of the metal oxide 230. It is particularly preferred that the conductor 205 extend beyond an end portion of the metal oxide 230 that intersects with the channel width direction, as illustrated in FIG. 41C. That is, the conductor 205 and the conductor 260 preferably overlap each other with the insulator positioned therebetween, in a region beyond the side surface of the metal oxide 230 in the channel width direction.

With the above structure, the channel formation region of the metal oxide 230 can be electrically surrounded by electric fields of the conductor 260 functioning as the first gate electrode and electric fields of the conductor 205 functioning as the second gate electrode.

As illustrated in FIG. 41C, the conductor 205 is extended to have a function of a wiring. However, without limitation to this structure, a conductor functioning as a wiring may be provided under the conductor 205.

A conductive material containing tungsten, copper, or aluminum as its main component is preferably used for the conductor 205. Note that the conductor 205 is shown as a single layer but may have a stacked-layer structure, for example, a stack of titanium or titanium nitride and any of the above conductive materials.

In addition, a conductor having a function of inhibiting diffusion of impurities such as a hydrogen atom, a hydrogen molecule, a water molecule, a nitrogen atom, a nitrogen molecule, a nitrogen oxide molecule (e.g., $N_2O$, NO, and $NO_2$), and a copper atom, that is, a conductor through which the above impurities are less likely to pass may be provided under the conductor 205. Alternatively, it is preferable to provide a conductor having a function of inhibiting diffusion of oxygen (e.g., at least one of oxygen atoms and oxygen molecules), that is, a conductor through which oxygen is less likely to pass. Note that in this specification, a function of inhibiting diffusion of impurities or oxygen means a function of inhibiting diffusion of any one or all of the above impurities and oxygen.

When the conductor having a function of inhibiting oxygen diffusion is provided under the conductor 205, a reduction in conductivity of the conductor 205 due to oxidation of the conductor 205 can be inhibited. As the conductor having a function of inhibiting oxygen diffusion, tantalum, tantalum nitride, ruthenium, or ruthenium oxide is preferably used, for example. The conductor 205 can therefore be a single layer or a stack of the above conductive materials.

The insulator 214 preferably functions as a barrier insulating film for inhibiting impurities such as water or hydrogen from entering the transistor 200A from the substrate side. Accordingly, the insulator 214 is preferably formed using an insulating material having a function of inhibiting diffusion of impurities such as a hydrogen atom, a hydrogen molecule, a water molecule, a nitrogen atom, a nitrogen molecule, a nitrogen oxide molecule (e.g., $N_2O$, NO, and $NO_2$), and a copper atom, that is, an insulating material through which the above impurities are less likely to pass. Alternatively, the insulator 214 is preferably formed using an insulating material having a function of inhibiting diffusion of oxygen (e.g., at least one of oxygen atoms and oxygen molecules), that is, an insulating material through which oxygen is less likely to pass.

For example, aluminum oxide or silicon nitride is preferably used for the insulator 214. Accordingly, it is possible to inhibit diffusion of impurities such as water or hydrogen into the transistor 200A from the substrate side through the insulator 214. It is also possible to inhibit diffusion of oxygen contained in the insulator 224 and the like toward the substrate through the insulator 214.

The dielectric constant of each of the insulators 216, 280, and 281 functioning as an interlayer film is preferably lower than that of the insulator 214. The use of a material having a low dielectric constant for the interlayer film can reduce the parasitic capacitance between wirings. For example, for the insulators 216, 280, and 281, silicon oxide, silicon oxynitride, silicon nitride oxide, silicon nitride, silicon oxide to which fluorine is added, silicon oxide to which carbon is added, silicon oxide to which carbon and nitrogen are added, porous silicon oxide, or the like is used as appropriate.

The insulators 222 and 224 function as a gate insulator.

Here, it is preferred that the insulator 224 in contact with the metal oxide 230 release oxygen by heating. In this specification and the like, oxygen that is released by heating is referred to as excess oxygen in some cases. For example, silicon oxide or silicon oxynitride can be used as appropriate for the insulator 224. When such an insulator containing oxygen is provided in contact with the metal oxide 230, oxygen vacancies in the metal oxide 230 can be reduced, leading to an improvement in reliability of the transistor 200A.

Specifically, an oxide material that releases some oxygen by heating is preferably used for the insulator 224. An oxide that releases oxygen by heating is an oxide film in which the amount of released oxygen converted into oxygen atoms is greater than or equal to $1.0 \times 10^{18}$ atoms/cm$^3$, preferably greater than or equal to $1.0 \times 10^{19}$ atoms/cm$^3$, further preferably greater than or equal to $2.0 \times 10^{19}$ atoms/cm$^3$ or greater than or equal to $3.0 \times 10^{20}$ atoms/cm$^3$ in thermal desorption spectroscopy (TDS) analysis. Note that the temperature of the film surface in the TDS analysis is preferably higher than or equal to 100° C. and lower than or equal to 700° C., or higher than or equal to 100° C. and lower than or equal to 400° C.

As illustrated in FIG. 41C, the insulator 224 is sometimes thinner in a region overlapped by neither the insulator 254 nor the metal oxide 230b than in the other regions. In the insulator 224, the region overlapped by neither the insulator 254 nor the metal oxide 230b preferably has a thickness with which released oxygen can be adequately diffused.

Like the insulator 214 and the like, the insulator 222 preferably functions as a barrier insulating film that inhibits entry of impurities such as water or hydrogen into the transistor 200A from the substrate side. For example, the insulator 222 preferably has a lower hydrogen permeability than the insulator 224. When the insulator 224, the metal oxide 230, the insulator 250, and the like are surrounded by the insulator 222, the insulator 254, and the insulator 274, entry of impurities such as water or hydrogen into the transistor 200A from the outside can be inhibited.

Furthermore, the insulator 222 preferably has a function of inhibiting diffusion of oxygen (e.g., at least one of oxygen atoms and oxygen molecules); that is, it is preferred that oxygen is less likely to pass through the insulator 222. For example, the insulator 222 preferably has a lower oxygen permeability than the insulator 224. The insulator 222 preferably has a function of inhibiting diffusion of oxygen and impurities, in which case oxygen contained in the metal oxide 230 is less likely to diffuse toward the substrate. The insulator 222 can also inhibit oxidization of the conductor 205 with oxygen contained in the insulator 224 and oxygen contained in the metal oxide 230.

As the insulator 222, an insulator containing an oxide of aluminum and/or an oxide of hafnium, which are insulating materials, is preferably used. As the insulator containing an oxide of one or both of aluminum and hafnium, aluminum oxide or hafnium oxide is preferably used. Alternatively, an oxide containing aluminum and hafnium (hafnium aluminate) or the like is preferably used. The insulator 222 formed using such a material functions as a layer inhibiting oxygen release from the metal oxide 230 and entry of impurities such as hydrogen into the metal oxide 230 from the periphery of the transistor 200A.

Alternatively, aluminum oxide, bismuth oxide, germanium oxide, niobium oxide, silicon oxide, titanium oxide, tungsten oxide, yttrium oxide, or zirconium oxide may be added to the insulator, for example. Alternatively, the insulator may be subjected to nitriding treatment. Silicon oxide, silicon oxynitride, or silicon nitride may be stacked over the insulator.

The insulator 222 may have a single-layer structure or a stacked-layer structure using an insulator containing a high-k material, such as aluminum oxide, hafnium oxide, tantalum oxide, zirconium oxide, lead zirconate titanate (PZT), strontium titanate ($SrTiO_3$), or (Ba, Sr)$TiO_3$ (BST). As miniaturization and high integration of transistors progress, a problem such as generation of leakage current may arise because of a thinner gate insulator. When a high-k material is used for an insulator functioning as the gate insulator, a gate potential at the time when the transistor operates can be lowered while the physical thickness of the gate insulator is maintained.

Note that the insulators 222 and 224 may each have a stacked-layer structure of two or more layers. In that case, the stacked layers are not necessarily formed of the same material and may be formed of different materials. For example, an insulator similar to the insulator 224 may be provided below the insulator 222.

The metal oxide 230 includes the metal oxide 230a, the metal oxide 230b over the metal oxide 230a, and the metal oxide 230c over the metal oxide 230b. The metal oxide 230a under the metal oxide 230b inhibits diffusion of impurities into the metal oxide 230b from the components formed below the metal oxide 230a. The metal oxide 230c over the metal oxide 230b inhibits diffusion of impurities into the metal oxide 230b from the components formed above the metal oxide 230c.

Note that the metal oxide 230 preferably has a stacked-layer structure of oxide layers with different atomic ratios of metal atoms. Specifically, the atomic ratio of the element M to the constituent elements in the metal oxide used as the metal oxide 230a is preferably higher than that in the metal oxide used as the metal oxide 230b. The atomic ratio of the element M to In in the metal oxide used as the metal oxide 230a is preferably higher than that in the metal oxide used as the metal oxide 230b. The atomic ratio of In to the element M in the metal oxide used as the metal oxide 230b is preferably higher than that in the metal oxide used as the metal oxide 230a. The metal oxide 230c can be formed using a metal oxide that can be used as the metal oxide 230a or the metal oxide 230b.

The metal oxides 230a, 230b, and 230c preferably have crystallinity, and are particularly preferably formed using a c-axis-aligned crystalline oxide semiconductor (CAAC-OS). An oxide having crystallinity, such as a CAAC-OS, has a dense structure with small amounts of impurities and defects (e.g., oxygen vacancies) and high crystallinity. This reduces oxygen extraction from the metal oxide 230b by the source electrode or the drain electrode. Accordingly, oxygen extraction from the metal oxide 230b can be inhibited even when heat treatment is performed. Thus, the transistor 200A is stable against high temperatures in the manufacturing process (i.e., thermal budget).

The energy of the conduction band minimum of each of the metal oxides 230a and 230c is preferably higher than that of the metal oxide 230b. In other words, the electron affinity of each of the metal oxides 230a and 230c is preferably smaller than that of the metal oxide 230b. In that case, the metal oxide 230c is preferably formed using a metal oxide that can be used as the metal oxide 230a. Specifically, the atomic ratio of the element M to the constituent elements in the metal oxide used as the metal oxide 230c is preferably higher than that in the metal oxide used as the metal oxide 230b. The atomic ratio of the element M to In in the metal oxide used as the metal oxide 230c is preferably higher than that in the metal oxide used as the metal oxide 230b. The atomic ratio of In to the element M in the metal oxide used as the metal oxide 230b is preferably higher than that in the metal oxide used as the metal oxide 230c.

Here, the energy level of the conduction band minimum is gradually varied at a junction portion of each of the metal oxides 230a, 230b, and 230c. In other words, the energy levels of the conduction band minimum at a junction portion of each of the metal oxides 230a, 230b, and 230c continuously vary or are continuously connected. This can be achieved by decrease in the density of defect states in a mixed layer formed at the interface between the metal oxides 230a and 230b and the interface between the metal oxides 230b and 230c.

Specifically, when the metal oxides 230a and 230b or the metal oxides 230b and 230c contain the same element (as a main component) in addition to oxygen, a mixed layer with a low density of defect states can be formed. For example, in the case where the metal oxide 230b is an In—Ga—Zn oxide, it is preferable to use an In—Ga—Zn oxide, a Ga—Zn oxide, gallium oxide, or the like as each of the metal oxides 230a and 230c. The metal oxide 230c may have a stacked-layer structure. For example, the metal oxide 230c can have a stacked-layer structure of an In—Ga—Zn oxide and a Ga—Zn oxide over the In—Ga—Zn oxide, or a stacked-layer structure of an In—Ga—Zn oxide and gallium oxide over the In—Ga—Zn oxide. In other words, the metal oxide 230c may have a stacked-layer structure of an In—Ga—Zn oxide and an oxide that does not contain In.

Specifically, as the metal oxide 230a, a metal oxide having an atomic ratio of In:Ga:Zn=1:3:4 or In:Ga:Zn=1:1:0.5 can be used. As the metal oxide 230b, a metal oxide having an atomic ratio of In:Ga:Zn=4:2:3 or In:Ga:Zn=3:1:2 can be used. As the metal oxide 230c, a metal oxide having an atomic ratio of In:Ga:Zn=1:3:4, In:Ga:Zn=4:2:3, Ga:Zn=2:1, or Ga:Zn=2:5 can be used. Specific examples of a stacked-layer structure of the metal oxide 230c include a stacked-layer structure of a layer having an atomic ratio of In:Ga:Zn=4:2:3 and a layer having an atomic ratio of Ga:Zn=2:1, a stacked-layer structure of a layer having an atomic ratio of In:Ga:Zn=4:2:3 and a layer having an atomic ratio of Ga:Zn=2:5, and a stacked-layer structure of a layer having an atomic ratio of In:Ga:Zn=4:2:3 and gallium oxide.

At this time, the metal oxide 230b serves as a main carrier path. When the metal oxides 230a and 230c have the above structure, the density of defect states at the interface between the metal oxides 230a and 230b and the interface between the metal oxides 230b and 230c can be made low. This reduces the influence of interface scattering on carrier conduction, and the transistor 200A can have a high on-state current and high frequency characteristics. Note that in the case where the metal oxide 230c has a stacked-layer structure, not only the effect of reducing the density of defect state at the interface between the metal oxides 230b and 230c, but also the effect of inhibiting diffusion of the constituent element of the metal oxide 230c toward the insulator 250 can be expected. Specifically, the metal oxide 230c has a stacked-layer structure in which the upper layer is an oxide that does not contain In, whereby the amount of In that would diffuse toward the insulator 250 can be reduced. Since the insulator 250 functions as a gate insulator, the transistor would show poor characteristics when In diffuses into the insulator 250. Thus, the metal oxide 230c having a stacked-layer structure allows the display device to have high reliability.

The metal oxide 230 is preferably formed using a metal oxide functioning as an oxide semiconductor. For example, the metal oxide to be the channel formation region of the metal oxide 230 has a band gap of preferably 2 eV or higher, further preferably 2.5 eV or higher. The use of a metal oxide having a wide band gap can reduce the off-state current of the transistor. The use of such a transistor can provide a display device with low power consumption.

The conductor 242 (the conductor 242a and the conductor 242b) functioning as the source electrode and the drain electrode is provided over the metal oxide 230b. For the conductor 242, it is preferable to use a metal element selected from aluminum, chromium, copper, silver, gold, platinum, tantalum, nickel, titanium, molybdenum, tungsten, hafnium, vanadium, niobium, manganese, magnesium, zirconium, beryllium, indium, ruthenium, iridium, strontium, and lanthanum; an alloy containing any of the above metal elements; an alloy containing a combination of the above metal elements; or the like. For example, it is preferable to use tantalum nitride, titanium nitride, tungsten, a nitride containing titanium and aluminum, a nitride containing tantalum and aluminum, ruthenium oxide, ruthenium nitride, an oxide containing strontium and ruthenium, an oxide containing lanthanum and nickel, or the like. Tantalum nitride, titanium nitride, a nitride containing titanium and aluminum, a nitride containing tantalum and aluminum, ruthenium oxide, ruthenium nitride, an oxide containing strontium and ruthenium, and an oxide containing lanthanum and nickel are preferable because they are oxidation-resistant conductive materials or materials that retain their conductivity even after absorbing oxygen.

When the conductor 242 is provided in contact with the metal oxide 230, the oxygen concentration of the metal oxide 230 in the vicinity of the conductor 242 sometimes decreases. In addition, a metal compound layer that contains the metal contained in the conductor 242 and the component of the metal oxide 230 is sometimes formed in the metal oxide 230 in the vicinity of the conductor 242. In such cases, the carrier density of the region in the metal oxide 230 in the vicinity of the conductor 242 increases, and the region becomes a low-resistance region.

Here, the region between the conductor 242a and the conductor 242b is formed to overlap with the opening of the insulator 280. In this manner, the conductor 260 can be formed in a self-aligned manner between the conductor 242a and the conductor 242b.

The insulator 250 functions as a gate insulator. The insulator 250 is preferably in contact with a top surface of the metal oxide 230c. For the insulator 250, any of silicon oxide, silicon oxynitride, silicon nitride oxide, silicon nitride, silicon oxide to which fluorine is added, silicon oxide to which carbon is added, silicon oxide to which carbon and nitrogen are added, and porous silicon oxide can be used. In particular, silicon oxide and silicon oxynitride, which have thermal stability, are preferable.

As in the insulator 224, the concentration of impurities such as water or hydrogen in the insulator 250 is preferably reduced. The thickness of the insulator 250 is preferably greater than or equal to 1 nm and less than or equal to 20 nm.

A metal oxide may be provided between the insulator 250 and the conductor 260. The metal oxide preferably has a function of inhibiting oxygen diffusion from the insulator 250 into the conductor 260. Thus, oxidation of the conductor 260 due to oxygen in the insulator 250 can be inhibited.

Note that the metal oxide has a function of part of the gate insulator in some cases. For that reason, when silicon oxide, silicon oxynitride, or the like is used for the insulator 250, the metal oxide is preferably a high-k material with a high dielectric constant. The gate insulator having a stacked-layer structure of the insulator 250 and the metal oxide enables the transistor 200A to be thermally stable and have a high dielectric constant. Accordingly, a gate potential applied during operation of the transistor can be lowered while the physical thickness of the gate insulator is maintained. In addition, the equivalent oxide thickness (EOT) of the insulator functioning as the gate insulator can be reduced.

Specifically, a metal oxide containing one or more of hafnium, aluminum, gallium, yttrium, zirconium, tungsten, titanium, tantalum, nickel, germanium, magnesium, and the like can be used. It is particularly preferable to use an insulator containing an oxide of one or both of aluminum and hafnium, such as aluminum oxide, hafnium oxide, or an oxide containing aluminum and hafnium (hafnium aluminate).

Although the conductor 260 has a two-layer structure in FIGS. 41A to 41C, the conductor 260 may have a single-layer structure or a stacked-layer structure of three or more layers.

The conductor 260a is preferably formed using the aforementioned conductive material having a function of inhibiting diffusion of impurities such as hydrogen atoms, hydrogen molecules, water molecules, nitrogen atoms, nitrogen molecules, nitrogen oxide molecules (e.g., $N_2O$, NO, and $NO_2$), and copper atoms. Alternatively, the conductor 260a is preferably formed using a conductive material having a function of inhibiting diffusion of oxygen (e.g., at least one of oxygen atoms and oxygen molecules).

When the conductor 260a has a function of inhibiting diffusion of oxygen, the conductivity of the conductor 260b can be prevented from being lowered because of oxidization of the conductor 260b due to oxygen in the insulator 250. As a conductive material having a function of inhibiting oxygen diffusion, tantalum, tantalum nitride, ruthenium, or ruthenium oxide is preferably used, for example.

The conductor 260b is preferably formed using a conductive material containing tungsten, copper, or aluminum as its main component. The conductor 260 also functions as a wiring and thus is preferably a conductor having high conductivity. For example, a conductive material containing tungsten, copper, or aluminum as its main component can be used. The conductor 260b may have a stacked-layer structure, for example, a stacked-layer structure of titanium or titanium nitride and the above conductive material.

As illustrated in FIGS. 41A and 41C, the side surface of the metal oxide 230 is covered with the conductor 260 in a region where the metal oxide 230b is not overlapped by the conductor 242, that is, the channel formation region of the metal oxide 230. Accordingly, electric fields of the conductor 260 functioning as the first gate electrode are likely to act on the side surface of the metal oxide 230. Hence, the transistor 200A can have a higher on-state current and improved frequency characteristics.

The insulator 254 as well as the insulator 214 and the like preferably functions as a barrier insulating film that inhibits impurities such as water or hydrogen from entering the transistor 200A from the insulator 280 side. For example, it is preferable that the insulator 254 less transmit hydrogen than the insulator 224. Furthermore, as illustrated in FIGS. 41B and 41C, the insulator 254 preferably includes a region in contact with the side surface of the metal oxide 230c, the top surface and side surface of the conductor 242a, the top surface and side surface of the conductor 242b, the side surface of the metal oxide 230a, the side surface of the metal oxide 230b, and the top surface of the insulator 224. Such a structure can inhibit entry of hydrogen of the insulator 280 into the metal oxide 230 through top surfaces or side surfaces of the conductor 242a, the conductor 242b, the metal oxide 230a, the metal oxide 230b, and the insulator 224.

Furthermore, the insulator 254 preferably has a function of inhibiting diffusion of oxygen (e.g., at least one of oxygen atoms and oxygen molecules); that is, it is preferable that oxygen is less likely to pass through the insulator 254. For example, it is preferred that the insulator 254 less transmit oxygen than the insulator 280 or the insulator 224.

The insulator 254 is preferably formed by a sputtering method. When the insulator 254 is formed by a sputtering method in an oxygen-containing atmosphere, oxygen can be added to a region of the insulator 224 in contact with the insulator 254 and its vicinity. Thus, oxygen can be supplied from the region to the metal oxide 230 through the insulator 224. Here, with the insulator 254 having a function of inhibiting upward oxygen diffusion, diffusion of oxygen from the metal oxide 230 into the insulator 280 can be inhibited. Moreover, with the insulator 222 having a function of inhibiting downward oxygen diffusion, diffusion of oxygen from the metal oxide 230 toward the substrate can be inhibited. In the above manner, oxygen is supplied to the channel formation region of the metal oxide 230. Accordingly, oxygen vacancies in the metal oxide 230 can be reduced, so that the transistor can be prevented from having normally-on characteristics.

As the insulator 254, an insulator containing an oxide of aluminum and/or hafnium is formed, for example. Note that as the insulator containing an oxide of aluminum and/or hafnium, aluminum oxide, hafnium oxide, an oxide containing aluminum and hafnium (hafnium aluminate), or the like is preferably used.

The insulator 224, the insulator 250, and the metal oxide 230 are covered with the insulator 254 having a barrier property against hydrogen, whereby the insulator 280 is isolated from the insulator 224, the metal oxide 230, and the insulator 250 by the insulator 254. This inhibits entry of impurities such as hydrogen from the outside of the transistor 200A, resulting in favorable electrical characteristics and reliability of the transistor 200A.

The insulator 280 is provided over the insulator 224, the metal oxide 230, and the conductor 242 with the insulator 254 placed therebetween. The insulator 280 preferably includes, for example, silicon oxide, silicon oxynitride, silicon nitride oxide, silicon oxide to which fluorine is added, silicon oxide to which carbon is added, silicon oxide to which carbon and nitrogen are added, or porous silicon oxide. Silicon oxide and silicon oxynitride are particularly preferable in terms of high thermal stability. A material such as silicon oxide, silicon oxynitride, or porous silicon oxide is preferably used, in which case a region including oxygen that is released by heating can be easily formed.

The concentration of impurities such as water or hydrogen in the insulator 280 is preferably lowered. The top surface of the insulator 280 may be planarized.

The insulator 274, like the insulator 214 or the like, preferably functions as a barrier insulating film that inhibits entry of impurities such as water and hydrogen into the insulator 280. The insulator 274 can be formed using an insulator that can be used as the insulator 214 or the insulator 254, for example.

The insulator 281 functioning as an interlayer film is preferably provided over the insulator 274. As in the insulator 224 or the like, the concentration of impurities such as water and hydrogen in the insulator 281 is preferably reduced.

The conductor 240a and the conductor 240b are provided in openings formed in the insulators 281, 274, 280, and 254. The conductors 240a and 240b are positioned to face each other with the conductor 260 therebetween. Note that the top surfaces of the conductors 240a and 240b may be level with the top surface of the insulator 281.

The insulator 241a is provided in contact with the inner wall of the opening in the insulators 281, 274, 280, and 254, and the first conductor of the conductor 240a is formed in contact with the side surface of the insulator 241a. The conductor 242a is positioned on at least part of the bottom of the opening, and thus the conductor 240a is in contact with the conductor 242a. Similarly, the insulator 241b is provided in contact with the inner wall of another opening in the insulators 281, 274, 280, and 254, and the first conductor of the conductor 240b is formed in contact with the side surface of the insulator 241b. The conductor 242b is positioned on at least part of the bottom of the opening, and thus the conductor 240b is in contact with the conductor 242b.

The conductors 240a and 240b are preferably formed using a conductive material containing tungsten, copper, or aluminum as its main component. The conductors 240a and 240b may have a stacked-layer structure.

When the conductor 240 has a stacked-layer structure, the aforementioned conductor having a function of inhibiting diffusion of impurities such as water or hydrogen is preferably used for the conductor in contact with the metal oxide 230a, the metal oxide 230b, the conductor 242, the insulator 254, the insulator 280, the insulator 274, and the insulator 281. For example, tantalum, tantalum nitride, titanium, titanium nitride, ruthenium, or ruthenium oxide is preferably used. The conductive material having a function of inhibiting diffusion of impurities such as water or hydrogen can be used as a single layer or stacked layers. The use of the conductive material can prevent oxygen added to the insulator 280 from being absorbed by the conductors 240a and 240b, and prevent impurities such as water or hydrogen from entering the metal oxide 230 through the conductors 240a and 240b from the components above the insulator 281.

The insulators 241a and 241b are formed using any of the insulators that can be used for the insulator 254, for example. Since the insulators 241a and 241b are provided in contact with the insulator 254, impurities such as water and hydrogen in the insulator 280 or the like can be prevented from entering the metal oxide 230 through the conductors 240a and 240*b*. Furthermore, oxygen contained in the insulator 280 can be prevented from being absorbed by the conductors 240*a* and 240*b*.

Although not illustrated, a conductor functioning as a wiring may be provided in contact with the top surfaces of the conductors 240*a* and 240*b*. The conductor functioning as a wiring is preferably formed using a conductive material containing tungsten, copper, or aluminum as its main component. The conductor may have a stacked-layer structure, for example, a stack of titanium or titanium nitride and the above conductive material. Note that the conductor may be formed to be embedded in an opening provided in an insulator.

<Structure Example 2 of Transistor>

Figure 42A:
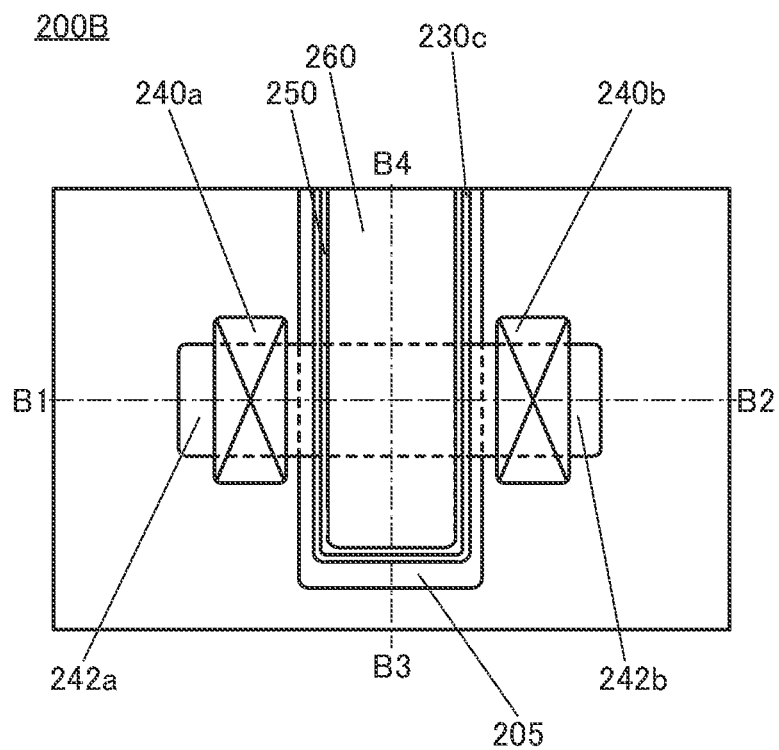
FIG. 42A is a top view illustrating a structure example of a transistor.
Figure 42C:
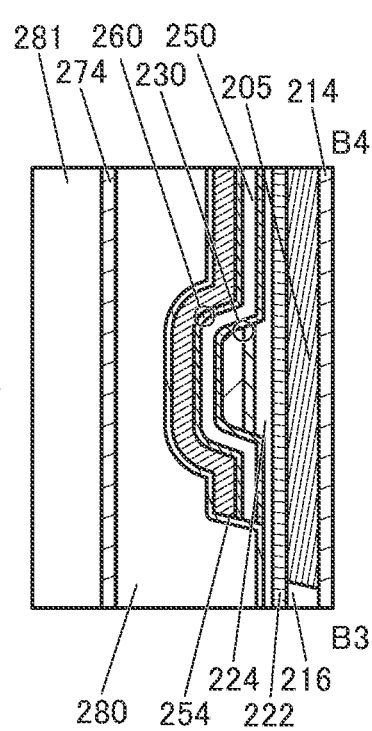
FIGS. 42B and 42C are cross-sectional views illustrating a structure example of the transistor.
Figure 42B:
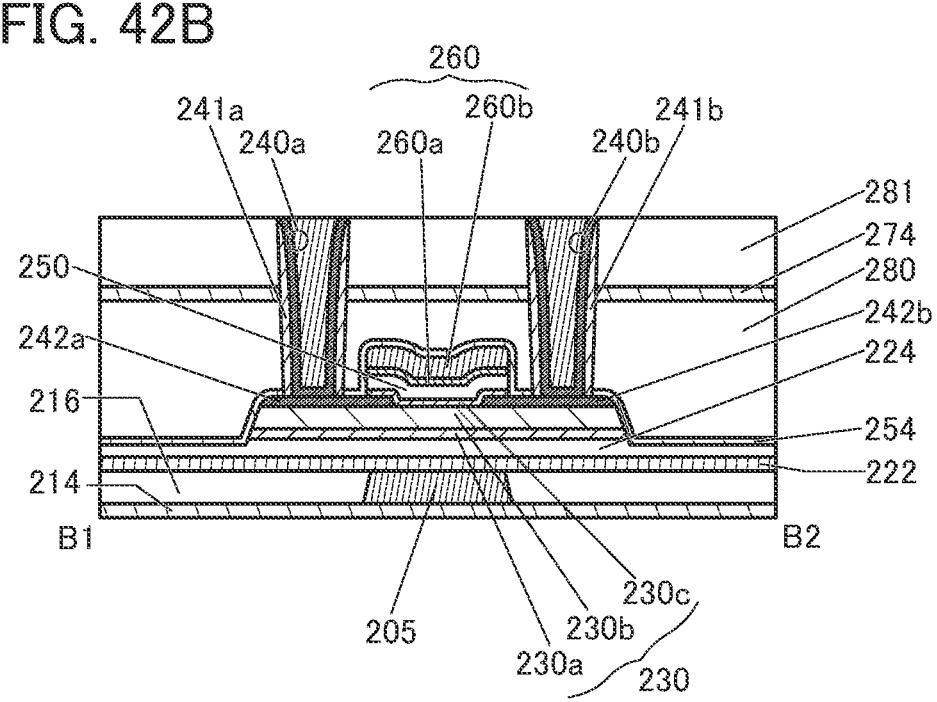

FIGS. 42A to 42C are a top view and cross-sectional views of a transistor 200B that can be used in the display device of one embodiment of the present invention, and the periphery of the transistor 200B. The transistor 200B is a variation example of the transistor 200A.

FIG. 42A is a top view of the transistor 200B. FIGS. 42B and 42C are cross-sectional views of the transistor 200B. FIG. 42B is a cross-sectional view taken along the dashed-dotted line B1-B2 in FIG. 42A and shows a cross section of the transistor 200B in the channel length direction. FIG. 42C is a cross-sectional view taken along the dashed-dotted line B3-B4 in FIG. 42A and shows a cross section of the transistor 200B in the channel width direction. Note that for simplification of the drawing, some components are not illustrated in the top view in FIG. 42A.

In the transistor 200B, the conductor 242*a* and the conductor 242*b* each have a region overlapping with the metal oxide 230*c*, the insulator 250, and the conductor 260. Thus, the transistor 200B can have a high on-state current. In addition, the transistor 200B can be a transistor that is easy to control.

The conductor 260 functioning as a gate electrode includes the conductor 260*a* and the conductor 260*b* over the conductor 260*a*. The conductor 260*a* is preferably formed using a conductive material having a function of inhibiting diffusion of impurities such as a hydrogen atom, a hydrogen molecule, a water molecule, and a copper atom. Alternatively, the conductor 260*a* is preferably formed using a conductive material having a function of inhibiting diffusion of oxygen (e.g., at least one of oxygen atoms and oxygen molecules).

When the conductor 260*a* has a function of inhibiting oxygen diffusion, the range of choices for the material of the conductor 260*b* can be expanded. That is, the conductor 260*a* inhibits oxidation of the conductor 260*b*, thereby inhibiting the decrease in conductivity of the conductor 260*b*.

The insulator 254 is preferably provided to cover the top surface and the side surface of the conductor 260, the side surface of the insulator 250, and the side surface of the metal oxide 230*c*. Note that the insulator 254 is preferably formed using an insulating material having a function of inhibiting diffusion of oxygen and impurities such as water or hydrogen.

The insulator 254 can inhibit oxidation of the conductor 260. Moreover, the insulator 254 can inhibit diffusion of impurities such as water and hydrogen contained in the insulator 280 into the transistor 200B.

<Structure Example 3 of Transistor>

Figure 43A:
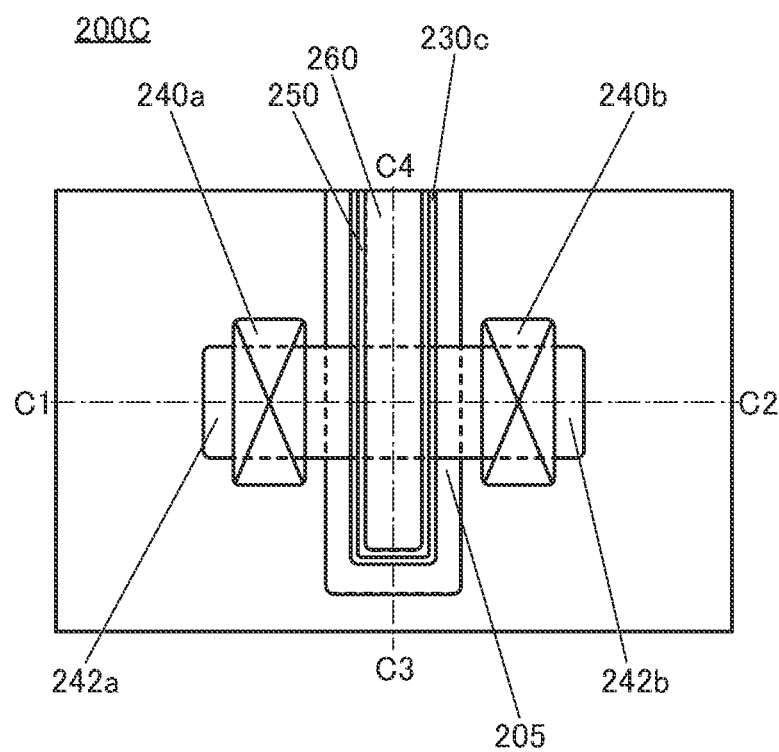
FIG. 43A is a top view illustrating a structure example of a transistor.
Figure 43C:
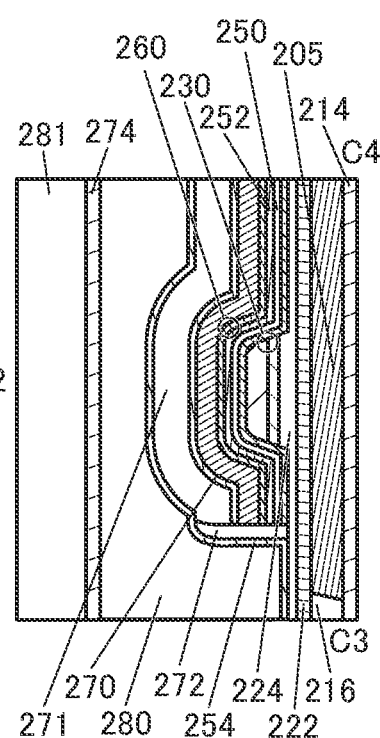
FIGS. 43B and 43C are cross-sectional views illustrating a structure example of the transistor.
Figure 43B:
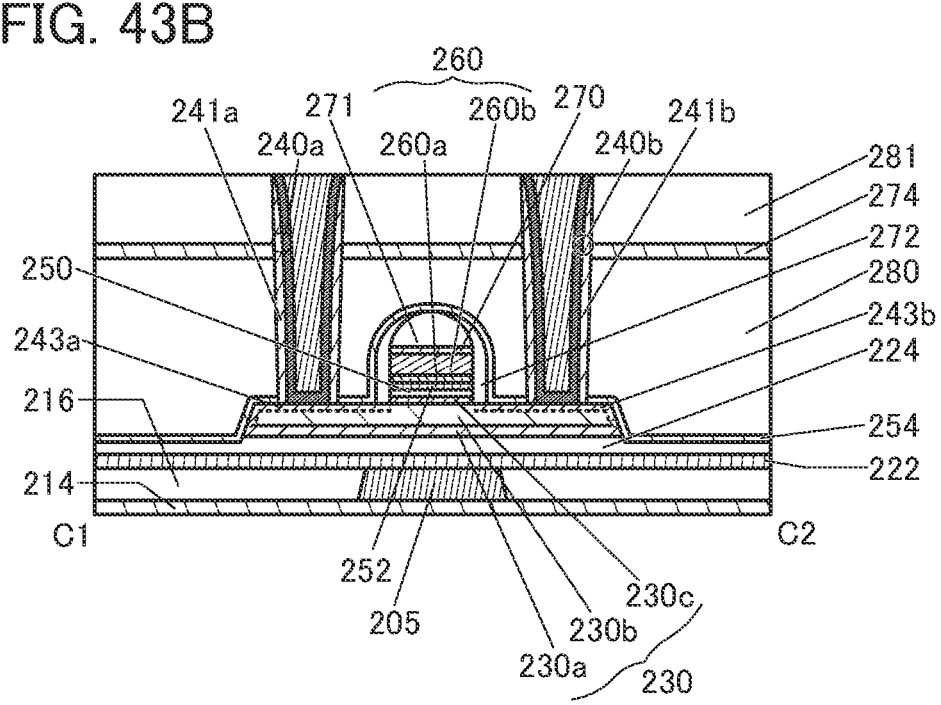

FIGS. 43A to 43C are a top view and cross-sectional views of a transistor 200C that can be used in the display device of one embodiment of the present invention, and the periphery of the transistor 200C. The transistor 200C is a variation example of the transistor 200A.

FIG. 43A is a top view of the transistor 200C. FIGS. 43B and 43C are cross-sectional views of the transistor 200C. FIG. 43B is a cross-sectional view taken along the dashed-dotted line C1-C2 in FIG. 43A and shows a cross section of the transistor 200C in the channel length direction. FIG. 43C is a cross-sectional view taken along the dashed-dotted line C3-C4 in FIG. 43A and shows a cross section of the transistor 200C in the channel width direction. Note that for simplification of the drawing, some components are not illustrated in the top view in FIG. 43A.

The transistor 200C includes the insulator 250 over the metal oxide 230*c*, a metal oxide 252 over the insulator 250, the conductor 260 over the metal oxide 252, an insulator 270 over the conductor 260, and an insulator 271 over the insulator 270.

The metal oxide 252 preferably has a function of inhibiting diffusion of oxygen. When the metal oxide 252 that inhibits oxygen diffusion is provided between the insulator 250 and the conductor 260, diffusion of oxygen into the conductor 260 is inhibited. That is, the reduction in the amount of oxygen supplied to the metal oxide 230 can be inhibited. Furthermore, oxidation of the conductor 260 can be inhibited.

Note that the metal oxide 252 may function as part of a gate electrode. For example, an oxide semiconductor that can be used for the metal oxide 230 can be used for the metal oxide 252. In this case, when the conductor 260 is formed by a sputtering method, the metal oxide 252 can have a reduced electric resistance and become a conductor. Such a conductor can be referred to as an oxide conductor (OC) electrode.

Note that the metal oxide 252 may function as part of a gate insulator. Therefore, when silicon oxide, silicon oxynitride, or the like, which has high thermal stability, is used for the insulator 250, a metal oxide that is a high-k material with a high dielectric constant is preferably used as the metal oxide 252. This stacked-layer structure enables the transistor 200C to be thermally stable and have a high dielectric constant. Accordingly, a gate potential that is applied during operation of the transistor can be lowered while the physical thickness of the gate insulator is maintained. In addition, the equivalent oxide thickness (EOT) of the insulator functioning as the gate insulator can be reduced.

Although the metal oxide 252 in the transistor 200C is shown as a single layer, the metal oxide 252 may have a stacked-layer structure of two or more layers. For example, a metal oxide functioning as part of a gate electrode and a metal oxide functioning as part of a gate insulator may be stacked.

When the metal oxide 252 included in the transistor 200C functions as a gate electrode, the on-state current of the transistor 200C can be increased without weakening the influence of electric fields from the conductor 260. When the metal oxide 252 functions as a gate insulator, the distance between the conductor 260 and the metal oxide 230 can be maintained owing to the physical thickness of the insulator 250 and the metal oxide 252. Thus, leakage current between the conductor 260 and the metal oxide 230 can be reduced. Consequently, in the transistor 200C having the stacked-layer structure of the insulator 250 and the metal oxide 252, it is easy to adjust the physical distance between the conductor 260 and the metal oxide 230 and the intensity of electric fields applied from the conductor 260 to the metal oxide 230.

Specifically, for the metal oxide 252, a material obtained by lowering the resistance of an oxide semiconductor that can be used for the metal oxide 230 can be used. Alternatively, a metal oxide containing one or more of hafnium, aluminum, gallium, yttrium, zirconium, tungsten, titanium, tantalum, nickel, germanium, magnesium, and the like can be used.

It is particularly preferable to use an insulator containing an oxide of one or both of aluminum and hafnium, such as aluminum oxide, hafnium oxide, or an oxide containing aluminum and hafnium (hafnium aluminate). In particular, hafnium aluminate is preferable because it has higher heat resistance than hafnium oxide and thus is less likely to be crystallized by heat treatment in a later step. Note that the metal oxide 252 is not necessarily provided. Design is appropriately determined in consideration of required transistor characteristics.

The insulator 270 is preferably formed using an insulating material having a function of inhibiting the passage of oxygen and impurities such as water or hydrogen. For example, aluminum oxide or hafnium oxide is preferably used. In that case, oxidization of the conductor 260 due to oxygen from above the insulator 270 can be inhibited. Moreover, entry of impurities such as water or hydrogen from above the insulator 270 into the metal oxide 230 through the conductor 260 and the insulator 250 can be inhibited.

The insulator 271 functions as a hard mask. By provision of the insulator 271, the conductor 260 can be processed to have a side surface that is substantially perpendicular. Specifically, the angle formed by the side surface of the conductor 260 and the surface of the substrate can be greater than or equal to 750 and less than or equal to 100°, preferably greater than or equal to 800 and less than or equal to 95°.

The insulator 271 may be formed using an insulating material having a function of inhibiting the passage of oxygen and impurities such as water or hydrogen so that the insulator 271 also functions as a barrier layer. In this case, the insulator 270 is not necessarily provided.

The insulator 270, the conductor 260, the metal oxide 252, the insulator 250, and the metal oxide 230c are selectively removed using the insulator 271 as a hard mask, whereby their side surfaces can be substantially aligned with each other and the surface of the metal oxide 230b can be partly exposed.

The transistor 200C includes a region 243a and a region 243b on part of the exposed surface of the metal oxide 230b. One of the regions 243a and 243b functions as a source region, and the other of the regions 243a and 243b functions as a drain region.

The regions 243a and 243b can be formed by addition of an impurity element such as phosphorus or boron to the exposed surface of the metal oxide 230b by an ion implantation method, an ion doping method, a plasma immersion ion implantation method, or plasma treatment, for example. In this embodiment and the like, an impurity element refers to an element other than main constituent elements.

Alternatively, the regions 243a and 243b can be formed in such manner that, after part of the surface of the metal oxide 230b is exposed, a metal film is formed and then heat treatment is performed so that the element contained in the metal film is diffused into the metal oxide 230b.

The electrical resistivity of the regions of the metal oxide 230b to which the impurity element is added decreases. For that reason, the regions 243a and 243b are sometimes referred to as impurity regions or low-resistance regions.

The regions 243a and 243b can be formed in a self-aligned manner by using the insulator 271 and/or the conductor 260 as a mask. Accordingly, the conductor 260 does not overlap the region 243a and/or the region 243b, so that the parasitic capacitance can be reduced. Moreover, an offset region is not formed between the channel formation region and the source/drain region (the region 243a or the region 243b). The formation of the regions 243a and 243b in a self-aligned manner achieves a higher on-state current, a lower threshold voltage, and a higher operating frequency, for example.

The transistor 200C includes an insulator 272 on the side surfaces of the insulator 271, the insulator 270, the conductor 260, the metal oxide 252, the insulator 250, and the metal oxide 230c. The insulator 272 is preferably an insulator having a low dielectric constant. The insulator 272 is preferably silicon oxide, silicon oxynitride, silicon nitride oxide, silicon nitride, silicon oxide to which fluorine is added, silicon oxide to which carbon is added, silicon oxide to which carbon and nitrogen are added, porous silicon oxide, or a resin, for example. In particular, silicon oxide, silicon oxynitride, silicon nitride oxide, and porous silicon oxide are preferable because an excess oxygen region can be easily formed in the insulator 272 in a later step. Silicon oxide and silicon oxynitride are preferable because of their thermal stability. The insulator 272 preferably has a function of diffusing oxygen.

Note that an offset region may be provided between the channel formation region and the source/drain region in order to further reduce the off-state current. The offset region is a region where the electrical resistivity is high and the impurity element is not added. The offset region can be formed by addition of the impurity element after the formation of the insulator 272. In this case, the insulator 272 serves as a mask like the insulator 271 or the like. Thus, the impurity element is not added to the region of the metal oxide 230b overlapped by the insulator 272, so that the electrical resistivity of the region can be kept high.

The transistor 200C also includes the insulator 254 over the insulator 272 and the metal oxide 230. The insulator 254 is preferably formed by a sputtering method. The insulator formed by a sputtering method can be an insulator containing few impurities such as water or hydrogen.

Note that an oxide film formed by a sputtering method may extract hydrogen from the component over which the oxide film is formed. For that reason, the insulator 254 formed by a sputtering method absorbs hydrogen and water from the metal oxide 230 and the insulator 272. This reduces the hydrogen concentration in the metal oxide 230 and the insulator 272.

<Materials for Transistor>

Materials that can be used for the transistor will be described.

<<Substrate>>

As a substrate where the transistor is formed, an insulator substrate, a semiconductor substrate, or a conductor substrate can be used, for example. Examples of the insulator substrate include a glass substrate, a quartz substrate, a sapphire substrate, a stabilized zirconia substrate (e.g., an yttria-stabilized zirconia substrate), and a resin substrate. Examples of the semiconductor substrate include a semiconductor substrate of silicon or germanium and a compound semiconductor substrate of silicon carbide, silicon germanium, gallium arsenide, indium phosphide, zinc oxide, or gallium oxide. Another example includes a semiconductor substrate in which an insulator region is provided in the above semiconductor substrate, e.g., a silicon on insulator (SOI) substrate. Examples of the conductor substrate include a graphite substrate, a metal substrate, an alloy substrate, and a conductive resin substrate. Other examples include a substrate containing a nitride of a metal, a substrate including an oxide of a metal, an insulator substrate provided with a conductor or a semiconductor, a semiconductor substrate provided with a conductor or an insulator, and a conductor substrate provided with a semiconductor or an insulator. Alternatively, any of these substrates provided with an element may be used. Examples of the element provided over the substrate include a capacitor, a resistor, a switching element, and a memory element.

<<Insulator>>

Examples of an insulator include an insulating oxide, an insulating nitride, an insulating oxynitride, an insulating nitride oxide, an insulating metal oxide, an insulating metal oxynitride, and an insulating metal nitride oxide.

With miniaturization and high integration of transistors, for example, a problem such as generation of leakage current may arise because of a thin gate insulator. When a high-k material is used for an insulator functioning as a gate insulator, the driving voltage of the transistor can be lowered while the physical thickness of the gate insulator is kept. On the other hand, when a material having a low dielectric constant is used for an insulator functioning as an interlayer film, the parasitic capacitance between wirings can be reduced. Accordingly, a material is preferably selected depending on the function of an insulator.

Examples of the insulator having a high dielectric constant include gallium oxide, hafnium oxide, zirconium oxide, an oxide containing aluminum and hafnium, an oxynitride containing aluminum and hafnium, an oxide containing silicon and hafnium, an oxynitride containing silicon and hafnium, and a nitride containing silicon and hafnium.

Examples of the insulator having a low dielectric constant include silicon oxide, silicon oxynitride, silicon nitride oxide, silicon nitride, silicon oxide to which fluorine is added, silicon oxide to which carbon is added, silicon oxide to which carbon and nitrogen are added, porous silicon oxide, and a resin.

When a transistor including an oxide semiconductor is surrounded by insulators having a function of inhibiting transmission of oxygen and impurities such as hydrogen (e.g., the insulators 214, 222, 254, and 274), the electrical characteristics of the transistor can be stable. An insulator with a function of inhibiting transmission of oxygen and impurities such as hydrogen can be formed to have a single-layer structure or a stacked-layer structure including an insulator containing, for example, boron, carbon, nitrogen, oxygen, fluorine, magnesium, aluminum, silicon, phosphorus, chlorine, argon, gallium, germanium, yttrium, zirconium, lanthanum, neodymium, hafnium, or tantalum. Specifically, as the insulator with a function of inhibiting transmission of oxygen and impurities such as hydrogen, a metal oxide such as aluminum oxide, magnesium oxide, gallium oxide, germanium oxide, yttrium oxide, zirconium oxide, lanthanum oxide, neodymium oxide, hafnium oxide, or tantalum oxide or a metal nitride such as aluminum nitride, aluminum titanium nitride, titanium nitride, silicon nitride oxide, or silicon nitride can be used.

An insulator functioning as a gate insulator preferably includes a region containing oxygen that is released by heating. For example, when silicon oxide or silicon oxynitride that includes a region containing oxygen released by heating is provided in contact with the metal oxide 230, oxygen vacancies in the metal oxide 230 can be compensated.

<<Conductor>>

For the conductor, it is preferable to use a metal element selected from aluminum, chromium, copper, silver, gold, platinum, tantalum, nickel, titanium, molybdenum, tungsten, hafnium, vanadium, niobium, manganese, magnesium, zirconium, beryllium, indium, ruthenium, iridium, strontium, lanthanum, and the like; an alloy containing any of the above metal elements; an alloy containing a combination of the above metal elements; or the like. For example, it is preferable to use tantalum nitride, titanium nitride, tungsten, a nitride containing titanium and aluminum, a nitride containing tantalum and aluminum, ruthenium oxide, ruthenium nitride, an oxide containing strontium and ruthenium, an oxide containing lanthanum and nickel, or the like. Tantalum nitride, titanium nitride, a nitride containing titanium and aluminum, a nitride containing tantalum and aluminum, ruthenium oxide, ruthenium nitride, an oxide containing strontium and ruthenium, and an oxide containing lanthanum and nickel are preferable because they are oxidation-resistant conductive materials or materials that maintain their conductivity even after absorbing oxygen. Alternatively, a semiconductor having high electric conductivity, typified by polycrystalline silicon containing an impurity element such as phosphorus, or silicide such as nickel silicide may be used.

Conductors formed using any of the above materials may be stacked. For example, a stacked-layer structure combining a material containing any of the above metal elements and a conductive material containing oxygen may be used. Alternatively, a stacked-layer structure combining a material containing any of the above metal elements and a conductive material containing nitrogen may be used. Further alternatively, a stacked-layer structure combining a material containing any of the above metal elements, a conductive material containing oxygen, and a conductive material containing nitrogen may be used.

When a metal oxide is used for the channel formation region of the transistor, the conductor functioning as the gate electrode preferably employs a stacked-layer structure using a material containing any of the above metal elements and a conductive material containing oxygen. In this case, the conductive material containing oxygen is preferably provided on the channel formation region side. When the conductive material containing oxygen is provided on the channel formation region side, oxygen released from the conductive material is easily supplied to the channel formation region.

It is particularly preferable to use, for the conductor functioning as the gate electrode, a conductive material containing oxygen and a metal element contained in the metal oxide in which the channel is formed. A conductive material containing any of the above metal elements and nitrogen may be used. For example, a conductive material containing nitrogen, such as titanium nitride or tantalum nitride, may be used. Indium tin oxide, indium oxide containing tungsten oxide, indium zinc oxide containing tungsten oxide, indium oxide containing titanium oxide, indium tin oxide containing titanium oxide, indium zinc oxide, or indium tin oxide to which silicon is added may be used. Indium gallium zinc oxide containing nitrogen may be used. With the use of such a material, hydrogen contained in the metal oxide in which the channel is formed can be captured in some cases. Alternatively, hydrogen entering from a surrounding insulator or the like can be captured in some cases.

<<Metal Oxide>>

A metal oxide contains preferably at least indium or zinc and particularly preferably indium and zinc. In addition, aluminum, gallium, yttrium, tin, or the like is preferably contained. Furthermore, one or more elements selected from boron, titanium, iron, nickel, germanium, zirconium, molybdenum, lanthanum, cerium, neodymium, hafnium, tantalum, tungsten, magnesium, and the like may be contained.

Here, the case where the metal oxide is an In-M-Zn oxide that contains indium, an element M, and zinc is considered. The element M is aluminum, gallium, yttrium, tin, or the like. Other examples that can be used as the element M include boron, titanium, iron, nickel, germanium, zirconium, molybdenum, lanthanum, cerium, neodymium, hafnium, tantalum, tungsten, and magnesium. Note that two or more of the above elements can be used in combination as the element M in some cases.

Note that in this specification and the like, a metal oxide containing nitrogen is also referred to as a metal oxide in some cases. A metal oxide containing nitrogen may be referred to as a metal oxynitride.

[Structure of Metal Oxide]

An oxide semiconductor (metal oxide) is classified into a single crystal oxide semiconductor and anon-single-crystal oxide semiconductor. Examples of a non-single-crystal oxide semiconductor include a CAAC-OS, a polycrystalline oxide semiconductor, a nanocrystalline oxide semiconductor (nc-OS), an amorphous-like oxide semiconductor (a-like OS), and an amorphous oxide semiconductor.

[Impurities]

Here, the influence of impurities in the metal oxide is described. When the metal oxide contains an alkali metal or an alkaline earth metal, defect states are formed and carriers are generated in some cases. Thus, a transistor using a metal oxide containing an alkali metal or an alkaline earth metal in a channel formation region tends to have normally-on characteristics. Therefore, it is preferable to reduce the concentration of an alkali metal or an alkaline earth metal in the metal oxide. Specifically, the concentration of an alkali metal or an alkaline earth metal in the metal oxide, measured by secondary ion mass spectrometry (SIMS), is lower than or equal to $1\times10^{18}$ atoms/cm$^3$, preferably lower than or equal to $2\times10^{16}$ atoms/cm$^3$.

Hydrogen contained in a metal oxide reacts with oxygen bonded to a metal atom and forms water. Hence, hydrogen contained in a metal oxide may cause oxygen vacancies in the metal oxide. Entry of hydrogen into the oxygen vacancies generates electrons serving as carriers in some cases. Furthermore, some hydrogen may react with oxygen bonded to a metal atom and generate an electron serving as a carrier. Thus, a transistor including a metal oxide that contains hydrogen tends to have normally-on characteristics.

For this reason, hydrogen in the metal oxide is preferably reduced as much as possible. Specifically, the hydrogen concentration of the metal oxide measured by SIMS is lower than $1\times10^{20}$ atoms/cm$^3$, preferably lower than $1\times10^{19}$ atoms/cm$^3$, further preferably lower than $5\times10^{18}$ atoms/cm$^3$, still further preferably lower than $1\times10^{18}$ atoms/cm$^3$. When a metal oxide with a sufficiently reduced impurity concentration is used for a channel formation region of a transistor, the transistor can have stable electrical characteristics.

As a metal oxide used for a semiconductor of a transistor, a thin film having high crystallinity is preferably used. With the thin film, the stability or reliability of the transistor can be improved. As the thin film, a thin film of a single crystal metal oxide or a thin film of a polycrystalline metal oxide can be used, for example. However, a high-temperature process or a laser heating process is required to form the thin film of a single crystal metal oxide or the thin film of a polycrystalline metal oxide over a substrate. Thus, the manufacturing cost is increased, and the throughput is decreased.

At least part of any of the structure examples, the drawings corresponding thereto, and the like described in this embodiment can be implemented in combination with any of the other structure examples, the other drawings, and the like as appropriate.

At least part of this embodiment can be implemented in combination with any of the other embodiments described in this specification as appropriate.

REFERENCE NUMERALS

10: electronic device, 10a: electronic device, 10b: electronic device, 11: display device, 11a: display device, 11b: display device, 12: housing, 12a: housing, 12b: housing, 13: optical component, 13a: optical component, 13b: optical component, 14: wearing part, 14a: wearing part, 14b: wearing part, 15: imaging device, 15a: imaging device, 15b: imaging device, 16: display region, 16a: display region, 16b: display region, 18: frame, 19: camera, 21: lens, 22: reflective plate, 23: reflective surface, 25: light, 26: transmitted light, 31: housing, 32: opening, 33: display device, 34: fixing member, 35: optical component, 35a: optical component, 35b: optical component, 36: frame, 36a: frame, 36b: frame, 37: imaging device, 37a: imaging device, 37b: imaging device, 40: light source, 40a: light source, 40b: light source, 51: information presentation unit, 52: subject detection unit, 53: feature extraction unit, 54: estimation unit, 55: information generation unit, 56: transmitter, 57: receiver, 61: input layer, 62: intermediate layer, 63: output layer, 71: data, 72: data, 73: data, 74: data, 81: user, 82: user, 110: channel formation region, 111: source region, 112: drain region, 113: gate electrode, 114: opening, 115: wiring, 116: opening, 117: wiring, 118: opening, 119: opening, 120: opening, 121: wiring, 122: wiring, 123: wiring, 130: channel formation region, 131: source region, 132: drain region, 133: gate electrode, 134: opening, 135: wiring, 136: opening, 137: wiring, 138: opening, 139: opening, 140: opening, 141: wiring, 142: wiring, 143: wiring, 151: semiconductor, 152: conductor, 200A: transistor, 200B: transistor, 200C: transistor, 205: conductor, 214: insulator, 216: insulator, 222: insulator, 224: insulator, 230: metal oxide, 230a: metal oxide, 230b: metal oxide, 230c: metal oxide, 240: conductor, 240a: conductor, 240b: conductor, 241: insulator, 241a: insulator, 241b: insulator, 242: conductor, 242a: conductor, 242b: conductor, 243a: region, 243b: region, 244: insulator, 250: insulator, 252: metal oxide, 254: insulator, 260: conductor, 260a: conductor, 260b: conductor, 270: insulator, 271: insulator, 272: insulator, 274: insulator, 280: insulator, 281: insulator, 301a: conductor, 301b: conductor, 305: conductor, 311: conductor, 313: conductor, 317: conductor, 321: lower electrode, 323: insulator, 325: upper electrode, 331: conductor, 333: conductor, 335: conductor, 337: conductor, 341: conductor, 343: conductor, 347: conductor, 351: conductor, 353: conductor, 355: conductor, 357: conductor, 361: insulator, 363: insulator, 401: circuit, 403: element isolation layer, 405: insulator, 407: insulator, 409: insulator, 411: insulator, 413: insulator, 415: insulator, 417: insulator, 419: insulator, 421: insulator, 441: transistor, 443: conductor, 445: insulator, 447: semiconductor region, 449a: low-resistance region, 449b: low-resistance region, 451: conductor, 453: conductor, 455: conductor, 457: conductor, 459: conductor, 461: conductor, 463: conductor, 465: conductor, 467: conductor, 469: conductor, 471: conductor, 501: insulator, 503: insulator, 505: insulator, 507: insulator, 509: insulator, 511: transistor, 513: transistor, 515: capacitor, 517: capacitor, 520: circuit, 521: transistor, 525: transistor, 527: transistor, 529: transistor, 535: wiring, 537: wiring, 539: wiring, 541: wiring, 543: wiring, 545: wiring, 552: transistor, 554: transistor, 562: capacitor, 572: light-emitting element, 572_1: light-emitting element, 572_2: light-emitting element, 601: transistor, 602: transistor, 603: transistor, 613: insulator, 614: insulator, 616: insulator, 622: insulator, 624: insulator, 644: insulator, 654: insulator, 674: insulator, 680: insulator, 681: insulator, 701: substrate, 705: substrate, 712: sealant, 716: FPC, 721: hole-injection layer, 722: hole-transport layer, 723: light-emitting layer, 724: electron-transport layer, 725: electron-injection layer, 730: insulator, 732: sealing layer, 734: insulator, 736: coloring layer, 738: light-blocking layer, 750: transistor, 760: connection electrode, 772: conductor, 778: component, 780: anisotropic conductor, 786: EL layer, 786a: EL layer, 786b: EL layer, 786c: EL layer, 788: conductor, 790: capacitor, 792: charge generation layer, 810: display device, 820: layer, 821: gate driver circuit, 821a: gate driver circuit, 821b: gate driver circuit, 822: source driver circuit, 823: region, 823a: region, 823b: region, 824: demultiplexer circuit, 830: layer, 831: wiring, 831-1: wiring, 831-2: wiring, 831_1: wiring, 831_2: wiring, 831a: wiring, 831b: wiring, 832: wiring, 832-1: wiring, 832-2: wiring, 832_1: wiring, 832_2: wiring, 833: pixel array, 834: pixel, 835a: wiring, 835b: wiring, 840: circuit, 841: receiver circuit, 842: serial-to-parallel converter circuit, 843: buffer circuit, 844: shift register circuit, 845: latch circuit, 846: D/A converter circuit, 846a: potential generator circuit, 846b: pass transistor logic circuit, 847: amplifier circuit, 848: resistor, 849: pass transistor, 851: transistor, 852: transistor, 853: transistor, 854: transistor, 855: transistor, 856: transistor, 857: transistor, 858: transistor, 859: transistor, 860: transistor, 861: transistor, 862: transistor, 863: transistor, 864: capacitor, 865: capacitor, 866: capacitor, 867: source follower circuit, 870: region, 871: transistor, 872: transistor, 873: dummy transistor, 901: subpixel, 901B: subpixel, 901G: subpixel, 901R: subpixel, 902: pixel, 911: conductor, 912: conductor, 913: semiconductor, 914: semiconductor, 915a: conductor, 915b: conductor, 916a: conductor, 916b: conductor, 917: conductor, 918: conductor, 919: conductor, 920: conductor, 921: conductor, 922: conductor, 923: conductor, 924: conductor, 925: conductor, 926: conductor, 927: conductor, 928: conductor, 929: conductor, 930: conductor, 931: conductor, 940: subpixel, 940_1: subpixel, 940_2: subpixel, 940B: subpixel, 940G: subpixel, 940R: subpixel, 941: pixel, 951: conductor, 952: semiconductor, 953: semiconductor, 954a: conductor, 954b: conductor, 955a: conductor, 955b: conductor, 956: conductor, 957: conductor, 958: conductor, 959: conductor, 960: conductor, 961: conductor, 962: conductor, 963: conductor, 964: conductor, 965: conductor, 966: conductor, 967: conductor, 968: conductor, 969: conductor, 970: conductor, 971: semiconductor, 972: semiconductor, 973a: conductor, 973b: conductor, 974a: conductor, 974b: conductor, 975: conductor, 976: conductor, 977: conductor, 978: conductor, 979: conductor, 980: conductor, 981: conductor, 982: conductor, 983: conductor, 984: conductor, 985: conductor, 986: conductor, 987: conductor, 990: conductor, 991: bonding layer, 992: insulator, 993: coloring layer, 993a: coloring layer, 993b: coloring layer, 993IR: coloring layer, 993R: coloring layer, 994: bonding layer, 995: substrate, 1001: substrate, 1002: insulator, 1003: transistor, 1004: insulator, 1005: insulator, 1010: photoelectric conversion element, 1010_1: photoelectric conversion element, 1010_2: photoelectric conversion element, 1011: active layer, 1021: insulator, 1022: insulator, 1023: insulator, 1024: insulator, 1025: insulator, 1026: insulator, 1027: insulator, 1031: insulator, 1032: insulator, 1033: insulator, 1034: insulator, 1035: insulator, 1036: insulator, 1042: insulator, 1043: insulator, 1044: insulator, 1045: insulator, 1046: insulator, 1047: insulator This application is based on Japanese Patent Application Serial No. 2019-030646 filed with Japan Patent Office on Feb. 22, 2019, the entire contents of which are hereby incorporated by reference.

The invention claimed is:

1. A glasses-type electronic device comprising:
a first optical component;
a second optical component;
a frame;
an imaging device;
a feature extraction unit; and
an emotion estimation unit,
wherein the frame is in contact with a side surface of the first optical component and a side surface of the second optical component,
wherein the imaging device is in contact with the frame,
wherein the imaging device is configured to detect part of a user's face,
wherein the feature extraction unit is configured to extract a feature of the user's face from the detected part of the user's face, and
wherein the emotion estimation unit is configured to estimate information on the user from the extracted feature.

2. The glasses-type electronic device according to claim 1, wherein the information is the degree of fatigue or emotion of the user.

3. The glasses-type electronic device according to claim 1, further comprising a display device,
wherein the display device displays an image corresponding to the information.

4. The glasses-type electronic device according to claim 3, wherein the display device comprises a light-emitting element, and wherein the light-emitting element is an organic electroluminescent element.

5. The glasses-type electronic device according to claim 3,
wherein the display device comprises a transistor, and
wherein the transistor comprises a metal oxide in a channel formation region.

6. A glasses-type electronic device comprising:
a first optical component;
a second optical component;
a frame;
an imaging device;
a feature extraction unit;
an emotion estimation unit; and
a display device,
wherein the imaging device comprises a photoelectric conversion element configured to detect an amount of received light,
wherein the frame is in contact with a side surface of the first optical component and a side surface of the second optical component,
wherein the imaging device is in contact with the frame, wherein the imaging device is configured to detect part of a user's face, wherein the feature extraction unit is configured to extract a feature of the user's face from the detected part of the user's face, wherein the emotion estimation unit is configured to estimate information on the user from the extracted feature, wherein the display device comprises a first layer and a second layer that are stacked, wherein the first layer comprises a gate driver circuit and a source driver circuit, wherein the second layer comprises a pixel array comprising a matrix of pixels, wherein the gate driver circuit and the source driver circuit each comprise a region overlapping with some of the pixels, and wherein the gate driver circuit comprises a region overlapping with the source driver circuit.

7. The glasses-type electronic device according to claim 6, wherein the display device comprises a digital to analog converter circuit, wherein the digital to analog converter circuit comprises a potential generator circuit and a pass transistor logic circuit, wherein the potential generator circuit is placed outside the source driver circuit, wherein the pass transistor logic circuit is placed in the source driver circuit, wherein the potential generator circuit is configured to generate a plurality of potentials having different levels, and wherein the pass transistor logic circuit is configured to receive image data and output any of the potentials generated by the potential generator circuit on the basis of a digital value of the image data.

8. The glasses-type electronic device according to claim 6, wherein each of the pixels comprises a light-emitting element, and wherein the light-emitting element is an organic electroluminescent element.

9. The glasses-type electronic device according to claim 6, wherein each of the pixels comprises a transistor, and wherein the transistor comprises a metal oxide in a channel formation region.

10. The glasses-type electronic device according to claim 1, further comprising a transmitter and a receiver.

11. The glasses-type electronic device according to claim 6, further comprising a transmitter and a receiver.

* * * * *